United States Patent
Onikubo et al.

(10) Patent No.: US 6,280,859 B1
(45) Date of Patent: *Aug. 28, 2001

(54) LIGHT-EMITTING MATERIAL FOR ORGANO-ELECTROLUMINESCENCE DEVICE AND FOR ORGANIC ELECTROLUMINESCENCE DEVICE WHICH THE MATERIAL IS APPLIED

(75) Inventors: Toshikazu Onikubo; Michiko Tamano; Satoshi Okutsu; Toshio Enokida, all of Tokyo (JP)

(73) Assignee: Toyo Ink Manufacturing Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/042,569

(22) Filed: Mar. 17, 1998

(30) Foreign Application Priority Data

Mar. 17, 1997 (JP) .................................................. 9-062568

(51) Int. Cl.[7] .......................... H05B 33/14; C07C 211/00
(52) U.S. Cl. .......................... 428/690; 428/704; 428/917; 313/504; 313/506; 252/301.16; 564/305; 564/315; 564/431; 564/433
(58) Field of Search ................... 428/690, 704, 428/917; 313/504, 506; 252/301.16; 564/305, 315, 330, 429, 430, 431, 433

(56) References Cited

U.S. PATENT DOCUMENTS

| 5,759,444 | * | 6/1998 | Enokida et al. ............ 252/301.16 |
| 5,811,834 | * | 9/1998 | Tamano et al. ............ 257/40 |
| 5,948,941 | * | 9/1999 | Tamano et al. ............ 564/315 |

FOREIGN PATENT DOCUMENTS

| 0666298 | 8/1995 | (EP) . |
| 0757035 | 2/1997 | (EP) . |
| 0786926 | 7/1997 | (EP) . |

OTHER PUBLICATIONS

Patent Abstracts of Japan vol. 017, No. 704 (C–1146), Dec. 22, 1993 (JP 05 239455 A (Ricoh Co Ltd), Sep. 17, 1993).
Patent Abstracts of Japan vol. 096, No. 006, Jun. 28, 1996 (JP 08 053397 A (Toyo Ink Mfg Co Ltd), Feb. 27, 1996).
Stickley K R et al, "Cation Radicals of 1,3,5–Tris(diarylamino) benzenes" Tetrahedron Letters, vol. 36, No. 10, Mar. 6, 1995, pp. 1585–1588.
Patent Abstracts of Japan vol. 097, No. 002, Feb. 28, 1997 (JP 08 259937 A (Toyo Ink Mfg Co Ltd), Oct. 8, 1996).

* cited by examiner

Primary Examiner—Marie Yamnitzky
(74) Attorney, Agent, or Firm—Wenderoth, Lind & Ponack, L.L.P.

(57) ABSTRACT

A light-emitting material which serves to emit light having a high brightness and is almost free of deterioration in light emission, and an organic EL device for which the light-emitting material is adapted, the material having the formula [1],

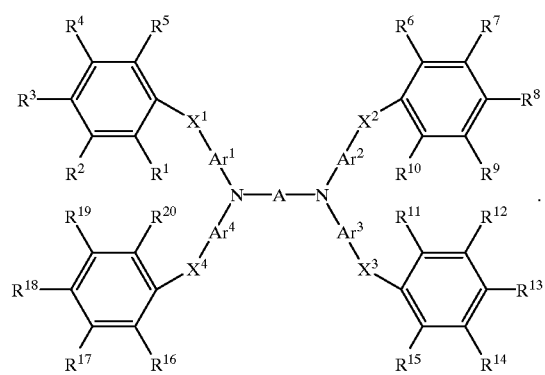

6 Claims, No Drawings

LIGHT-EMITTING MATERIAL FOR ORGANO-ELECTROLUMINESCENCE DEVICE AND FOR ORGANIC ELECTROLUMINESCENCE DEVICE WHICH THE MATERIAL IS APPLIED

FIELD OF THE INVENTION

The present invention relates to a light-emitting material for an organo-electroluminescence ("EL" hereinafter) device for use as a flat light source or display, and to a light-emitting device having a high brightness.

PRIOR ART

An EL device using an organic substance is expected to have a great promise as a solid light-emitting inexpensive large-screen, full-color display device, and developments thereof are being made in many ways. Generally, an EL device is composed of a light-emitting layer and a pair of facing electrodes sandwiching the light-emitting layer. The light emission of an EL device is the following phenomenon. When an electric field is applied between the two electrodes, the cathode injects electrons into the light-emitting layer, and the anode injects holes into the light-emitting layer. When the electrons recombine with the holes in the light-emitting layer, their energy level shifts back to a valence bond band to release energy as light.

As compared with inorganic EL devices, conventional organic EL devices require high voltage, and their light emission brightness and light emission efficiency are low. Further, conventional organic EL devices deteriorate in properties to a great extent, and no organic EL device has been put to practical use.

There has been recently proposed an organic EL device which is produced by laminating a thin film containing an organic compound having a fluorescent quantum effect of emitting light at a low voltage as low as less than 10 V, and it attracts attention (Appl. Phy. Lett., Vol. 51, page 913, 1987). The above organic EL device has a light-emitting layer containing a metal chelate complex and a hole-injecting layer containing an amine-based compound, and emits green light having a high brightness. The above organic EL device achieves nearly practically usable performance, since it accomplishes a brightness of 1,000 cd/m$^2$ and a maximum light emission efficiency of 1.5 lm/W at a direct current voltage of 6 or 7V.

However, conventional organic EL devices including the above organic EL device are not yet satisfactory in brightness although these organic EL devices are improved in brightness to some extent. Further, they have a serious problem that their stability is insufficient in their continuous operation for a long period of time. That is because, for example, a metal chelate complex such as a tris(8-hydroxyquinolinate)-aluminum complex, or the like, is chemically unstable when an electric field is applied for light emission, is poor in adhesion to a cathode and extremely deteriorates in a short period of emission. For the above reasons, it is desired to develop a light-emitting material having an excellent light emission capacity and durability for developing an organic EL device which has a high light emission brightness and a high light emission efficiency and can perform a light emission in its continuous operation.

SUMMARY OF THE INVENTION

It is an object of the present invention to provide an organic EL device having a high light emission brightness and having excellent stability in the continuous operation.

The present inventors have made diligent studies for achieving the above object, and have found that an organic EL device having a light-emitting layer for which the material of any one of the formulae [1], [4] and [5] is adapted has a high light emission brightness and a high light emission efficiency and has excellent stability in the continuous operation. On the basis of the above finding, the present invention has been completed.

According to the present invention, there is provided a light-emitting material of the formula [1] for an organic EL device,

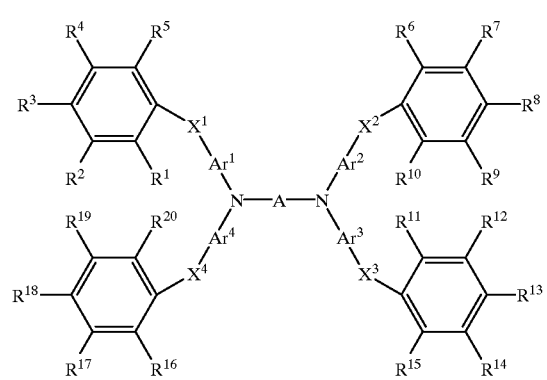

[1]

wherein A is a substituted or non-substituted aromatic group, a substituted or non-substituted fused aromatic group (excluding a group of the formula [2] shown below), a substituted or non-substituted hetero-aromatic group, a substituted or non-substituted fused hetero-aromatic group or a divalent group (excluding a group of the formula [3] shown below) in which 2 to 10 identical or different groups out of the above groups are bonded to each other directly or through at least one of an oxygen atom, a nitrogen atom, a sulfur atom, a linear structural unit having 1 to 20 carbon atoms and optionally containing a hetero-atom, or a non-aromatic ring structural unit, each of Ar$^1$ to Ar$^4$ is independently a substituted or non-substituted aromatic group or a substituted or non-substituted fused aromatic group, each of X$^1$ to X$^4$ is independently —O—, —S—, >C=O, >SO$_2$, —(C$_x$H$_{2x}$)—O—(C$_y$H$_{2y}$)— (in which each of x and y is an integer of 0 to 20, while x+y=0 in no case), a substituted or non-substituted alkylidene group having 2 to 20 carbon atoms, a substituted or non-substituted alkylene group having 2 to 20 carbon atoms or a substituted or non-substituted divalent alicyclic residue, and each of R$^1$ to R$^{20}$ is independently a hydrogen atom, a halogen atom, a substituted or non-substituted alkyl group, a substituted or non-substituted alkoxy group, a substituted or non-substituted aromatic group, a substituted or non-substituted hetero-aromatic group or a substituted or non-substituted amino group (provided that adjacent groups of R$^1$ to R$^5$, R$^6$ to R$^{10}$, R$^{11}$ to R$^{15}$, or R$^{16}$ to R$^{20}$ may bond to each other to form a fresh ring),

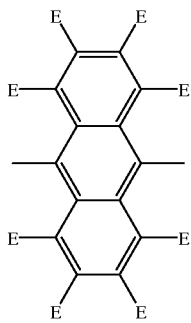

[2]

wherein E is a hydrogen atom or any adjacent two E's may bond to each other to form a fresh six-membered ring.

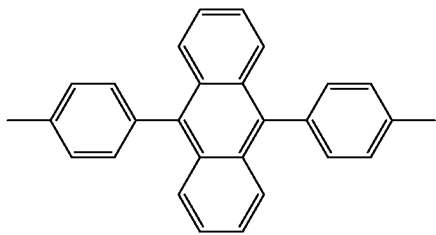

[3]

Further, according to the present invention, there is provided a light-emitting material of the formula [4] for an organic EL device,

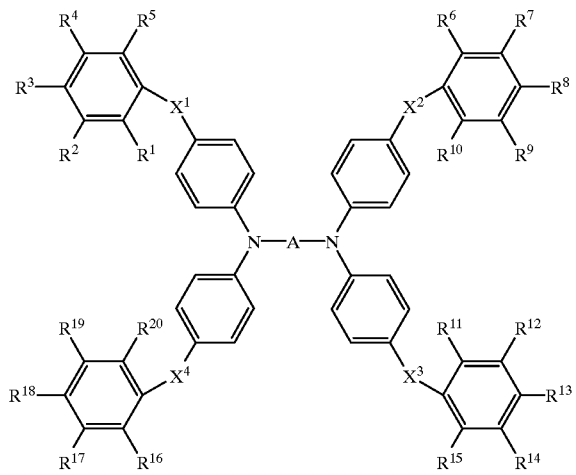

[4]

wherein A, $X^1$ to $X^4$ and $R^1$ to $R^{20}$ are as defined above.

According to the present invention, further, there is provided a light-emitting material of the formula [5] for an organic EL device,

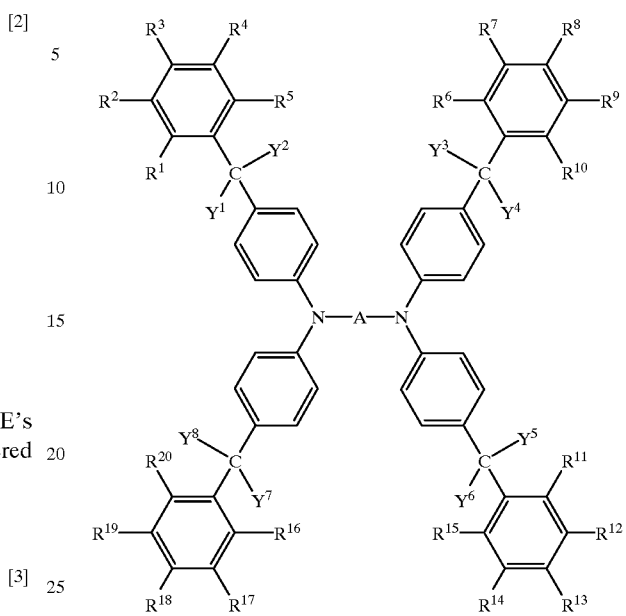

[5]

wherein A and $R^1$ to $R^{20}$ are as defined above, and each of $Y^1$ to $Y^8$ is a substituted or non-substituted alkyl group having 1 to 20 carbon atoms or a substituted or non-substituted aromatic group having 6 to 16 carbon atoms (provided that groups of $Y^1$ and $Y^2$, $Y^3$ and $Y^4$, $Y^5$ and $Y^6$, or $Y^7$ and $Y^8$ may form a substituted or non-substituted alicyclic group having 5 to 7 carbon atoms).

Further, according to the present invention, there is provided an organic EL device comprising a light-emitting layer or a plurality of organic compound layers including the light-emitting layer and a pair of electrodes, the light-emitting layer or a plurality of the organic compound layers being sandwiched between a pair of the electrodes, wherein the light-emitting layer contains the above light-emitting material.

DETAILED DESCRIPTION OF THE INVENTION

In the compounds of the formulae [1], [4] and [5] in the present invention, A is a substituted or non-substituted divalent aromatic group, a substituted or non-substituted divalent fused aromatic group, a substituted or non-substituted divalent hetero-aromatic group, a substituted or non-substituted divalent fused hetero-aromatic group or a divalent group in which 2 to 10 identical or different groups out of the above groups are bonded to each other directly or through an oxygen atom, a nitrogen atom, a sulfur atom, or a linear or non-aromatic structural unit containing a hetero-atom. Those sites of A which bond to nitrogen atoms have a ring structure each.

Specific examples of A include substituted or non-substituted divalent aromatic or fused aromatic group residues of benzene, toluene, xylene, ethylbenzene, naphthalene, anthracene (excluding a case where 9- and 10-positions thereof bond), phenanthrene, fluorene, pyrene, chrysene, naphthacene, perylene, azulene, fluorenone, anthraquinone, dibenzosuberenone and tetracyanoquinodimethane, and divalent hetero-aromatic or fused-hetero-aromatic residues of furan, thiophene, pyrole, pyridine, pyrone, oxazole, pyrazine, oxadiazole, triazole, thiadiazole, indole, quinoline, isoquinoline, carbazole, acridine, thioxanthone, coumarin, acridone, diphenylenesulfone, quinoxaline, benzothiazole, phenazine, phenanthroline, phenothiazine, quinacridone, flavanthrone and indanthrone. Further, A includes divalent residues having a structure in which at least 2 identical or different ring-structural units bond, such as divalent residues of biphenyl, terphenyl, binaphthyl, bifluorenylidene, bipyridine, biquinoline, flavone, phenyltriazine, bisbenzothiazole, bithiophene, phenylbenzotriazole, phenylbenzimidazole, phenylacridine, bis(benzooxazolyl) thiophene, bis(phenyloxazolyl)benzene, biphenylphenyloxadiazole, diphenylbenzoquinone, diphenylisobenzofuran, diphenylpyridine, stilbene, dibenzyl, diphenylmethane, bis(phenylisopropyl)benzene, diphenylfluorene, diphenylhexafluoropropane, dibenzyl naphthyl ketone, dibenzylidenecyclohexanone, distylylnaphthalene, (phenylethyl)benzylnaphthalene, diphenyl ether, methyldiphenylamine, benzophenone, phenylbenzoate, diphenyl urea, diphenyl sulfide, diphenyl sulfone, diphenoxybiphenyl, bis(phenoxyphenyl) sulfone, bis(phenoxyphenyl)propane, diphenoxybenzene, ethylene glycol diphenyl ether, neopentyl glycol diphenyl ether, dipicolylamine and dipyridylamine.

Table 1 shows specific examples of chemical structure of A in the light-emitting material of the present invention, although A shall not be limited thereto.

TABLE 1

| Divalent group | Chemical structure (—A—) |
|---|---|
| (A-1) |  |
| (A-2) | 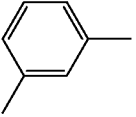 |
| (A-3) | 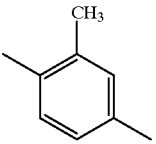 |
| (A-4) | 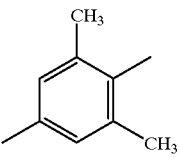 |
| (A-5) | 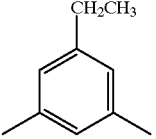 |
| (A-6) | 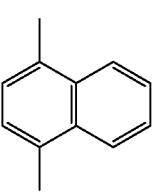 |

TABLE 1-continued
| Divalent group | Chemical structure (—A—) |
|---|---|
| (A-7) | 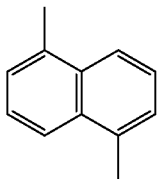 |
| (A-8) | 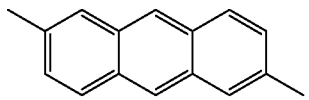 |
| (A-9) | 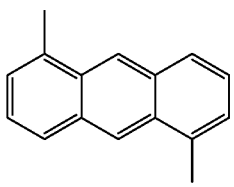 |
| (A-10) | 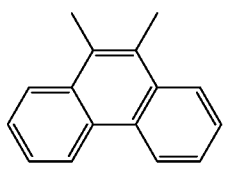 |
| (A-11) | 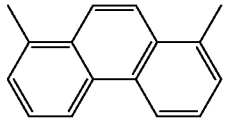 |
| (A-12) | 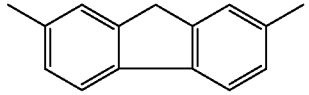 |
| (A-13) | 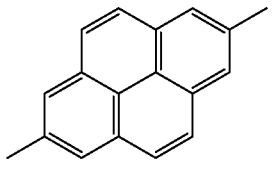 |
| (A-14) | 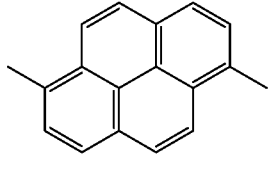 |
| (A-15) | 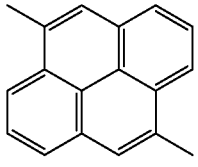 |

TABLE 1-continued
| Divalent group | Chemical structure (—A—) |
|---|---|
| (A-16) | 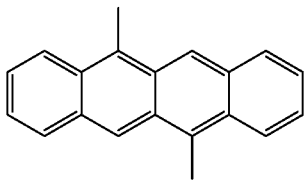 |
| (A-17) | 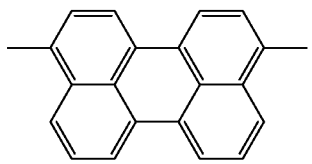 |
| (A-18) | 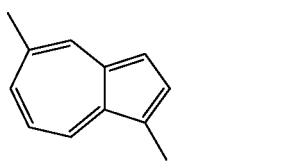 |
| (A-19) | 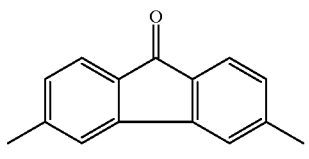 |
| (A-20) | 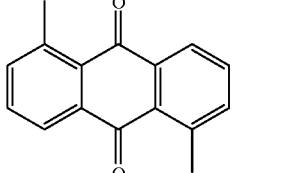 |
| (A-21) | 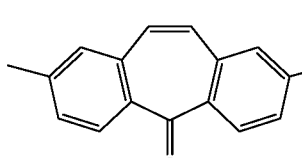 |
| (A-22) | 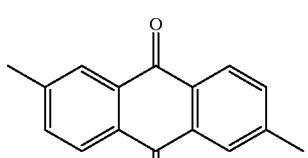 |

TABLE 1-continued
| Divalent group | Chemical structure (—A—) |
|---|---|
| (A-23) | 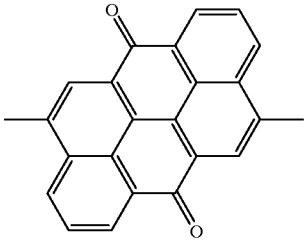 |
| (A-24) | 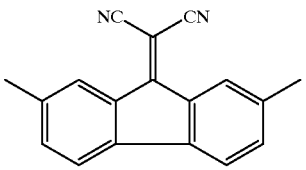 |
| (A-25) | 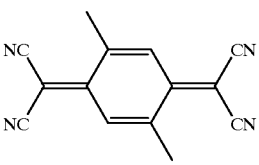 |
| (A-26) | 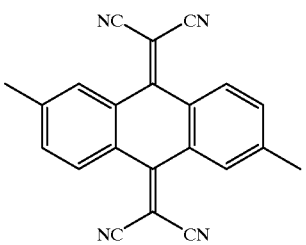 |
| (A-27) | 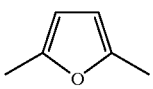 |
| (A-28) | 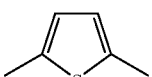 |
| (A-29) | 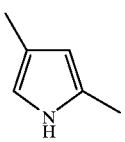 |
| (A-30) | 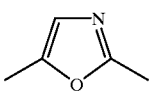 |
| (A-31) | 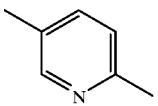 |

TABLE 1-continued
| Divalent group | Chemical structure (—A—) |
|---|---|
| (A-32) | 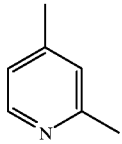 |
| (A-33) | 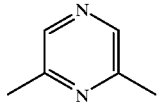 |
| (A-34) | 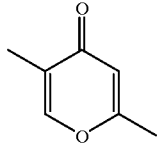 |
| (A-35) | 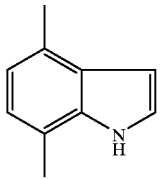 |
| (A-36) | 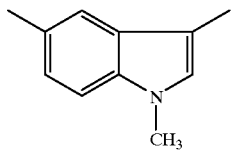 |
| (A-37) | 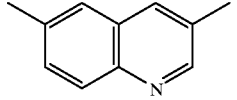 |
| (A-38) | 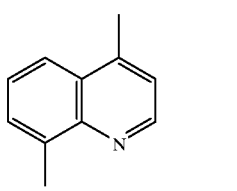 |
| (A-39) | 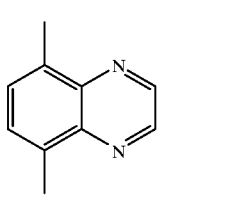 |
| (A-40) | 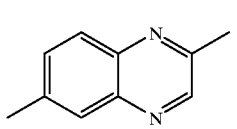 |

TABLE 1-continued
| Divalent group | Chemical structure (—A—) |
|---|---|
| (A-41) | 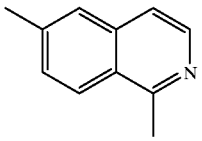 |
| (A-42) | 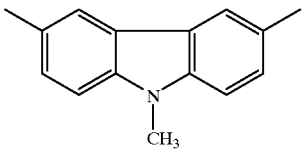 |
| (A-43) | 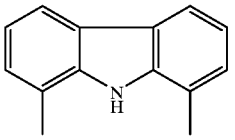 |
| (A-44) | 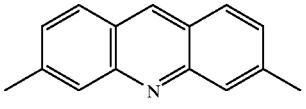 |
| (A-45) | 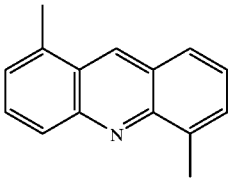 |
| (A-46) | 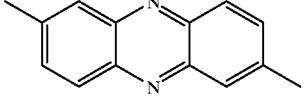 |
| (A-47) | 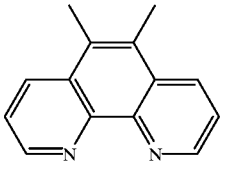 |
| (A-48) | 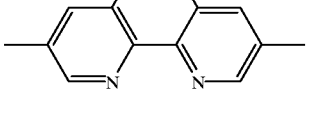 |
| (A-49) | 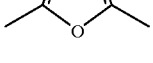 |
| (A-50) | 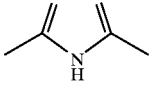 |

TABLE 1-continued
| Divalent group | Chemical structure (—A—) |
|---|---|
| (A-51) | 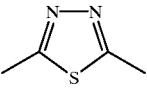 |
| (A-52) | 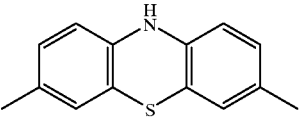 |
| (A-53) | 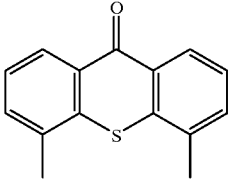 |
| (A-54) | 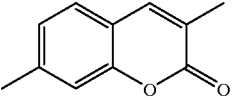 |
| (A-55) | 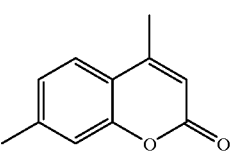 |
| (A-56) | 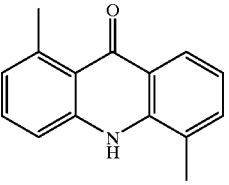 |
| (A-57) | 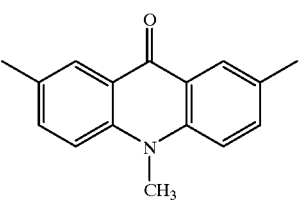 |
| (A-58) | 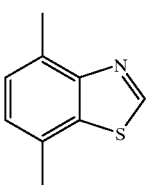 |
| (A-59) | 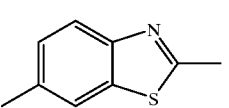 |

TABLE 1-continued

| Divalent group | Chemical structure (—A—) |
|---|---|
| (A-60) | benzobisthiazole-2,6-diyl |
| (A-61) | 9-ethyl-carbazole-2,7-diyl |
| (A-62) | dibenzothiophene-S,S-dioxide-3,7-diyl |
| (A-63) | 4-(dicyanomethylene)-2,6-dimethyl-4H-pyran-diyl |
| (A-64) | 4,4'-biphenylene |
| (A-65) | —(C₆H₄)₆— (poly-p-phenylene, n=6) |
| (A-66) | —(C₆H₄)₁₀— (poly-p-phenylene, n=10) |
| (A-67) | 4,4'-binaphthalene-diyl |
| (A-68) | 4,4'-methylenebis(phenylene) |
| (A-69) | 4,4'-(hexafluoroisopropylidene)bis(phenylene) |

TABLE 1-continued
| Divalent group | Chemical structure (—A—) |
|---|---|
| (A-70) | 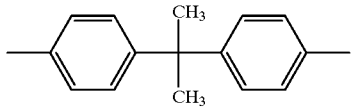 |
| (A-71) | 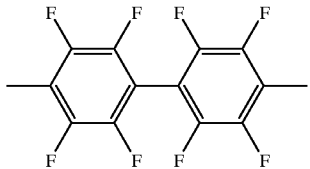 |
| (A-72) | 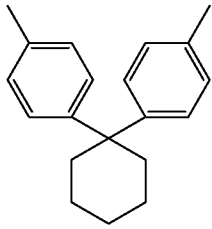 |
| (A-73) | 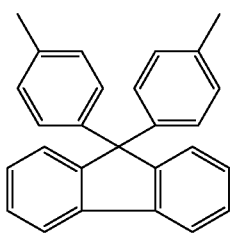 |
| (A-74) | 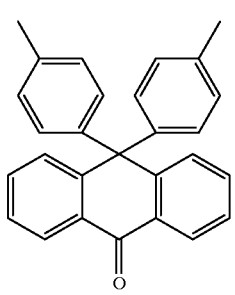 |
| (A-75) | 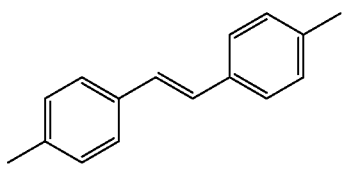 |
| (A-76) | 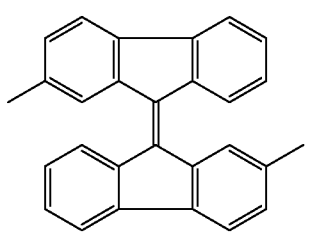 |

TABLE 1-continued
| Divalent group | Chemical structure (—A—) |
|---|---|
| (A-77) | 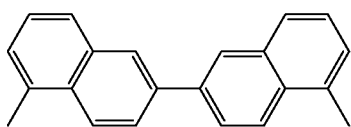 |
| (A-78) | 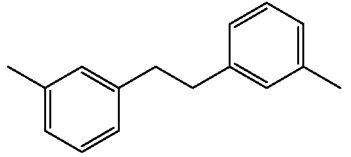 |
| (A-79) | 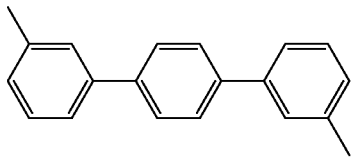 |
| (A-80) | 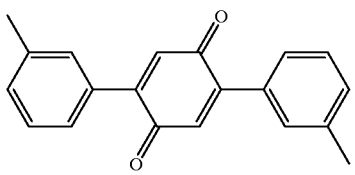 |
| (A-81) | 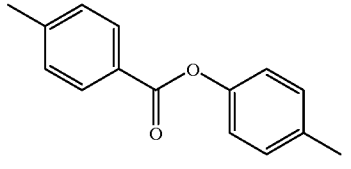 |
| (A-82) | 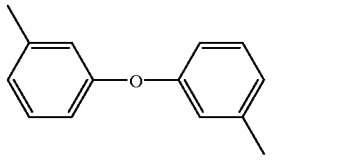 |
| (A-83) | 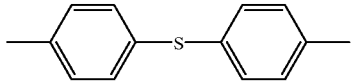 |
| (A-84) | 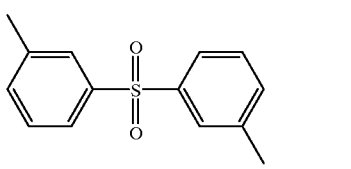 |
| (A-85) | 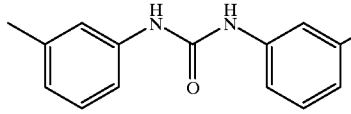 |

TABLE 1-continued

| Divalent group | Chemical structure (—A—) |
| --- | --- |
| (A-86) | |
| (A-87) | |
| (A-88) | |
| (A-89) | |
| (A-90) | |
| (A-91) | |
| (A-92) | |

TABLE 1-continued
| Divalent group | Chemical structure (—A—) |
|---|---|
| (A-93) | 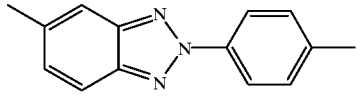 |
| (A-94) | 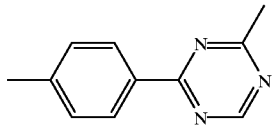 |
| (A-95) | 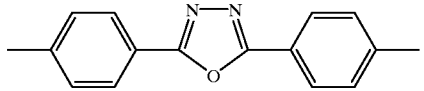 |
| (A-96) | 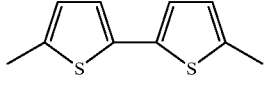 |
| (A-97) | 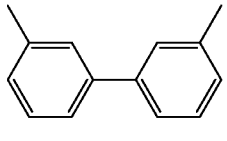 |
| (A-98) | 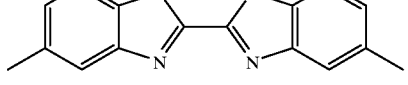 |
| (A-99) | 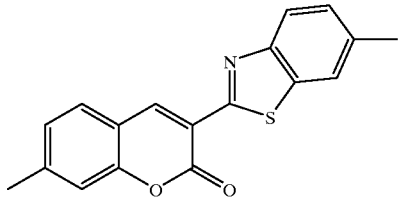 |
| (A-100) | 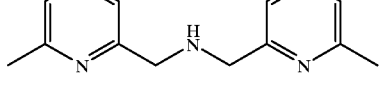 |
| (A-101) | 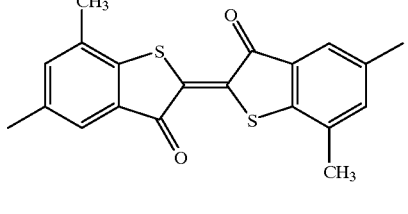 |
| (A-102) | 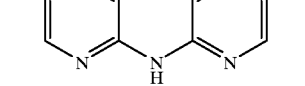 |

TABLE 1-continued
| Divalent group | Chemical structure (—A—) |
|---|---|
| (A-103) | 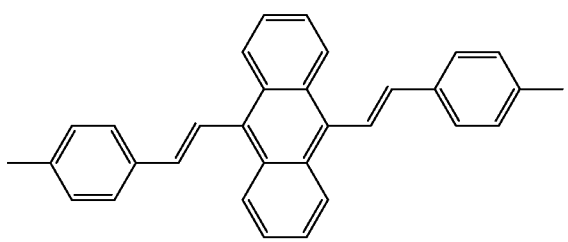 |
| (A-104) | 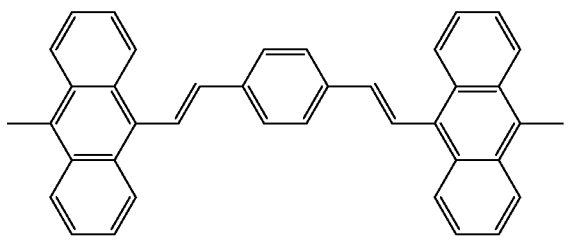 |
| (A-105) | 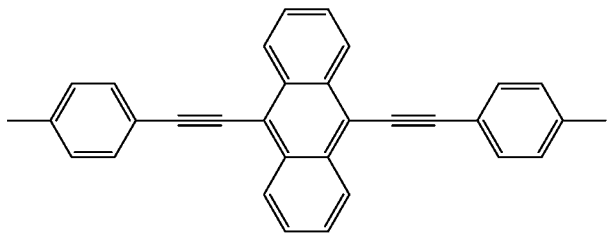 |
| (A-106) | 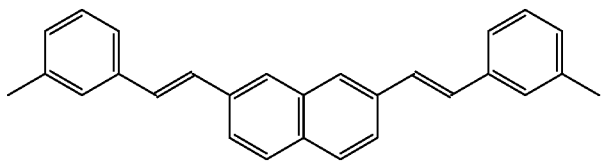 |
| (A-107) | 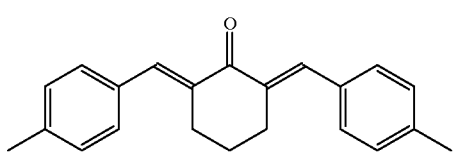 |
| (A-108) | 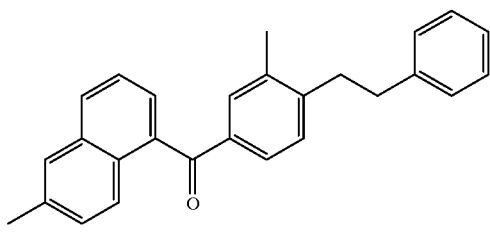 |
| (A-109) | 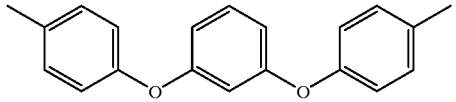 |

TABLE 1-continued

| Divalent group | Chemical structure (—A—) |
|---|---|
| (A-110) | |
| (A-111) | |
| (A-112) | |
| (A-113) | |
| (A-114) | |
| (A-115) | |
| (A-116) | |
| (A-117) | |
| (A-118) | |

TABLE 1-continued

| Divalent group | Chemical structure (—A—) |
| --- | --- |
| (A-119) | |
| (A-120) | |
| (A-121) | |
| (A-122) | |
| (A-123) | |
| (A-124) | |

TABLE 1-continued

| Divalent group | Chemical structure (—A—) |
|---|---|
| (A-125) | |
| (A-126) | |
| (A-127) | |
| (A-128) | |
| (A-129) | |
| (A-130) | |
| (A-131) | |
| (A-132) | |

TABLE 1-continued

| Divalent group | Chemical structure (—A—) |
| --- | --- |
| (A-133) | |
| (A-134) | |
| (A-135) | |
| (A-136) | |
| (A-137) | |
| (A-138) | |

TABLE 1-continued
| Divalent group | Chemical structure (—A—) |
|---|---|
| (A-139) | 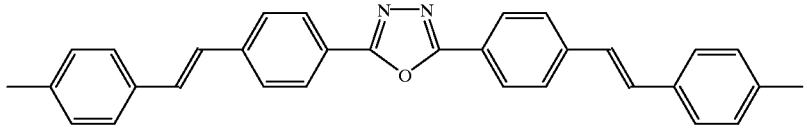 |
| (A-140) | 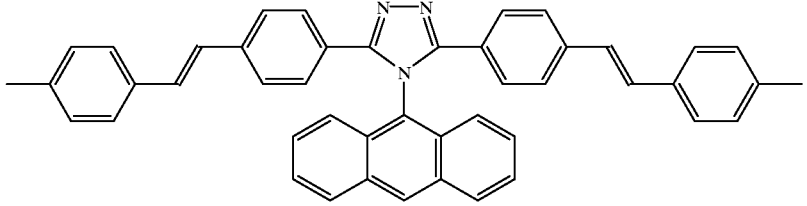 |
| (A-109) | 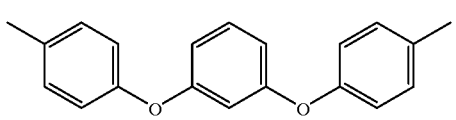 |
| (A-110) | 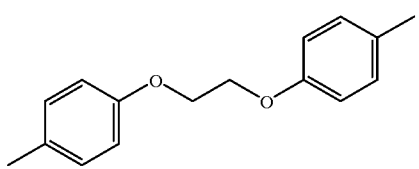 |
| (A-111) | 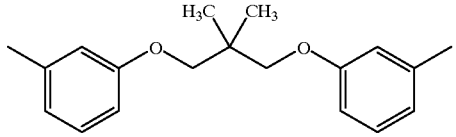 |
| (A-112) | 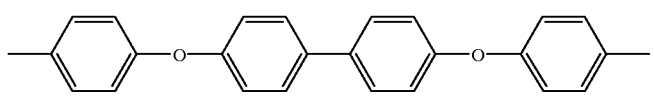 |
| (A-113) | 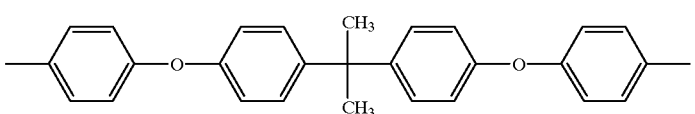 |
| (A-114) | 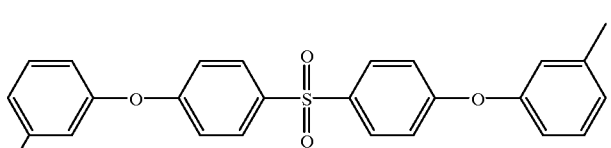 |
| (A-115) | 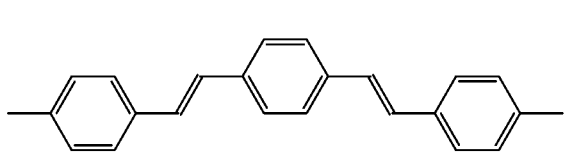 |

TABLE 1-continued

| Divalent group | Chemical structure (—A—) |
|---|---|
| (A-116) | 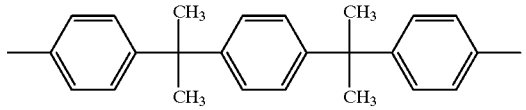 |

In the compound of the formula [1] in the present invention, each of $Ar^1$ to $Ar^4$ is independently a substituted or non-substituted divalent aromatic group or a substituted or non-substituted fused aromatic group.

Specific examples of $Ar^1$ to $Ar^4$ include divalent residues of substituted or non-substituted aromatic groups or fused aromatic groups such as benzene, toluene, xylene, ethylbenzene, naphthalene, anthracene, phenanthrene, fluorene, pyrene, chrysene, naphthacene, perylene and azulene. In the compound of the formula [1], [4] or [5], each of $R^1$ to $R^{20}$ is independently a hydrogen atom, a halogen atom, a substituted or non-substituted alkyl group, a substituted or non-substituted alkoxy group, a substituted or non-substituted aryl group or a substituted or non-substituted amino group.

Specific examples of the substituent on A or $Ar^1$ to $Ar^4$, or specific examples of $R^1$ to $R^{20}$, include halogen atoms such as fluorine, chlorine, bromine and iodine, substituted or non-substituted alkyl groups such as methyl, ethyl, propyl, butyl, sec-butyl, tert-butyl, pentyl, hexyl, heptyl, octyl, stearyl, 2-phenylisopropyl, trichloromethyl, trifluoromethyl, benzyl, α-phenoxybenzyl, α,α-dimethylbenzyl, α,α-methylphenylbenzyl, α,α-ditrifluoromethylbenzyl, triphenylmethyl and α-benzyloxybenzyl, substituted or non-substituted alkoxy groups such as methoxy, ethoxy, propoxy, n-butoxy, t-butoxy, n-octyloxy, t-octyloxy, 1,1,1-tetrafluoroethoxy, phenoxy, benzyloxy and octylphenoxy, substituted or non-substituted aryl groups such as phenyl, 2-methylphenyl, 3-methylphenyl, 4-methylphenyl, 4-ethylphenyl, biphenyl, 4-methylbiphenyl, 4-ethylbiphenyl, 4-cyclohexylbiphenyl, terphenyl, 3,5-dichlorophenyl, naphthyl, 5-methylnaphthyl, anthryl and pyrenyl, and substituted or non-substituted amino groups such as amino, dimethylamino, diethylamino, phenylmethylamino, diphenylamino, ditolylamino and dibenzylamino. Further, adjacent substituents may bond to each other to form a substituted or non-substituted cyclopentene, cyclohexene, phenyl, naphthalene, anthracene, pyrene, fluorene, furan, thiophene, pyrrol, oxazole, thiazole, imidazole, pyridine, pyrazine, pyrroline, pyrazoline, indole, quinoline, quinoxaline, xanthene, carbazole, acridine or phenanthroline ring.

In the compound of the formula [1] or [4] in the present invention, each of $X^1$ to $X^4$ is independently —O—, —S—, >C=O, >SO$_2$, —($C_xH_{2x}$)—O—($C_yH_{2y}$)— (in which each of x and y is an integer of 0 to 20, while x+y=0 in no case), a substituted or non-substituted alkylidene group having at least 2 carbon atoms, a substituted or non-substituted alkylene group having at least 2 carbon atoms or a substituted or non-substituted divalent alicyclic residue. In the compound of the formula [5] in the present invention, each of $Y^1$ to $Y^8$ is a substituted or non-substituted alkyl group having 1 to 20 carbon atoms or a substituted or non-substituted aromatic group having 6 to 16 carbon atoms. Further, groups of $Y^1$ and $Y^2$, $Y^3$ and $Y^4$, $Y^5$ and $Y^6$, or $Y^7$ and $Y^8$ may form a substituted or non-substituted alicyclic group having 5 to 7 carbon atoms. Specific examples of the alkyl group and the aromatic group include those alkyl groups and aromatic groups specified with regard to the above $R^1$ to $R^{20}$. Further, the substituted or non-substituted alicyclic group which may be formed include cyclopentyl, cyclohexyl, 4-methylcyclohexyl and cycloheptyl.

The following Table 2 specifically shows typical examples of groups bonding to a nitrogen atom of the compound of the formula [1], [4] or [5] (e.g., portion of substituted or non-substituted benzene ring —$X^n$—$Ar^n$— in the formula [1]), while the present invention shall not be limited by these examples.

TABLE 2

| Monovalent group | Chemical structure |
|---|---|
| (B-1) | 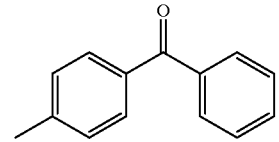 |
| (B-2) | 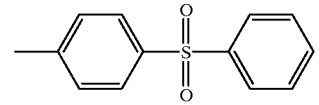 |
| (B-3) | 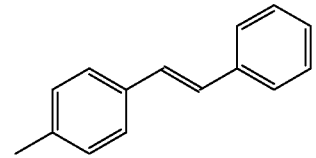 |
| (B-4) | 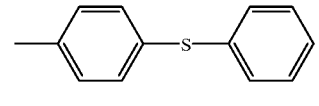 |
| (B-5) | 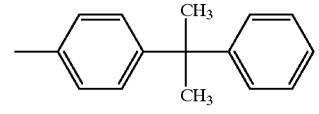 |
| (B-6) | 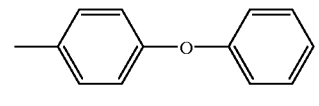 |

TABLE 2-continued

| Monovalent group | Chemical structure |
|---|---|
| (B-7) | 4-methylphenyl-CH$_2$-O-phenyl |
| (B-8) | 4-methylphenyl-O-CH$_2$-phenyl |
| (B-9) | 4-methylphenyl-CH$_2$-O-CH$_2$-phenyl |
| (B-10) | 4-methylphenyl-O-(C$_8$H$_{16}$)-phenyl |
| (B-11) | 4-methylphenyl-C(CF$_3$)$_2$-phenyl |
| (B-12) | 3-methylphenyl-O-phenyl |
| (B-13) | 4-methylphenyl-CH$_2$CH$_2$-phenyl |
| (B-14) | 3-methylphenyl-C(CH$_3$)$_2$-phenyl |
| (B-15) | 4-methylphenyl-C(phenyl)(cyclohexyl-fused)-phenyl |
| (B-16) | 4-methylphenyl-C(CH$_3$)(phenyl)-phenyl |
| (B-17) | 4-methylphenyl-C(phenyl)$_3$ |
| (B-18) | 4-methylphenyl-C(C$_8$H$_{17}$)$_2$-phenyl |
| (B-19) | 3,5-dimethylphenyl-C(CH$_3$)$_2$-phenyl |
| (B-20) | 4-methylnaphthyl-C(CH$_3$)$_2$-phenyl |
| (B-21) | 4-methyl-tetrafluorophenyl-C(CF$_3$)$_2$-pentafluorophenyl |
| (B-22) | 4-methylphenyl-O-(pentachlorophenyl) |

TABLE 2-continued

| Monovalent group | Chemical structure |
| --- | --- |
| (B-23) | [3-chloro-5-methylphenyl phenyl ether] |
| (B-24) | [4-(2-(naphthalen-2-yl)propan-2-yl)phenyl] |
| (B-25) | [4-(4-phenylcyclohexyl)phenyl] |
| (B-26) | [4-(2-(4-(2-methylpropan-2-yl)phenyl)propan-2-yl)phenyl] |
| (B-27) | [4-(4-phenylphenoxy)phenyl] |
| (B-28) | [4-(4-methoxyphenoxy)phenyl] |
| (B-29) | [4-(2-(4-(diethylamino)phenyl)propan-2-yl)phenyl] |
| (B-30) | [3-methylphenyl-(9-ethylcarbazol-3-yl)dimethylmethane] |

The compounds of the present invention have a high glass transition point and a high melting point due to their bulky groups having a large molecular weight. Further, compounds in which adjacent groups of $R^1$ to $R^{20}$ together form an aromatic ring have a further increased glass transition point and a further increased melting point. Therefore, the compounds of the present invention have improved durability (heat resistance) against Joule's heat which is generated in an organic layer, between organic layers or between an organic layer and a metal electrode when electric field light emission is effected. When used as a light-emitting material in an organic EL device, the compounds of the present invention exhibit a high light emission brightness and is advantageous for continuous light emission for a long period of time.

In general, the compound of the formula [1], [4] or [5] in the present invention can be synthesized by the following method. A dihalide of a divalent residue corresponding to A in the general formula [1], [4] or [5], a secondary amine derivative having a structure in which a bond between a nitrogen atom and A in the general formula [1], [4] or [5] is replaced with hydrogen, potassium carbonate and a catalyst are allowed to react in a solvent, to form a compound of the formula [1], [4] or [5]. Some compounds can be synthesized by using a dicarbonyl compound having the structure of A in place of the dihalide having the structure of A. The above potassium carbonate may be replaced with sodium carbonate, potassium hydroxide, sodium hydroxide or aqueous ammonia. The catalyst can be selected from powdered copper, cuprous chloride, stannous chloride, pyridine, aluminum trichloride or titanium tetrachloride. The solvent is selected from benzene, toluene or xylene. The above synthesis method is one example, and the method of synthesizing the compounds of the present invention shall not be limited thereto.

The following Table 3 specifically shows typical examples of the light-emitting material of the present invention, while the present invention shall not be limited by these Examples.

TABLE 3

| compound | Chemical structure |
|---|---|
| (1) | 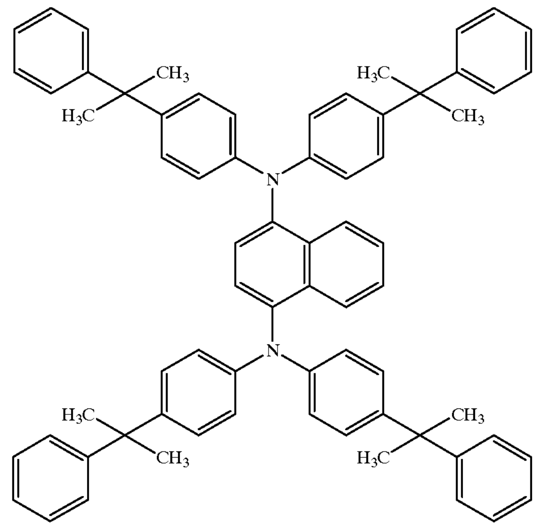 |

TABLE 3-continued

| compound | Chemical structure |
|---|---|
| (2) | 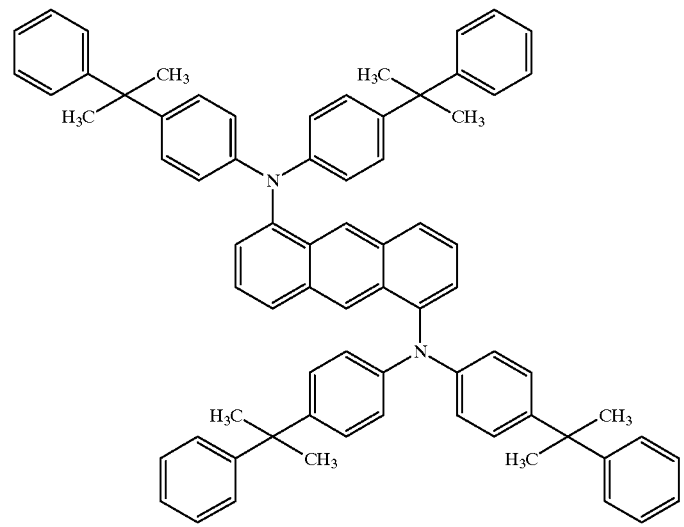 |
| (3) | 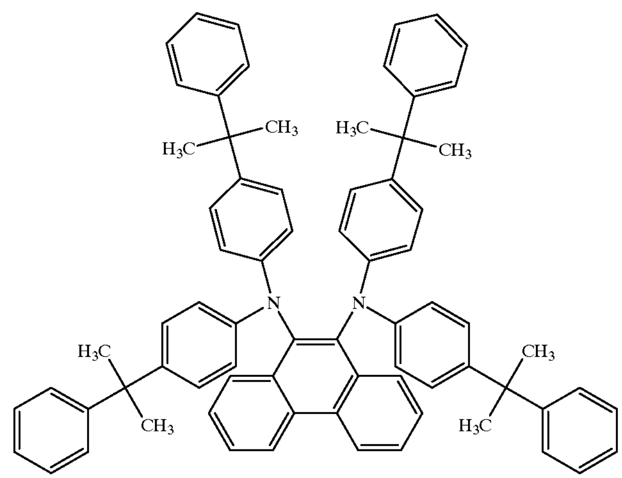 |

TABLE 3-continued

| compound | Chemical structure |
|---|---|
| (4) | 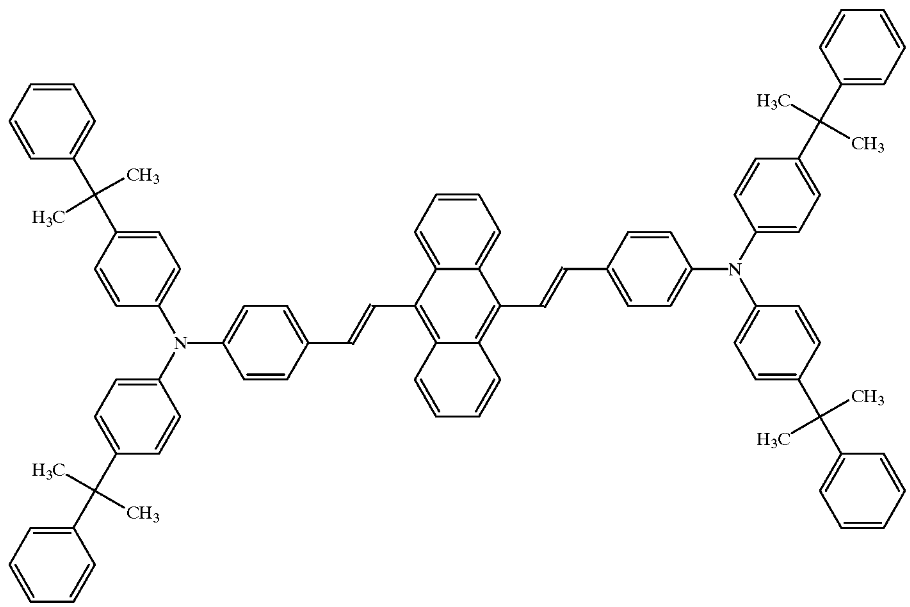 |

TABLE 3-continued
| compound | Chemical structure |
|---|---|
| (5) | 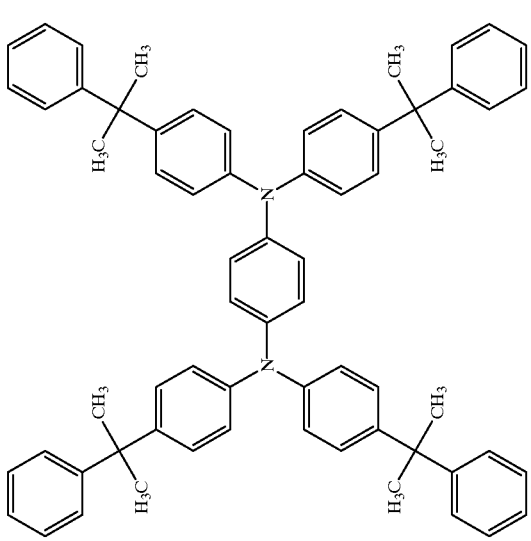 |

TABLE 3-continued
| compound | Chemical structure |
|---|---|
| (6) | 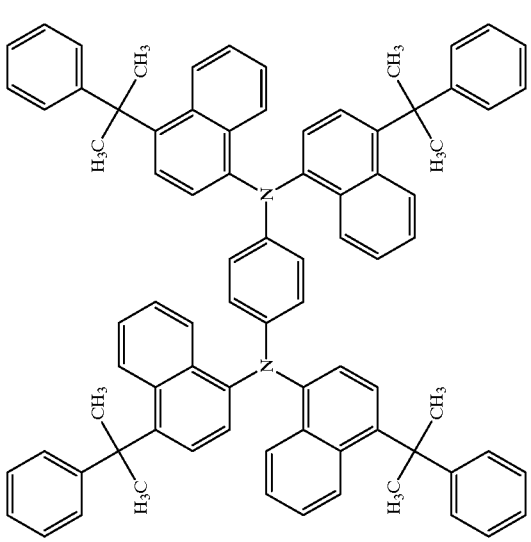 |

TABLE 3-continued
| compound | Chemical structure |
|---|---|
| (7) | 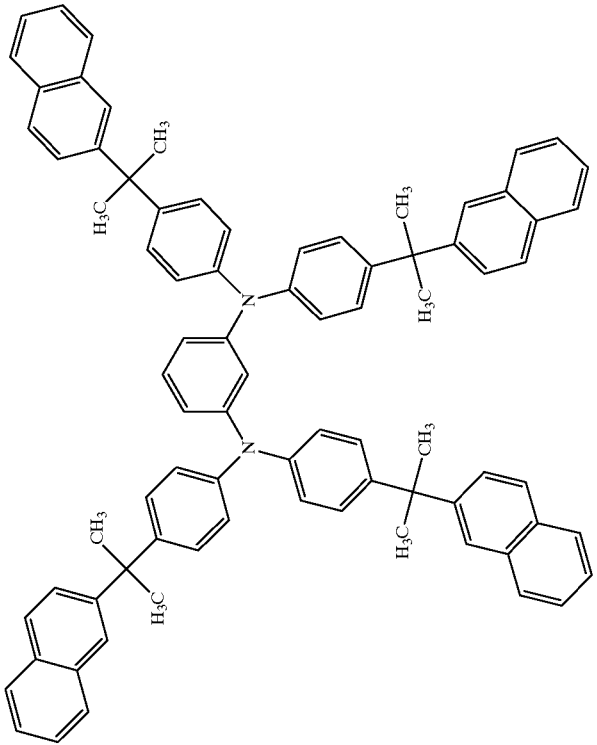 |

TABLE 3-continued

| compound | Chemical structure |
|---|---|
| (8) | 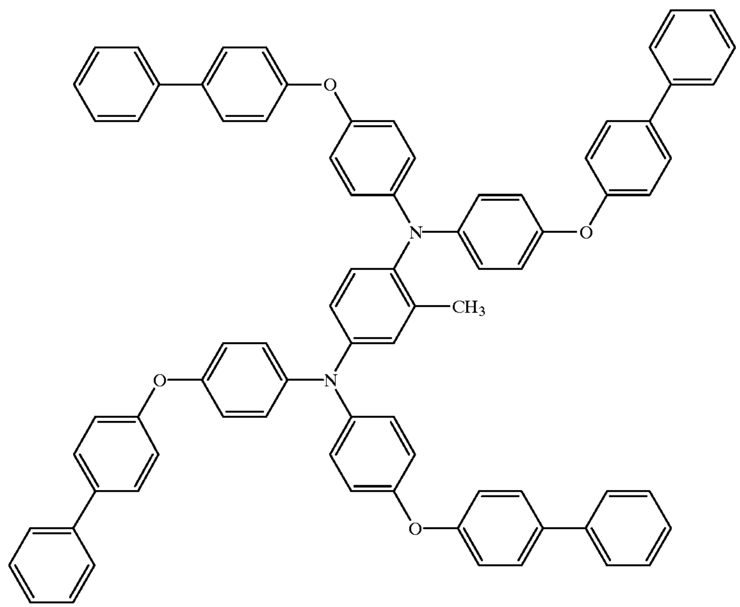 |

TABLE 3-continued
| compound | Chemical structure |
|---|---|
| (9) | 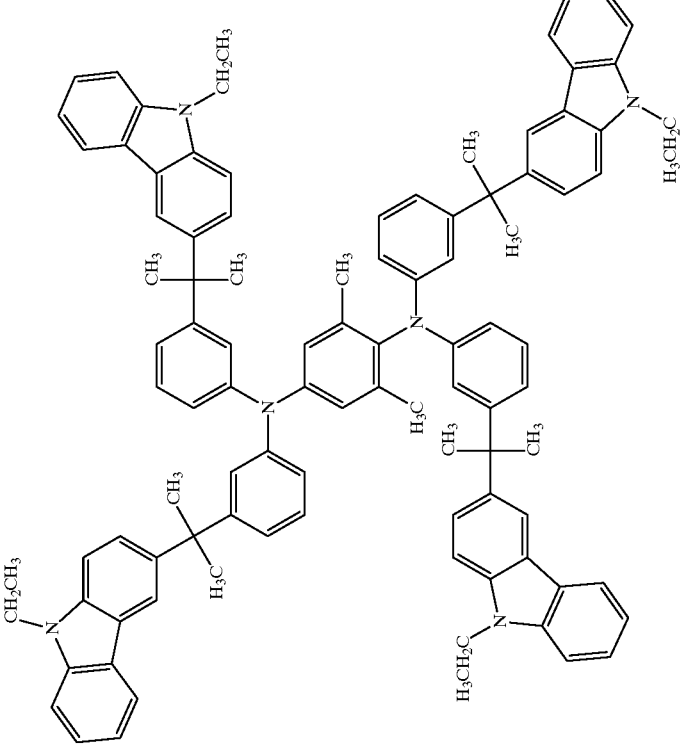 |

TABLE 3-continued
| compound | Chemical structure |
|---|---|
| (10) | 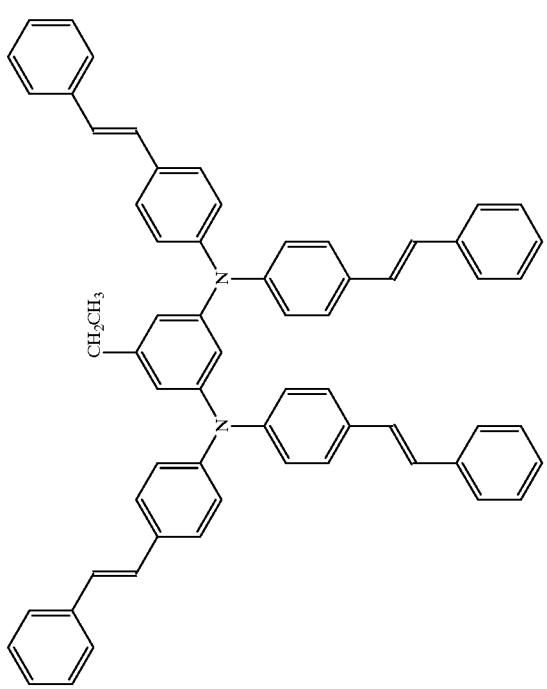 |
| (11) | 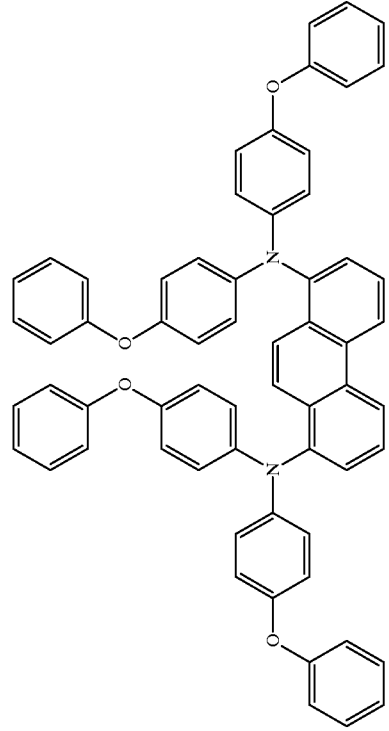 |

TABLE 3-continued

| compound | Chemical structure |
|---|---|
| (12) | 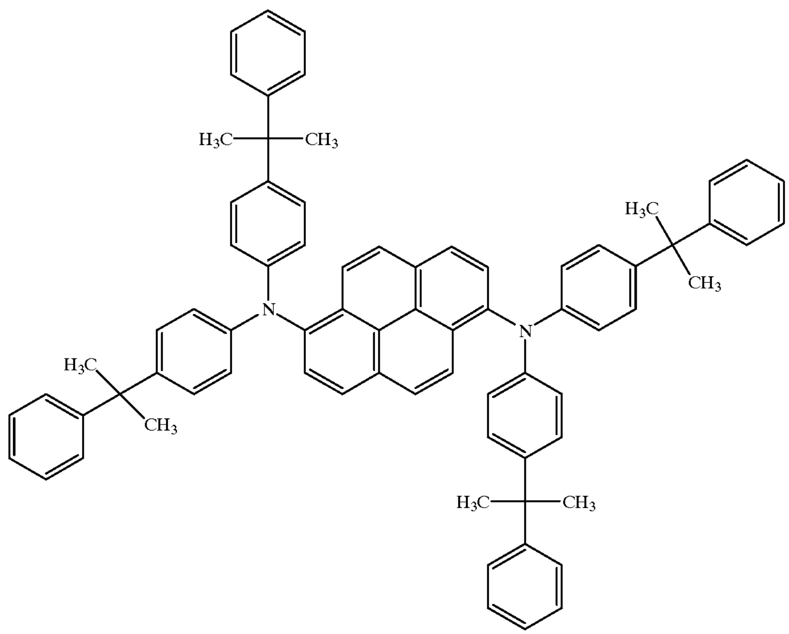 |
| (13) | 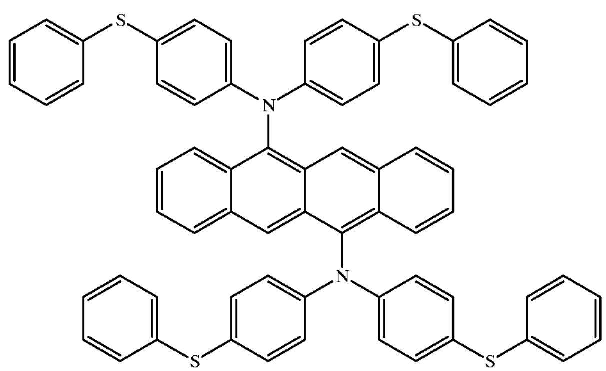 |

TABLE 3-continued
| compound | Chemical structure |
|---|---|
| (14) | 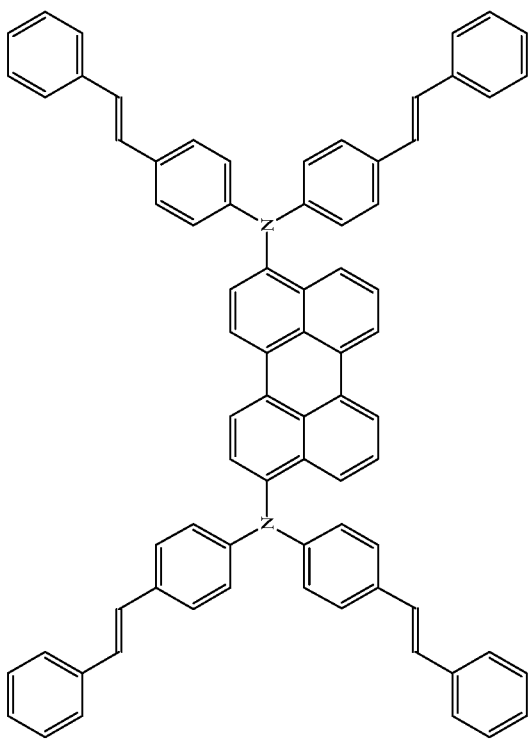 |

TABLE 3-continued
| compound | Chemical structure |
|---|---|
| (15) | 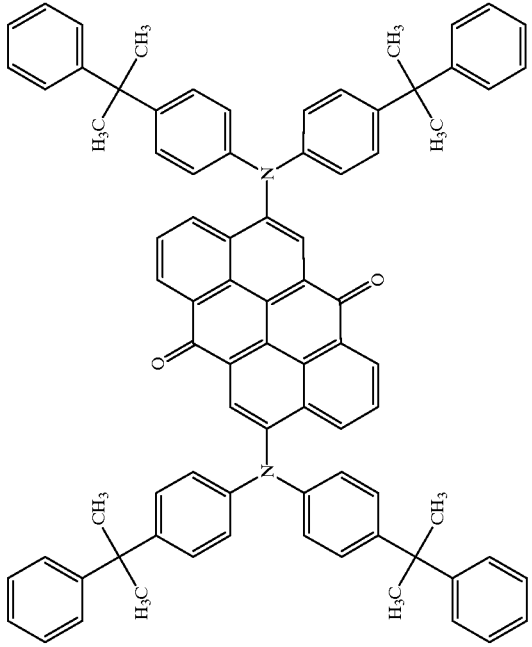 |

TABLE 3-continued
| compound | Chemical structure |
|---|---|
| (16) | 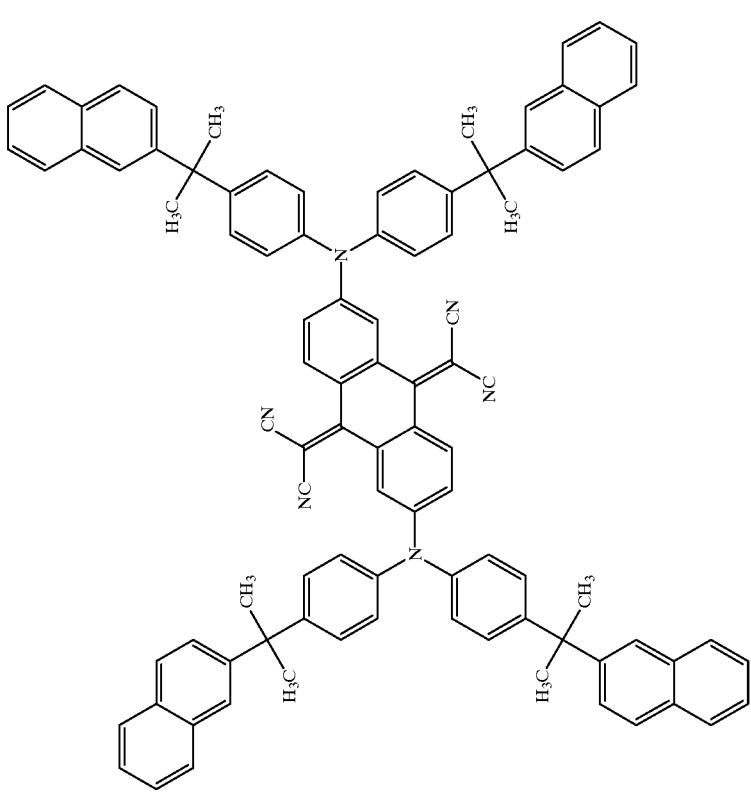 |

TABLE 3-continued
| compound | Chemical structure |
|---|---|
| (17) | 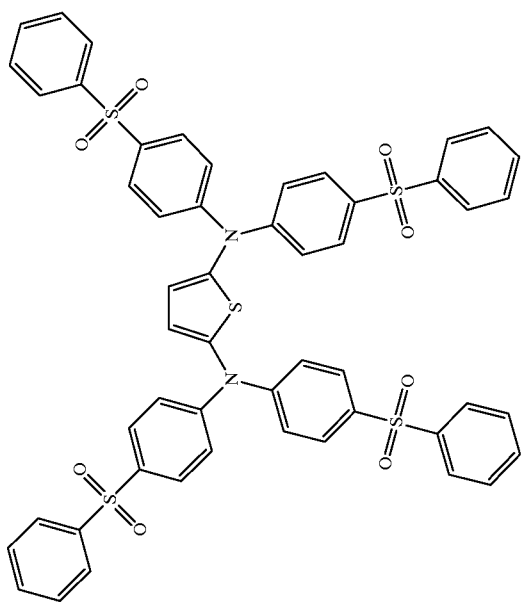 |

TABLE 3-continued
| compound | Chemical structure |
|---|---|
| (18) | 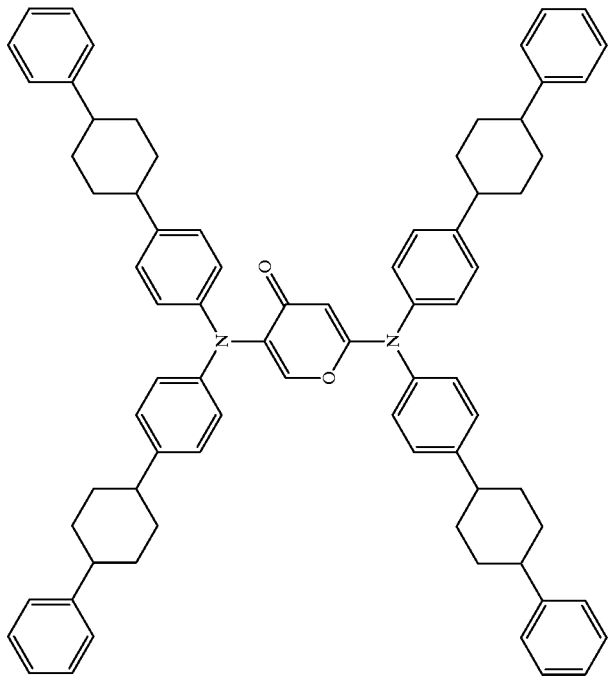 |
| (19) | 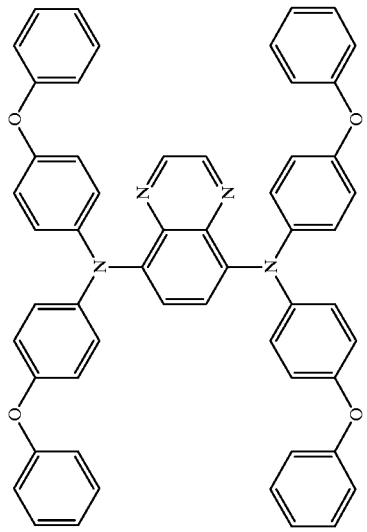 |

TABLE 3-continued

| compound | Chemical structure |
|---|---|
| (20) | 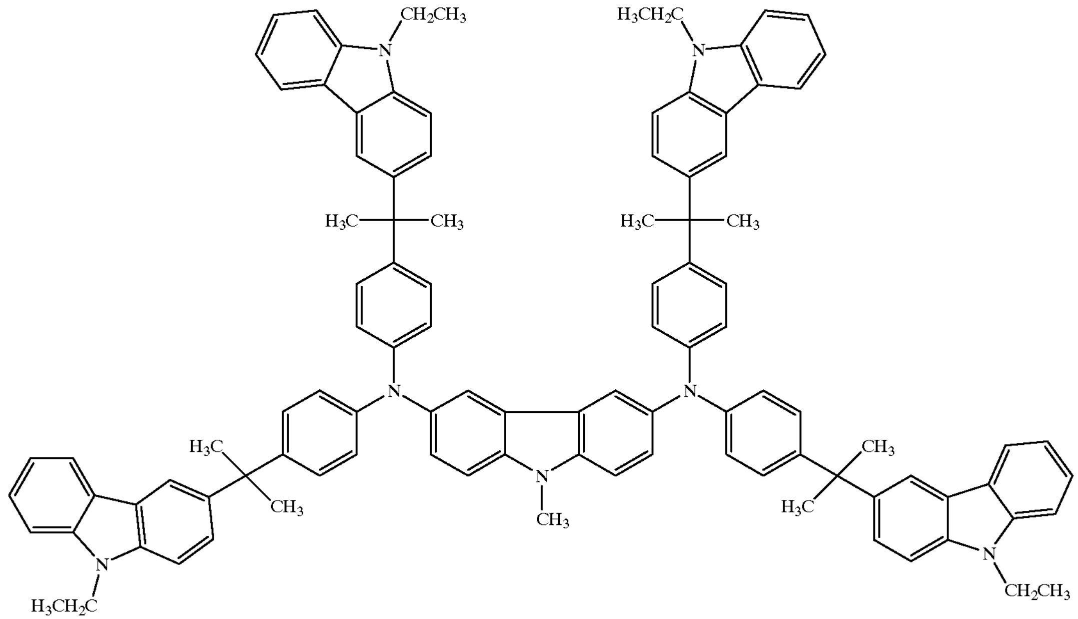 |

TABLE 3-continued
| compound | Chemical structure |
|---|---|
| (21) | 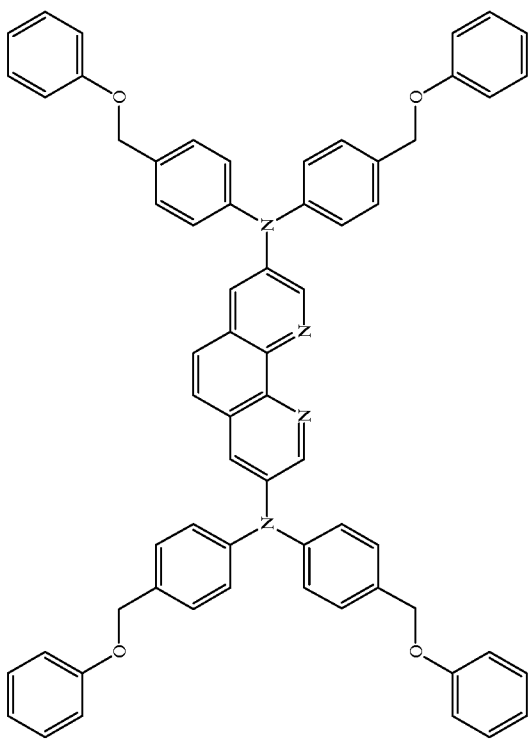 |

TABLE 3-continued

| compound | Chemical structure |
|---|---|
| (22) | ![structure: 2,5-bis[bis(4-(8-phenyloctyloxy)phenyl)amino]-1,3,4-oxadiazole] |

TABLE 3-continued

| compound | Chemical structure |
|---|---|
| (23) | 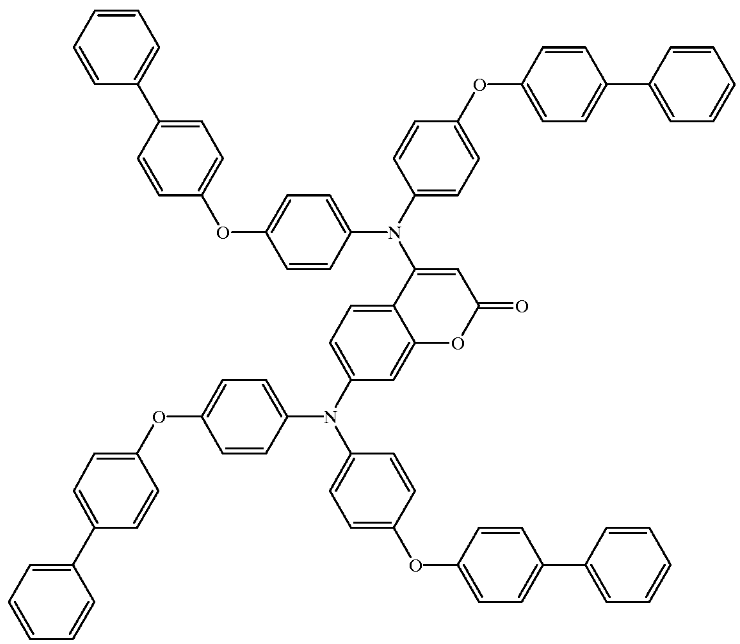 |

TABLE 3-continued
| compound | Chemical structure |
|---|---|
| (24) | 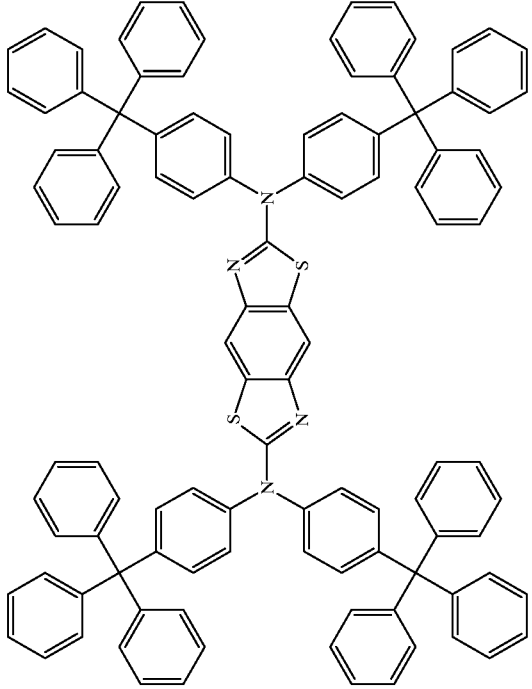 |
| (25) | 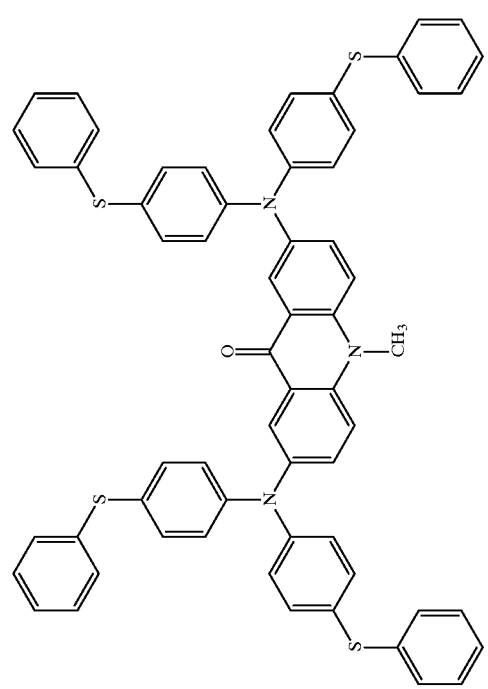 |

TABLE 3-continued
| compound | Chemical structure |
| --- | --- |
| (26) | 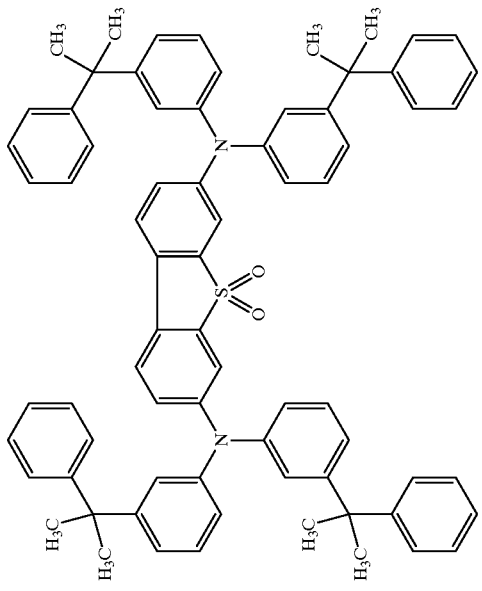 |
| (27) | 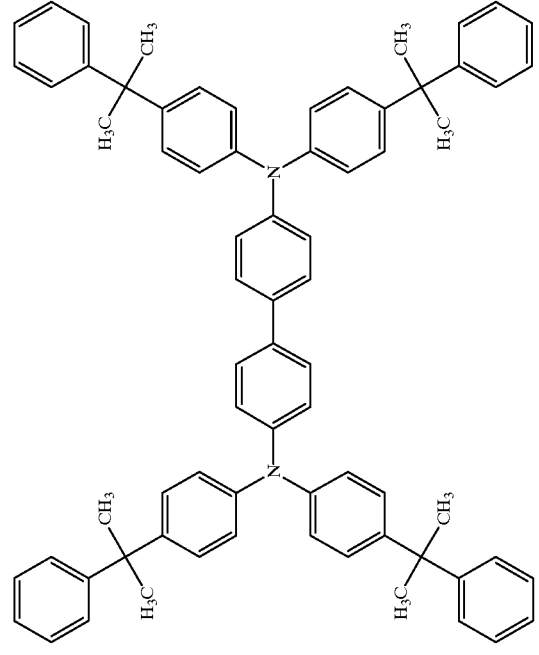 |

TABLE 3-continued
| compound | Chemical structure |
|---|---|
| (28) | 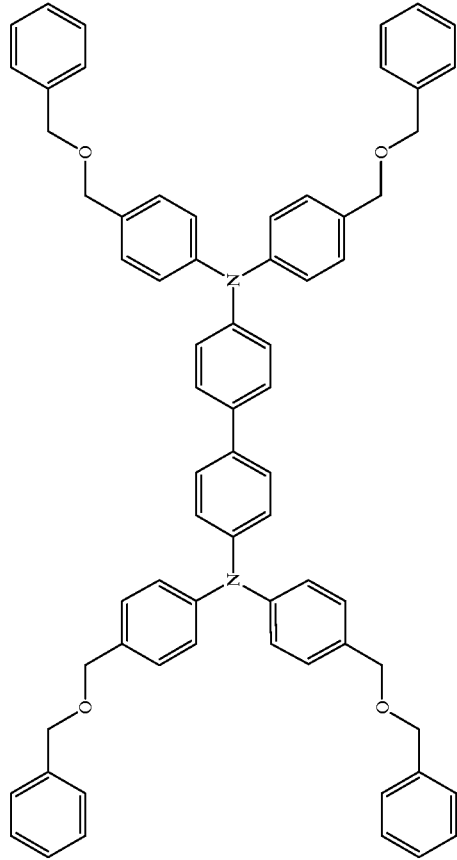 |
| (29) | 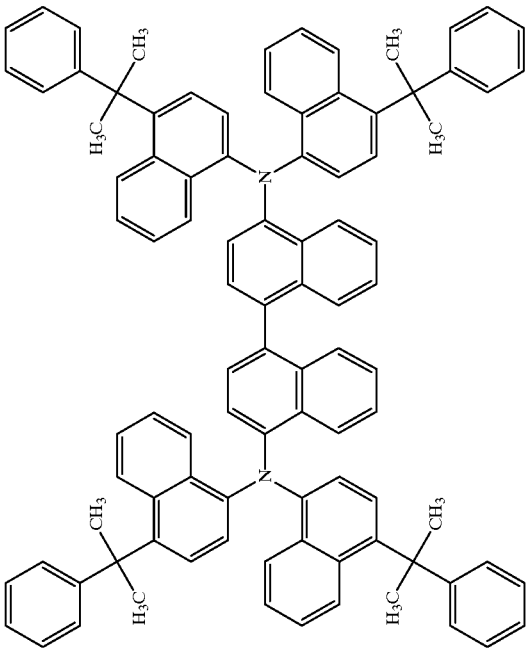 |

TABLE 3-continued

| compound | Chemical structure |
|---|---|
| (30) | 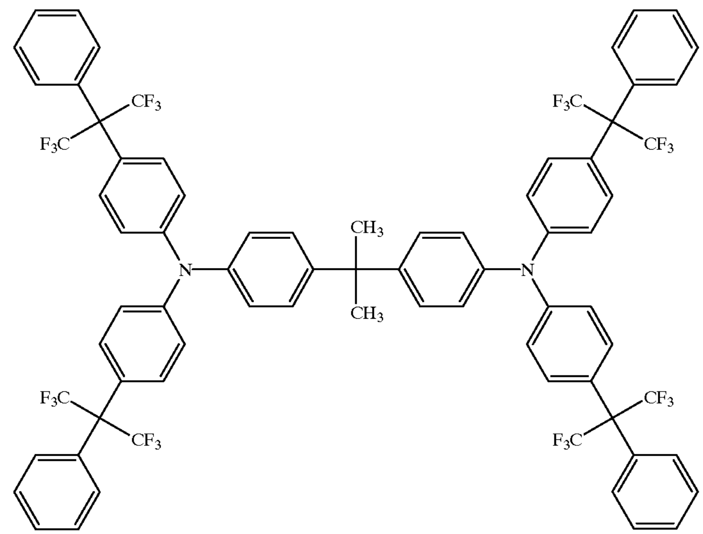 |
| (31) | 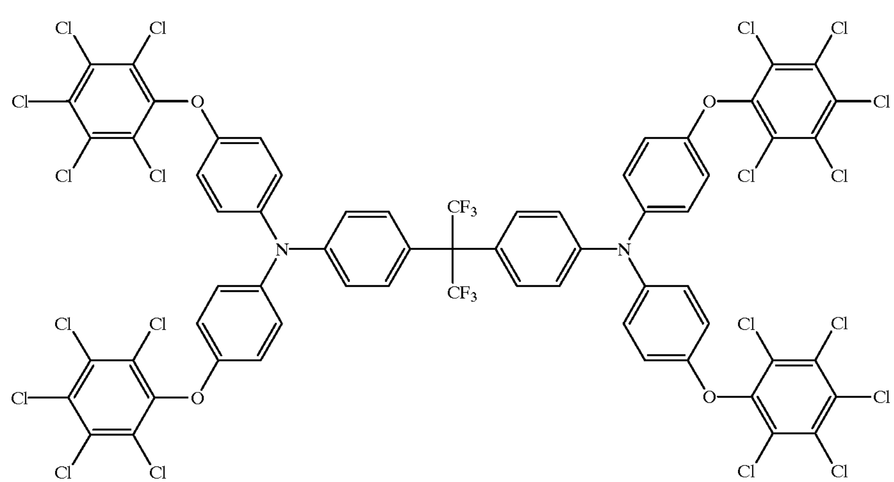 |

TABLE 3-continued
| compound | Chemical structure |
|---|---|
| (32) | 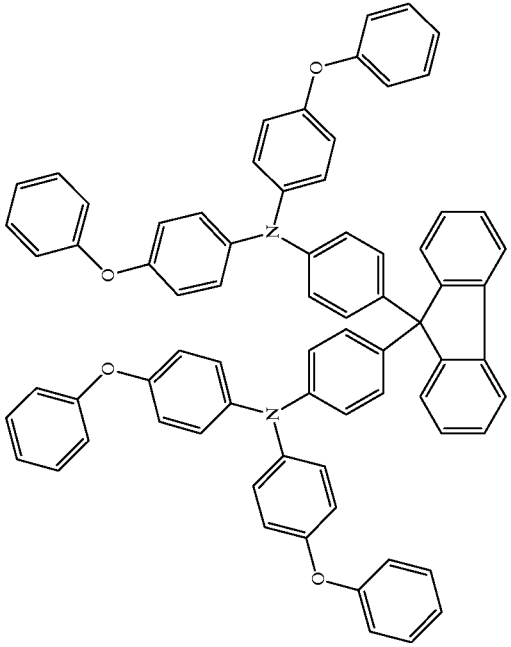 |

TABLE 3-continued
| compound | Chemical structure |
|---|---|
| (33) | 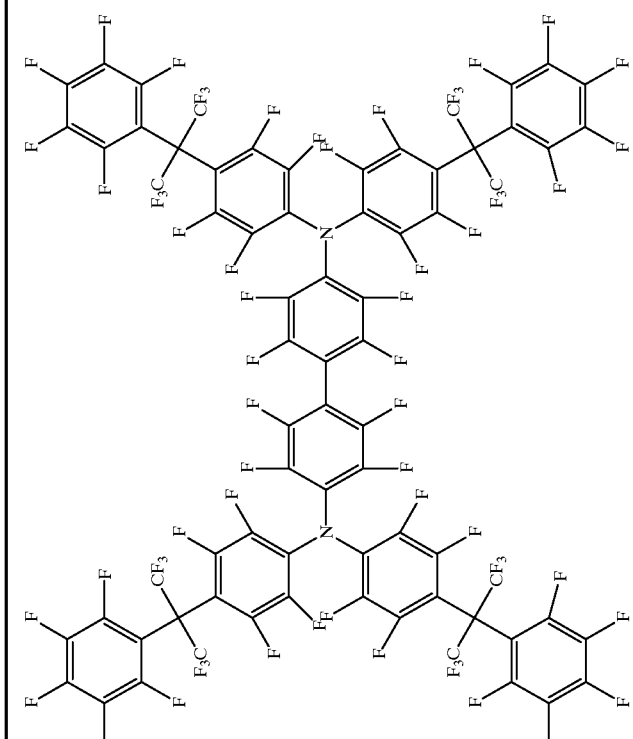 |

TABLE 3-continued
| compound | Chemical structure |
|---|---|
| (34) | 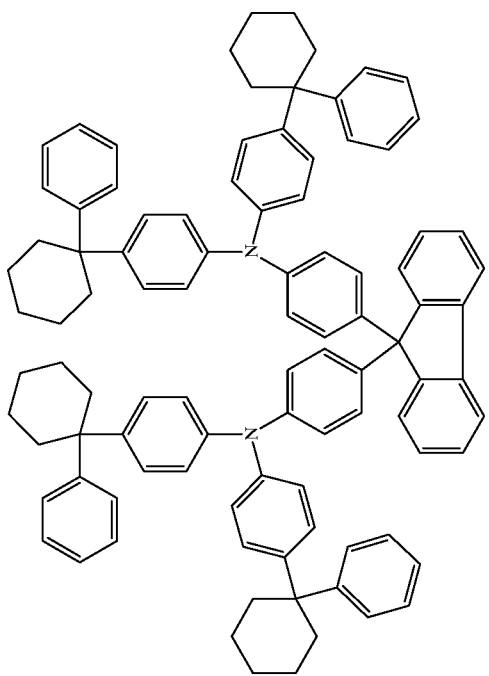 |

TABLE 3-continued
| compound | Chemical structure |
|---|---|
| (35) | 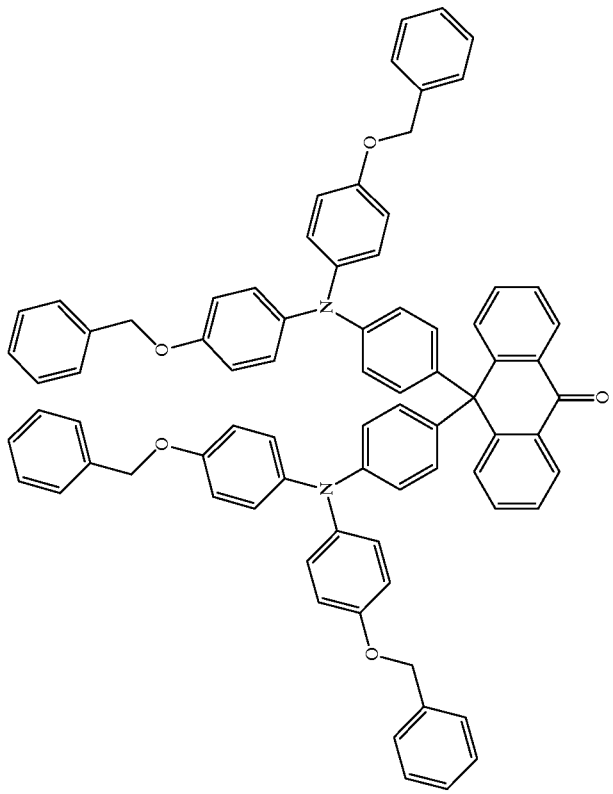 |

TABLE 3-continued
| compound | Chemical structure |
|---|---|
| (36) | 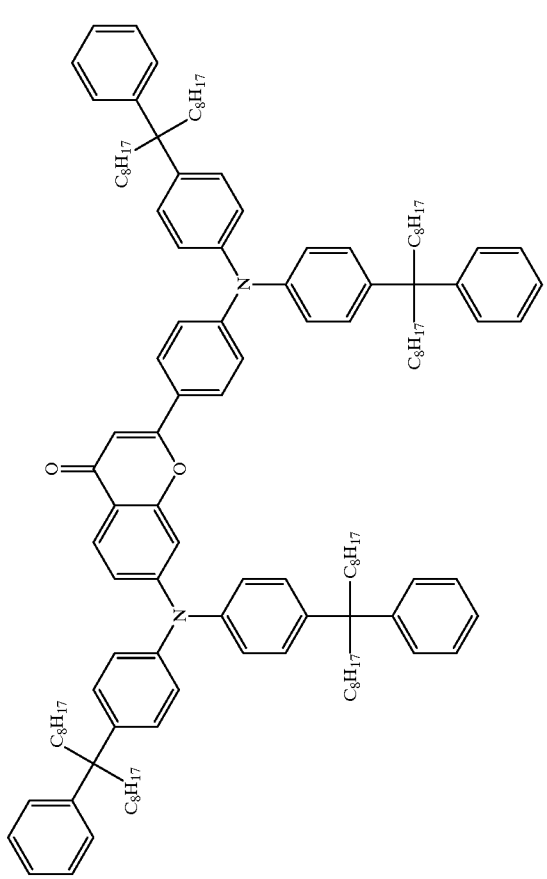 |

TABLE 3-continued

| compound | Chemical structure |
|---|---|
| (37) | 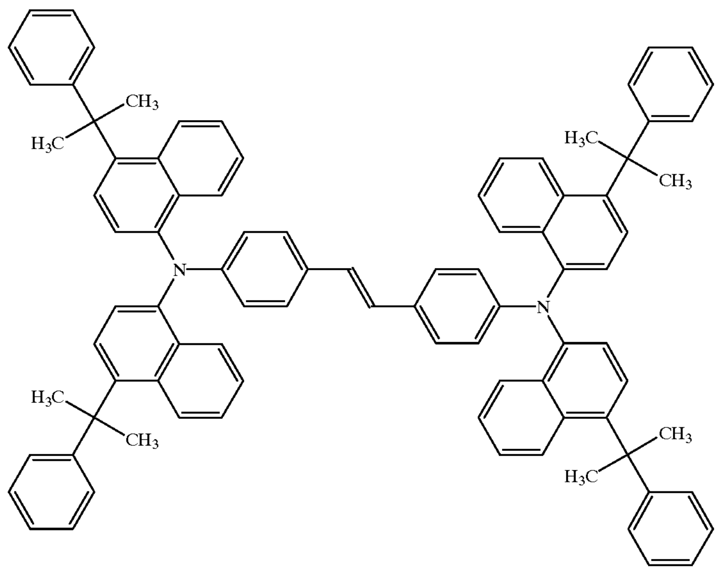 |

TABLE 3-continued
| compound | Chemical structure |
|---|---|
| (38) | 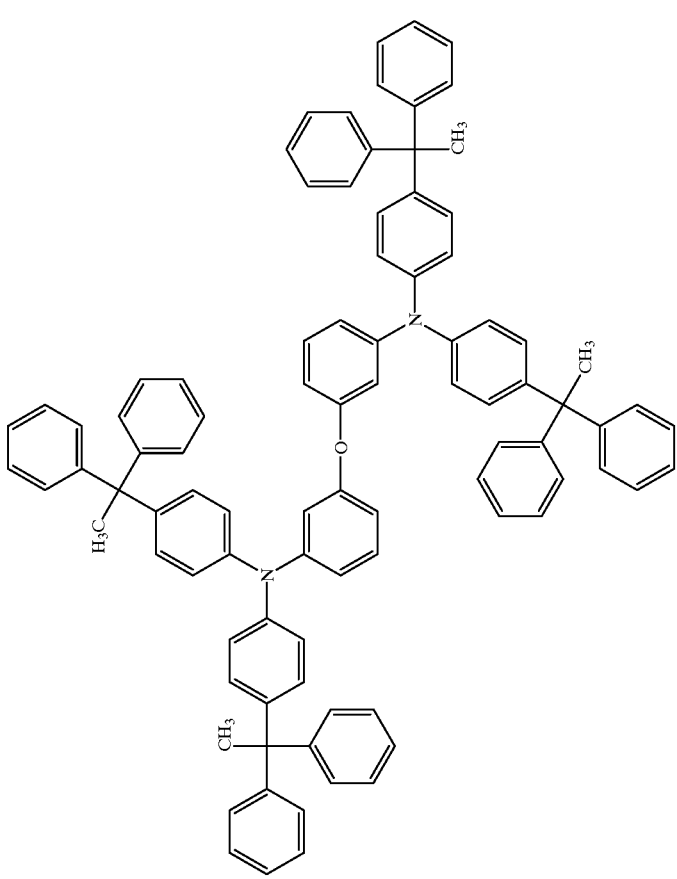 |

TABLE 3-continued
| compound | Chemical structure |
|---|---|
| (39) | 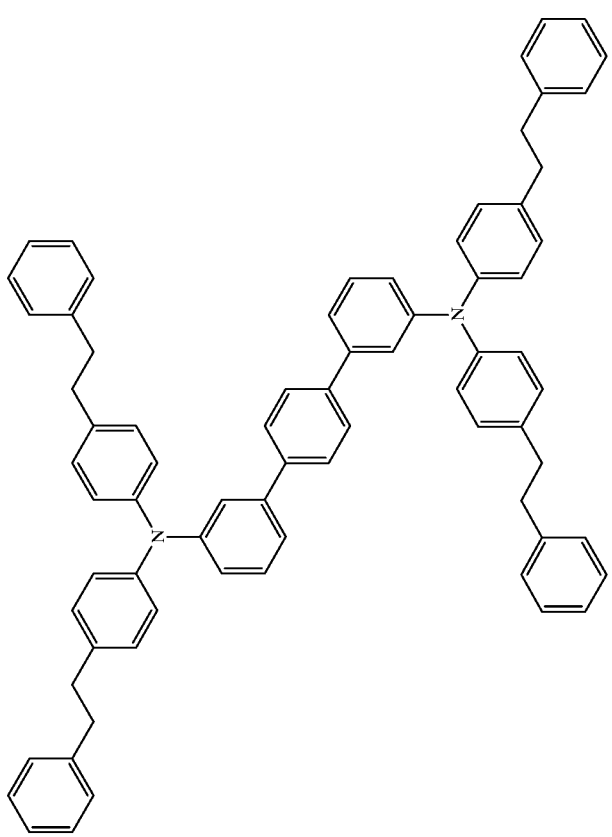 |

TABLE 3-continued
| compound | Chemical structure |
|---|---|
| (40) | 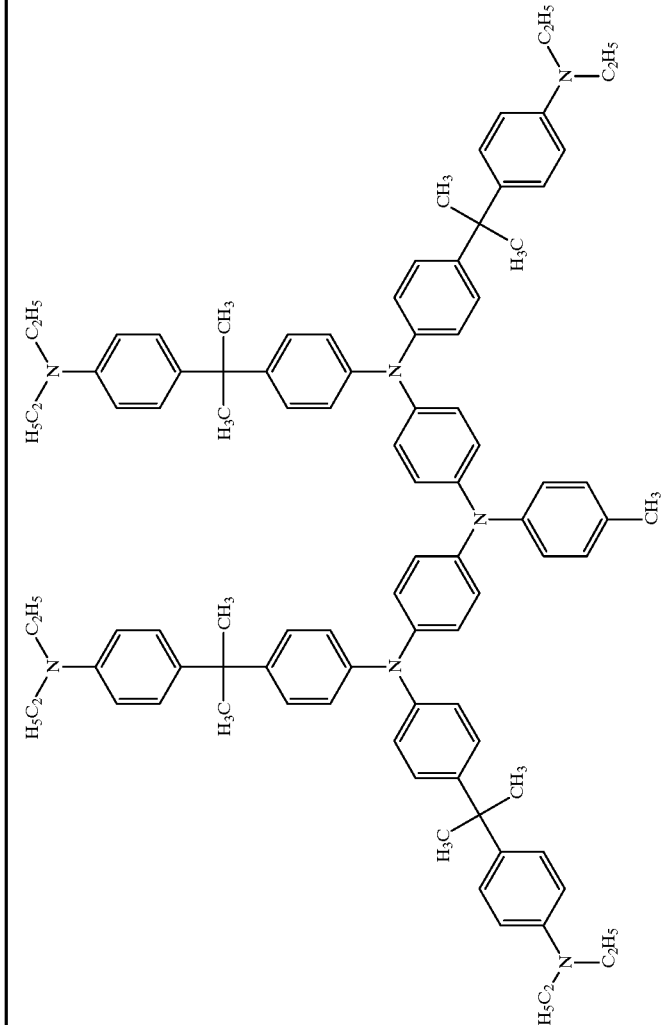 |
| (41) | 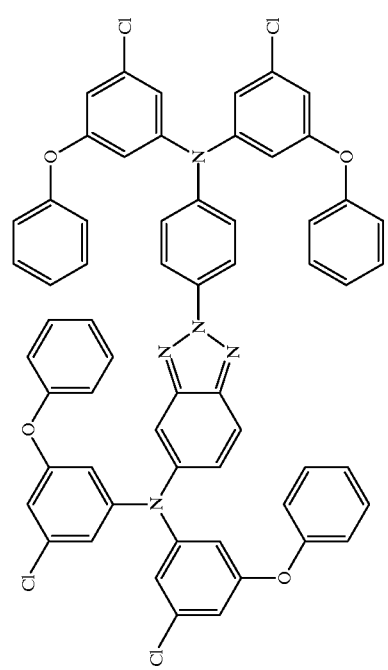 |

TABLE 3-continued
| compound | Chemical structure |
|---|---|
| (42) | 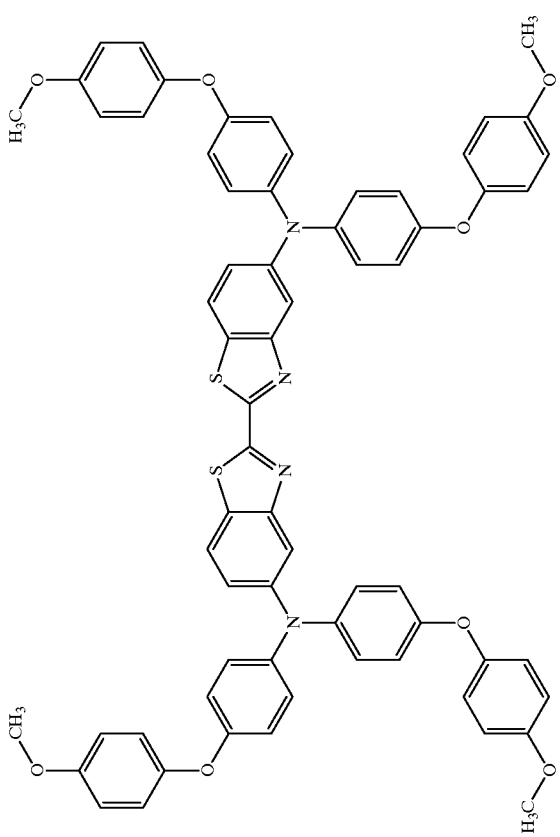 |

TABLE 3-continued
| compound | Chemical structure |
|---|---|
| (43) | 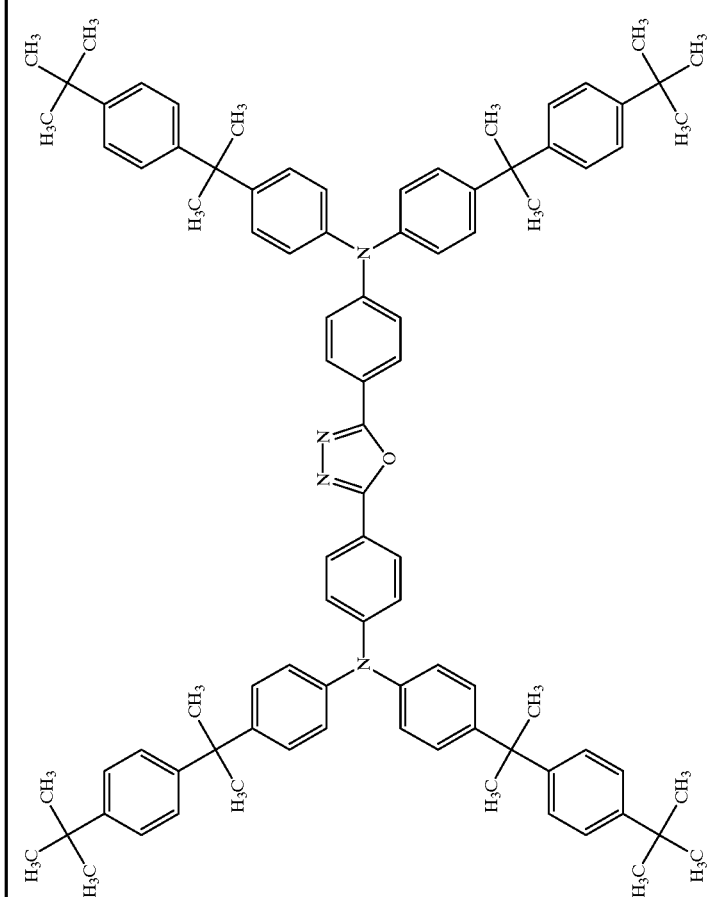 |

TABLE 3-continued

| compound | Chemical structure |
|---|---|
| (44) | 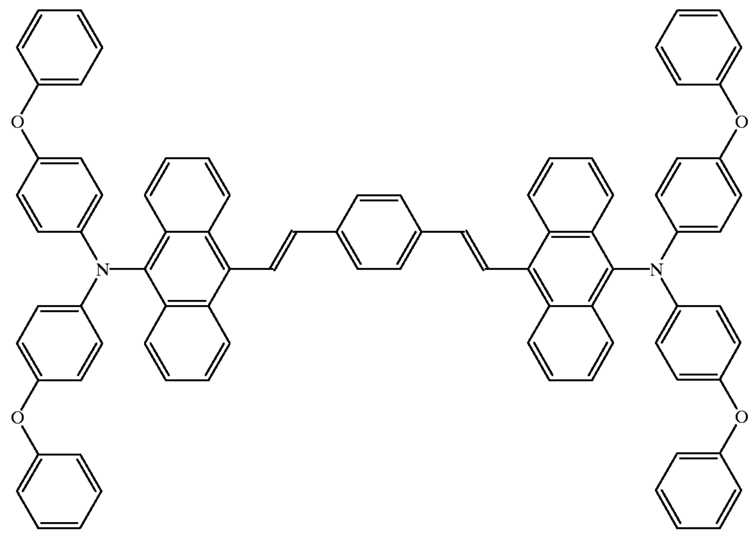 |

TABLE 3-continued

| compound | Chemical structure |
|---|---|
| (45) | 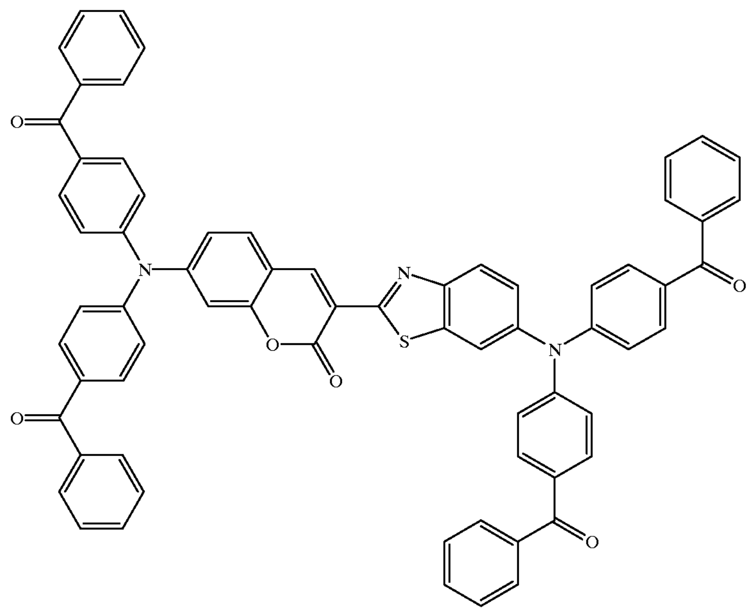 |

TABLE 3-continued
| compound | Chemical structure |
|---|---|
| (46) | 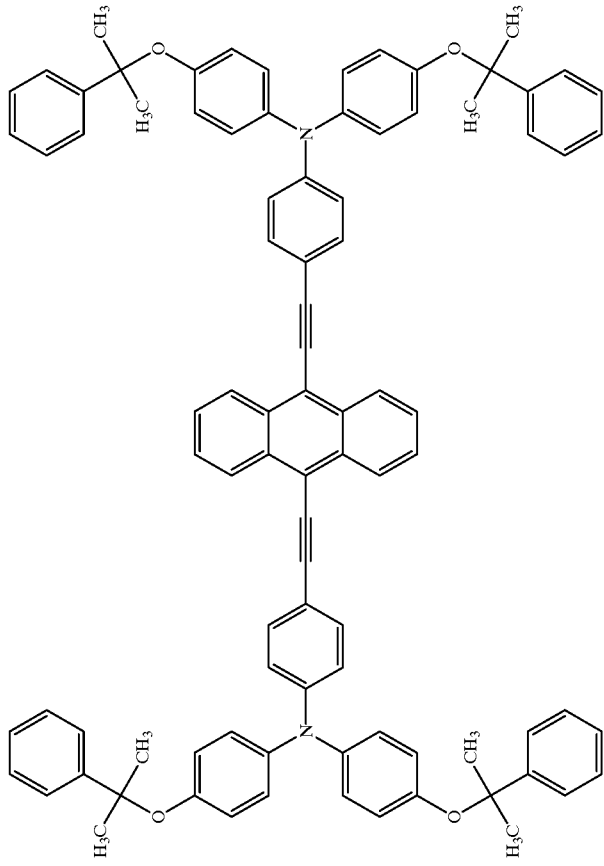 |

TABLE 3-continued
| compound | Chemical structure |
|---|---|
| (47) | 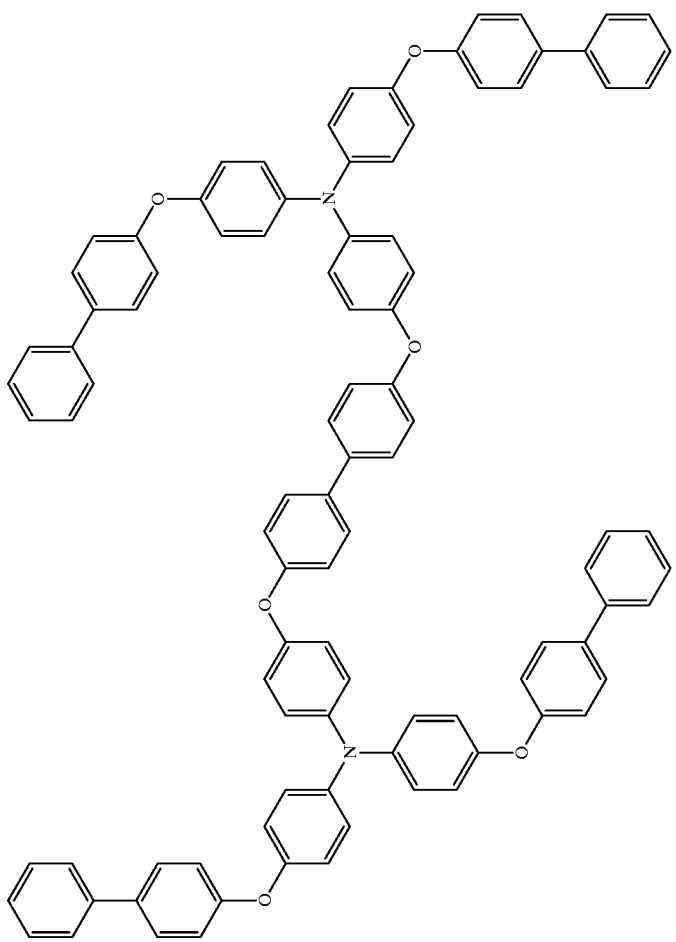 |

TABLE 3-continued

| compound | Chemical structure |
|---|---|
| (48) | 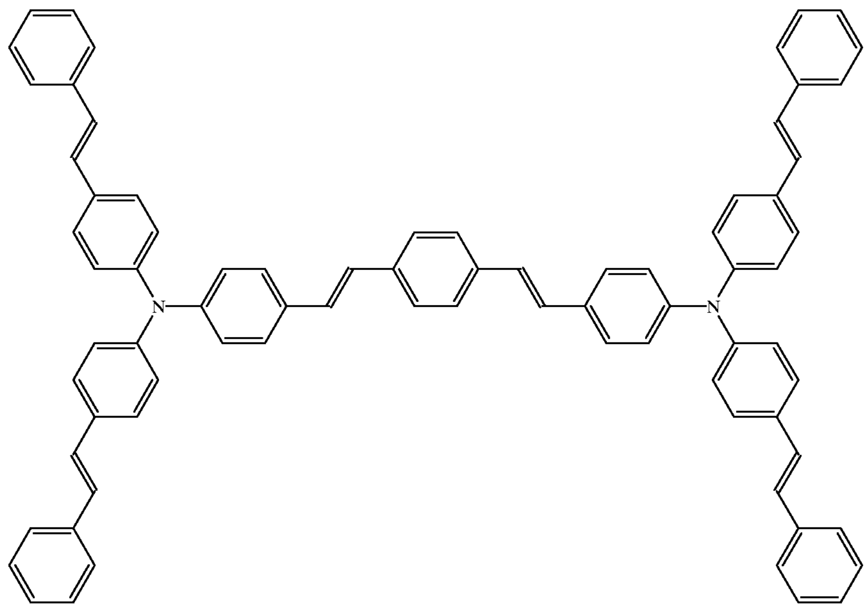 |

TABLE 3-continued
| compound | Chemical structure |
|---|---|
| (49) | 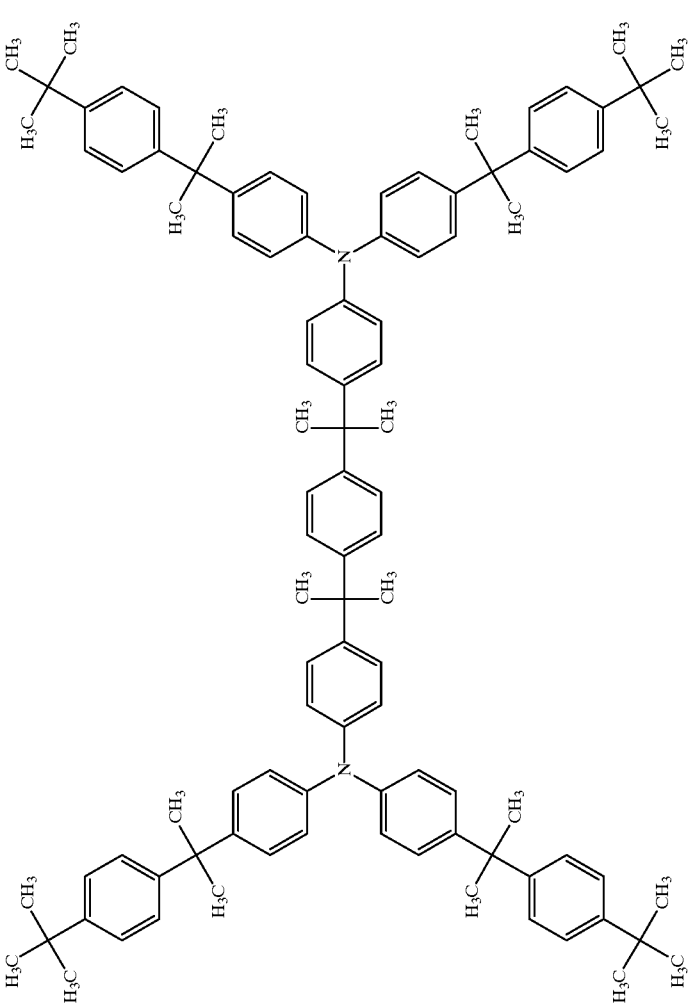 |

TABLE 3-continued
| compound | Chemical structure |
|---|---|
| (50) (51) | 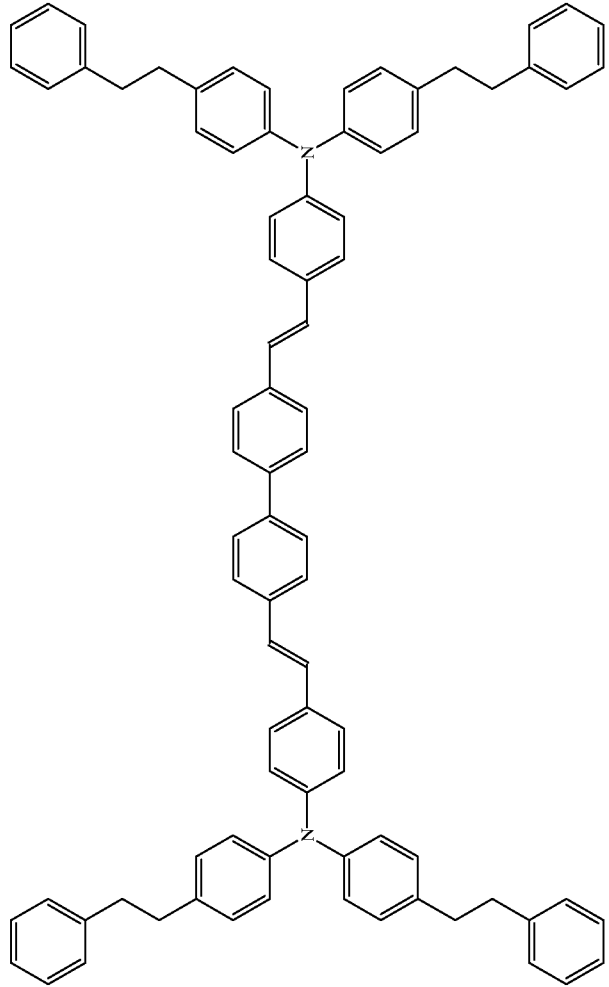 |

TABLE 3-continued

| compound | Chemical structure |
|---|---|
| (52) | 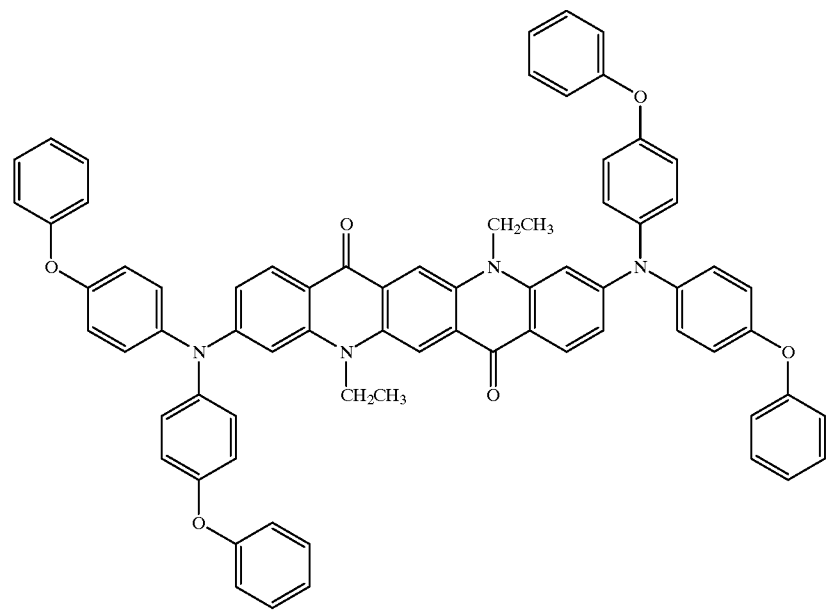 |

TABLE 3-continued
| compound | Chemical structure |
|---|---|
| (53) | 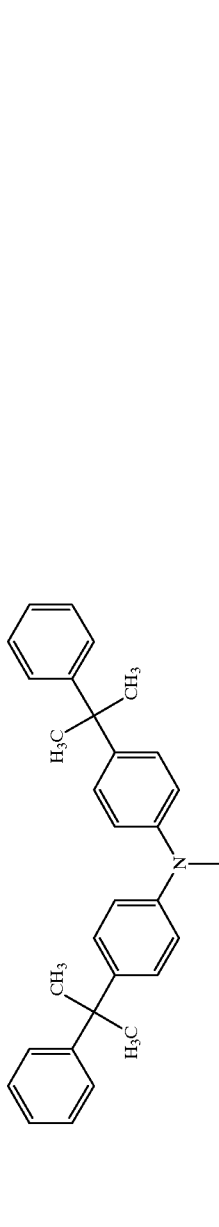 |

TABLE 3-continued
| compound | Chemical structure |
|---|---|
| (54) | 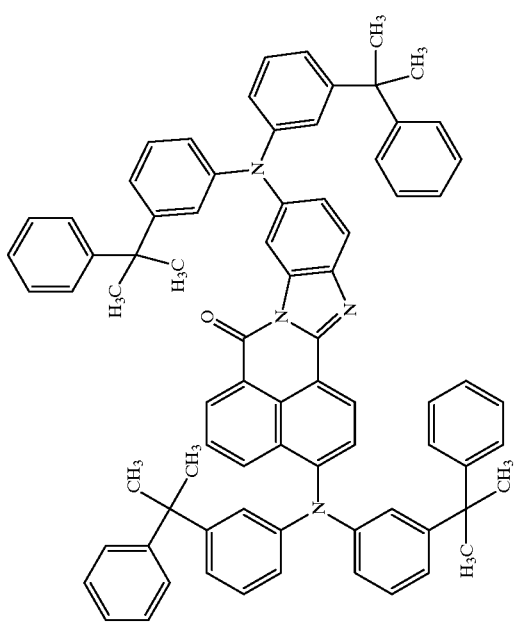 |

TABLE 3-continued

| compound | Chemical structure |
|---|---|
| (55) | 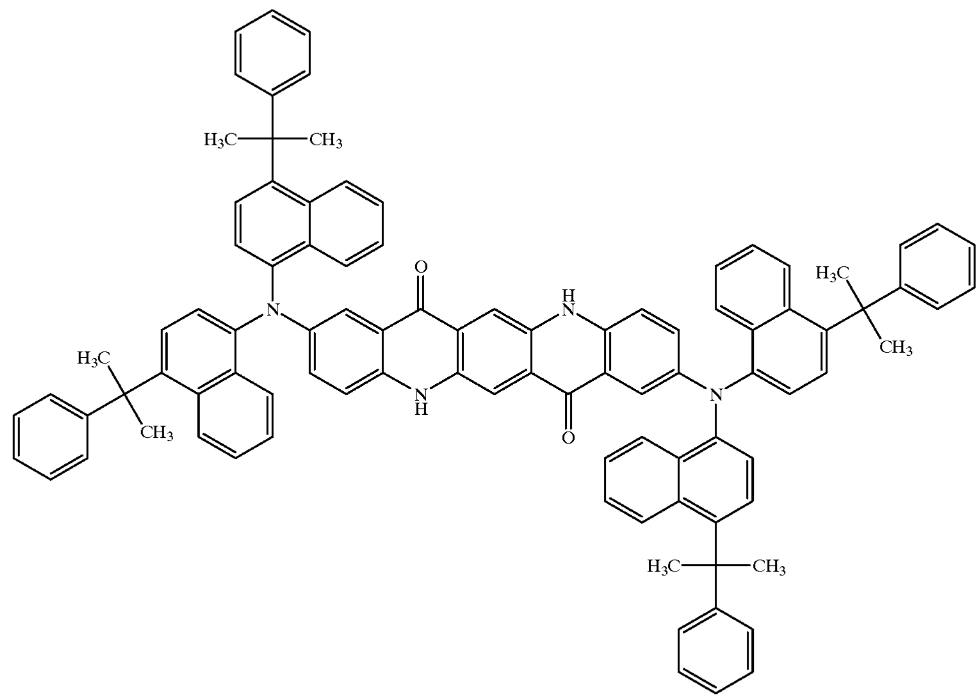 |

TABLE 3-continued

| compound | Chemical structure |
|---|---|
| (56) | 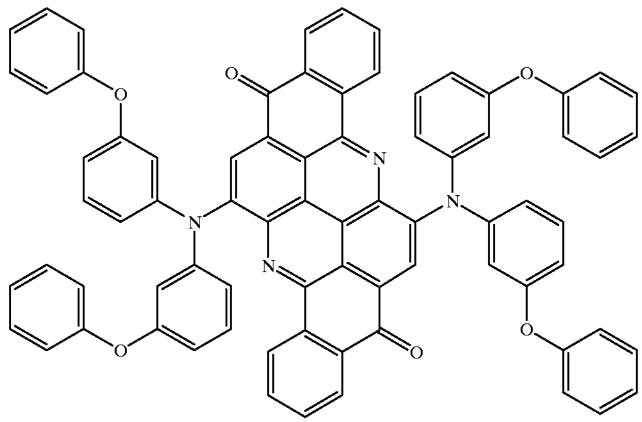 |
| (57) | 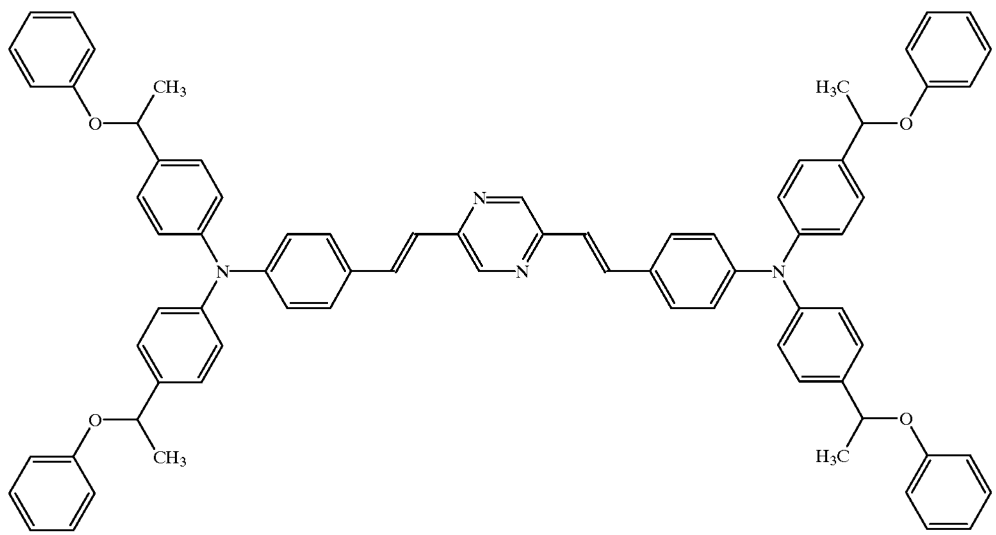 |

TABLE 3-continued

| compound | Chemical structure |
|---|---|
| (58) | 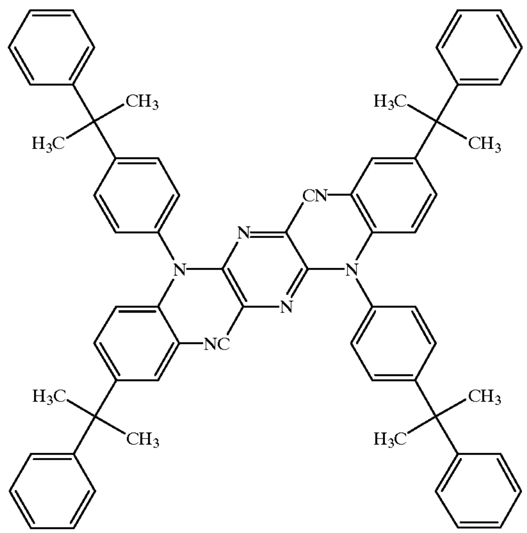 |
| (59) | 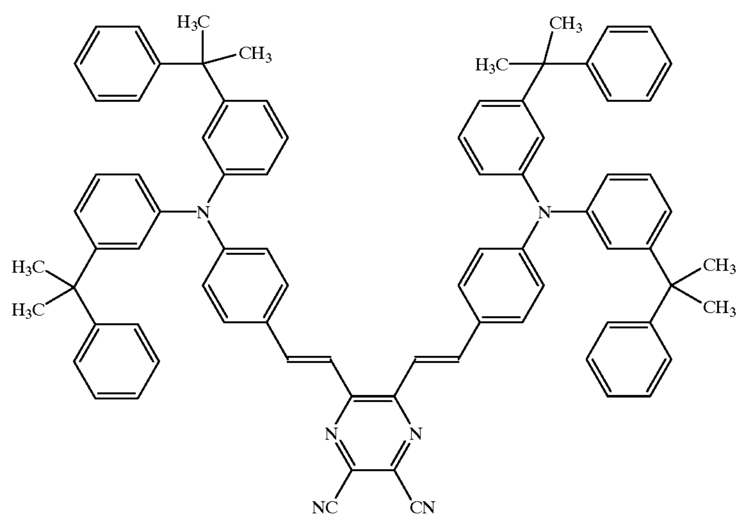 |

TABLE 3-continued

| compound | Chemical structure |
|---|---|
| (60) | 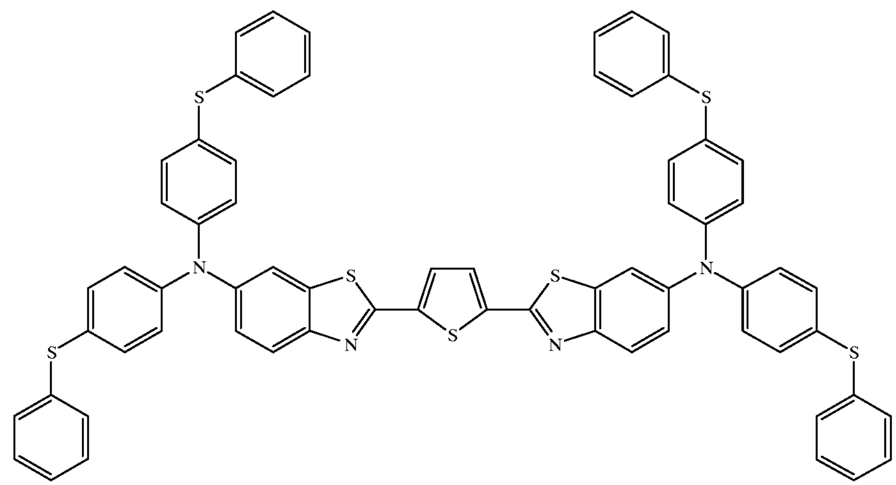 |

TABLE 3-continued
| compound | Chemical structure |
|---|---|
| (61) | 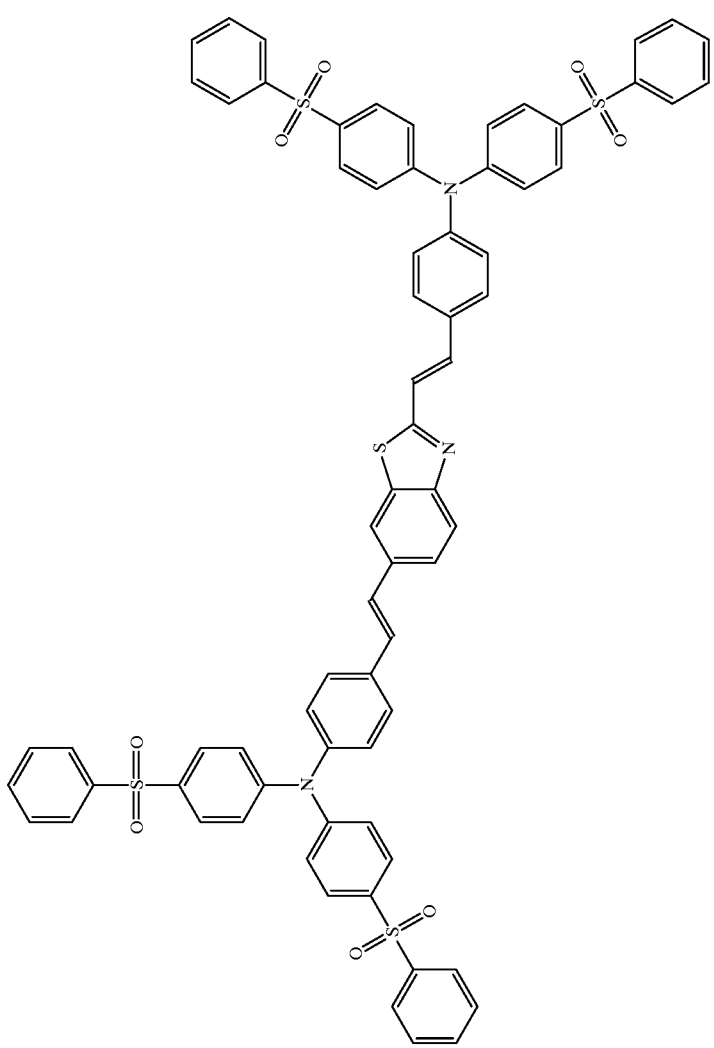 |

TABLE 3-continued

| compound | Chemical structure |
|---|---|
| (62) | 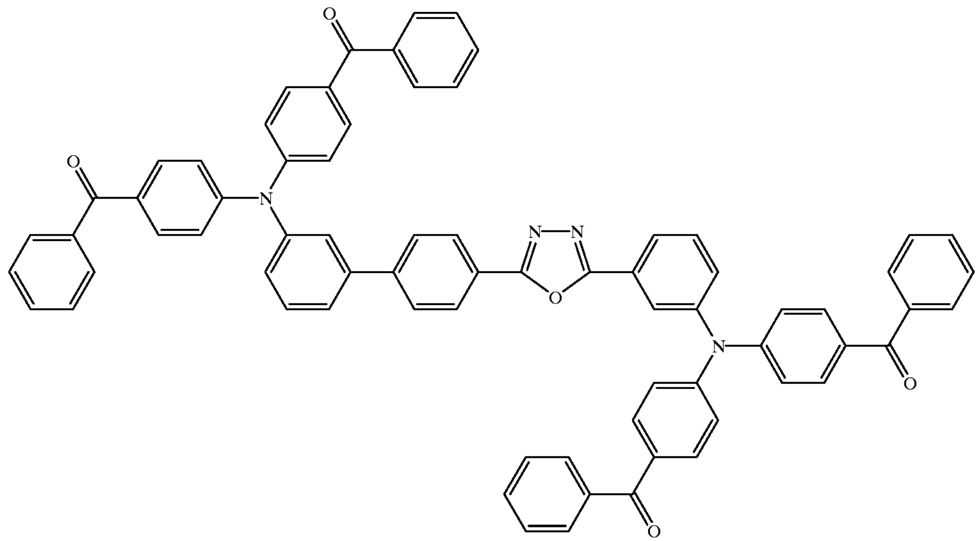 |

TABLE 3-continued
| compound | Chemical structure |
|---|---|
| (63) | 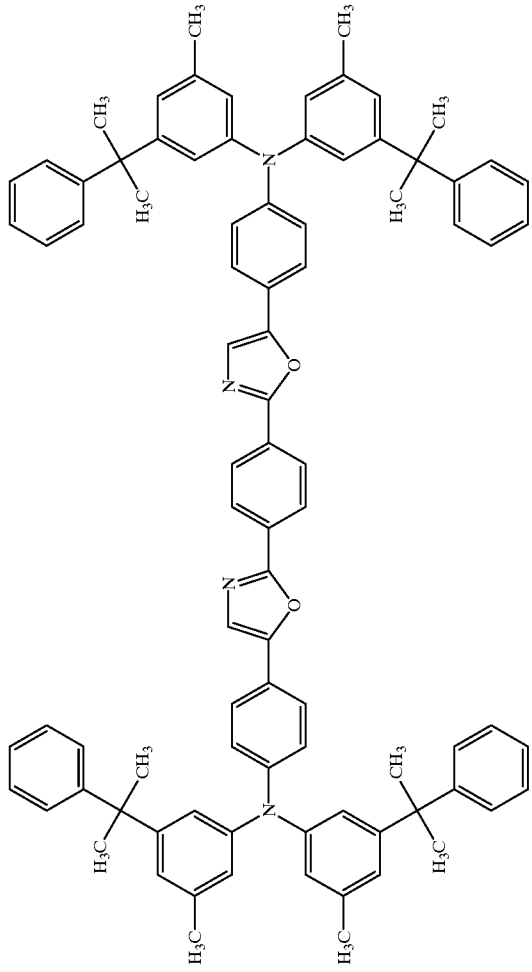 |

TABLE 3-continued
| compound | Chemical structure |
|---|---|
| (64) | 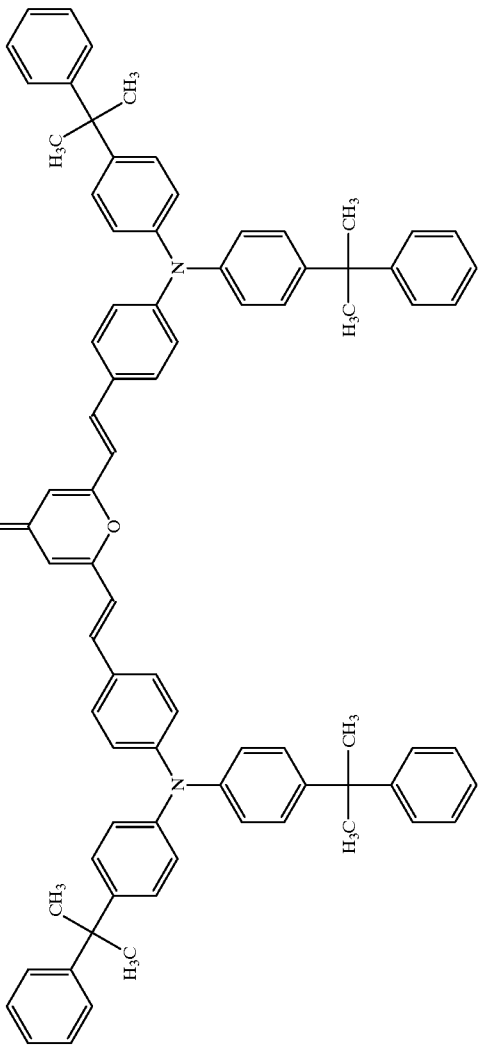 |

TABLE 3-continued

| compound | Chemical structure |
|---|---|
| (65) | 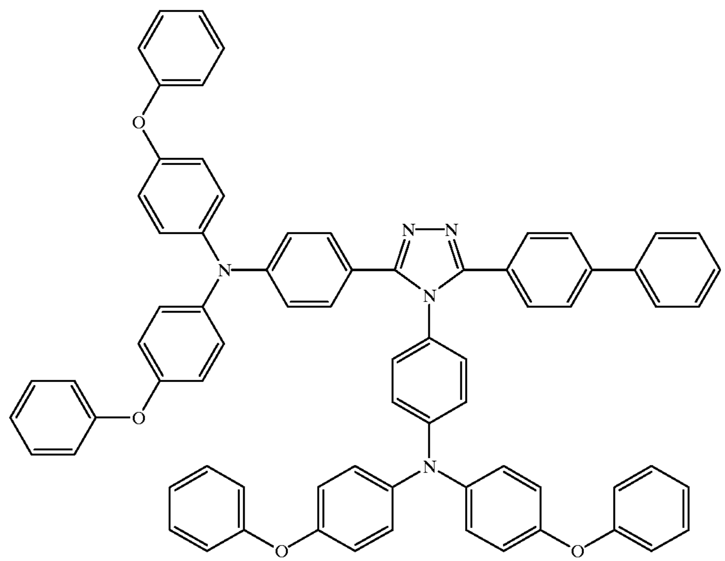 |

TABLE 3-continued
| compound | Chemical structure |
| --- | --- |
| (66) | 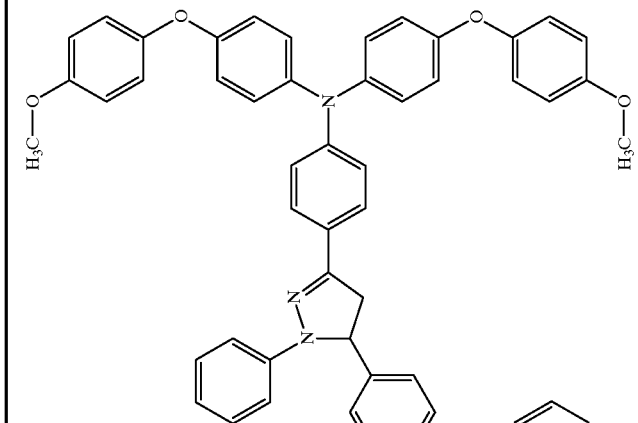 |

TABLE 3-continued

| compound | Chemical structure |
|---|---|
| (67) | 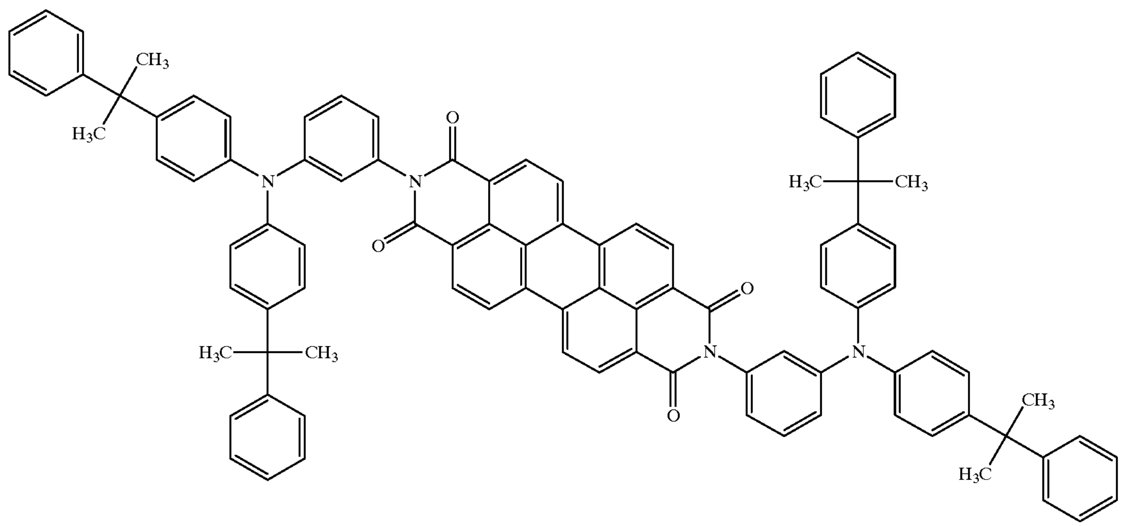 |
| (68) | 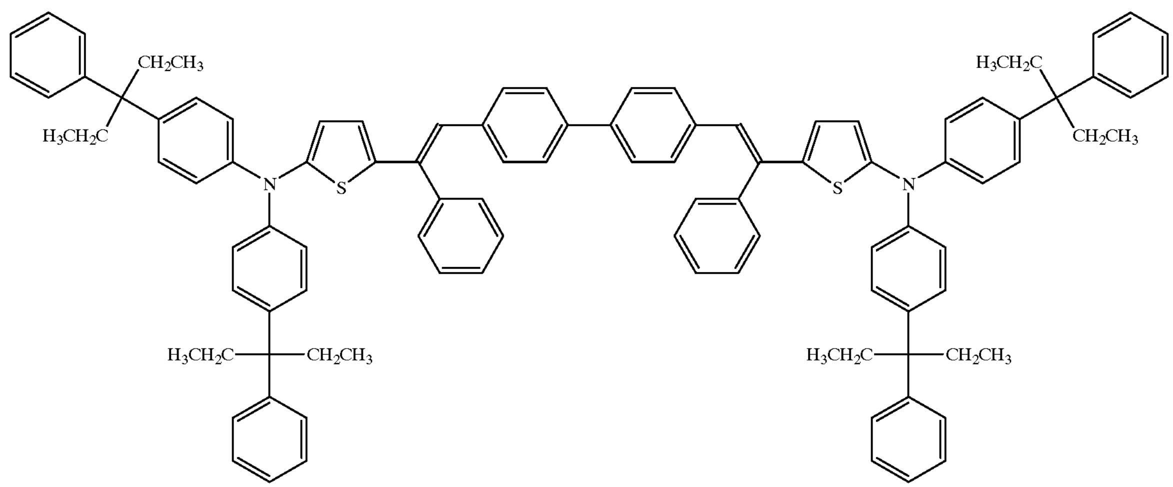 |

TABLE 3-continued

| compound | Chemical structure |
|---|---|
| (69) | 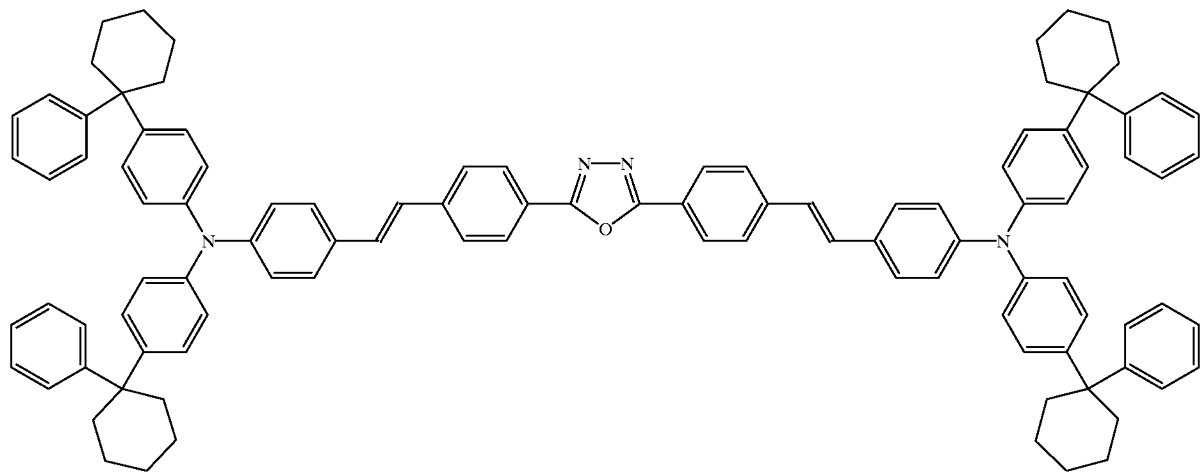 |
| (70) | 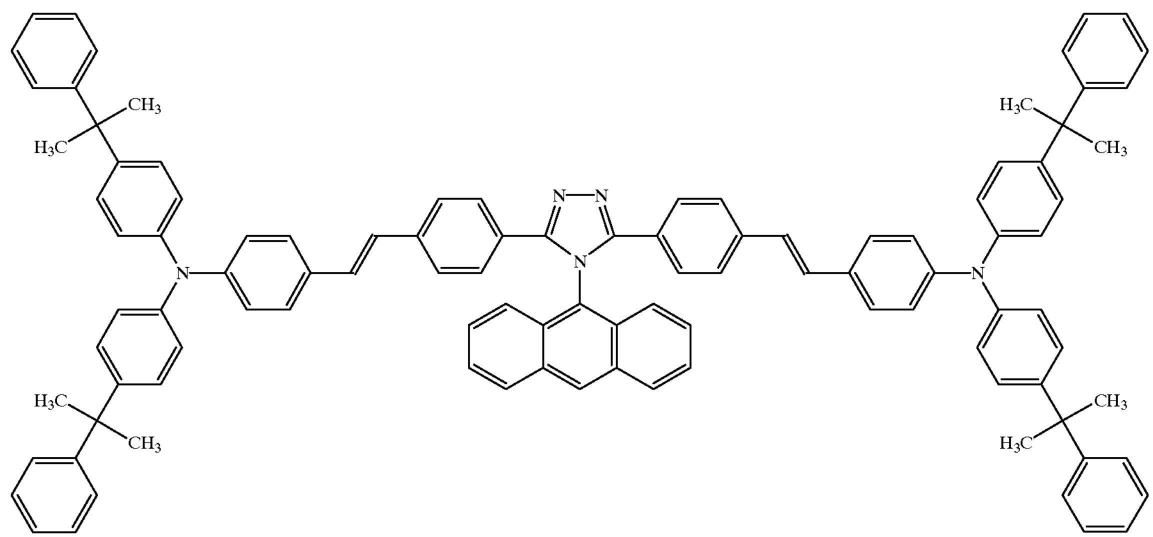 |

TABLE 3-continued
| compound | Chemical structure |
|---|---|
| (71) | 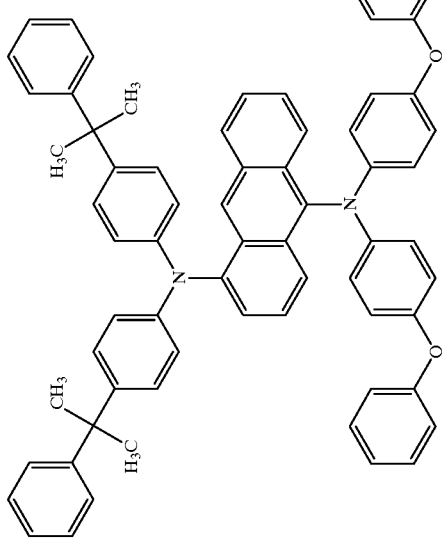 |
| (72) | 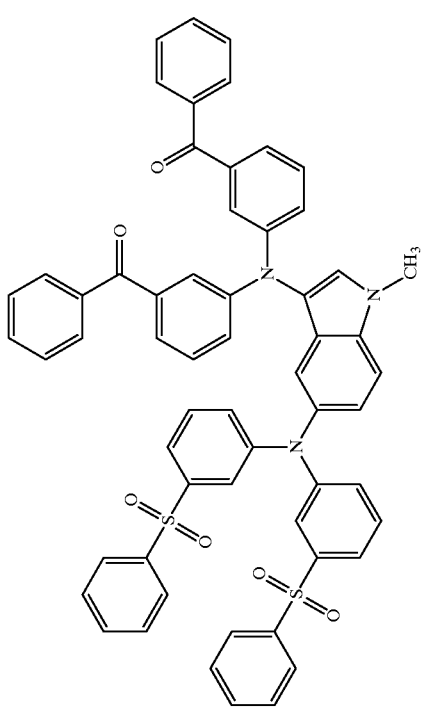 |

TABLE 3-continued
| compound | Chemical structure |
|---|---|
| (73) | 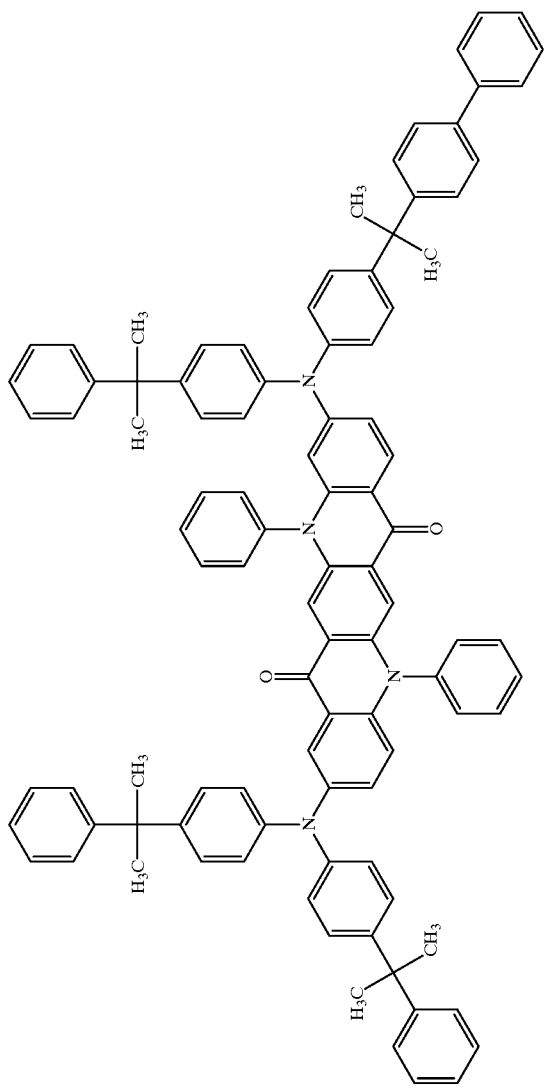 |

TABLE 3-continued
| compound | Chemical structure |
|---|---|
| (74) | 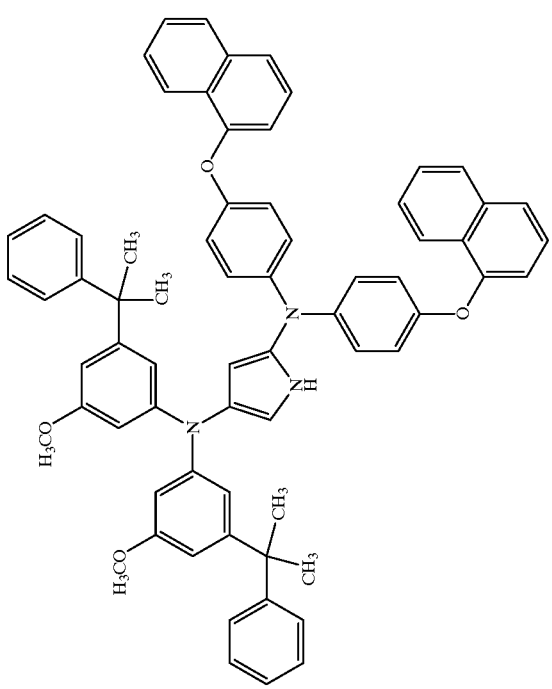 |

TABLE 3-continued
| compound | Chemical structure |
|---|---|
| (75) | 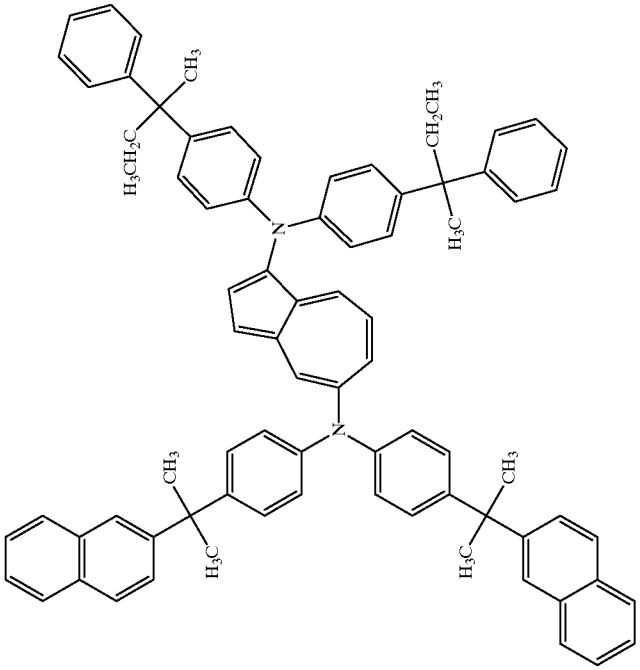 |
| (76) | 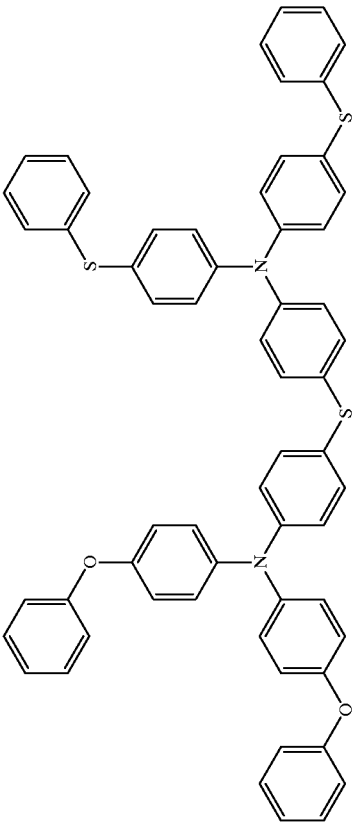 |

TABLE 3-continued
| compound | Chemical structure |
|---|---|
| (77) | 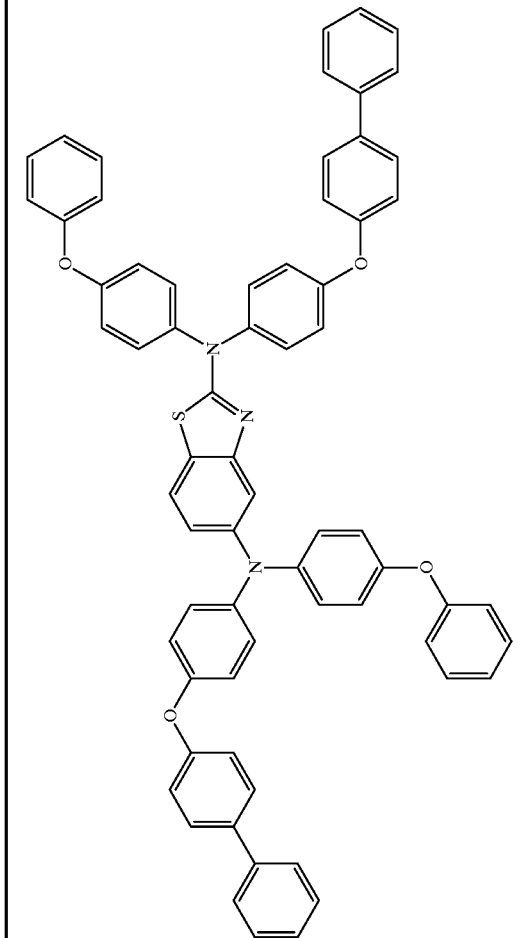 |
| (78) | 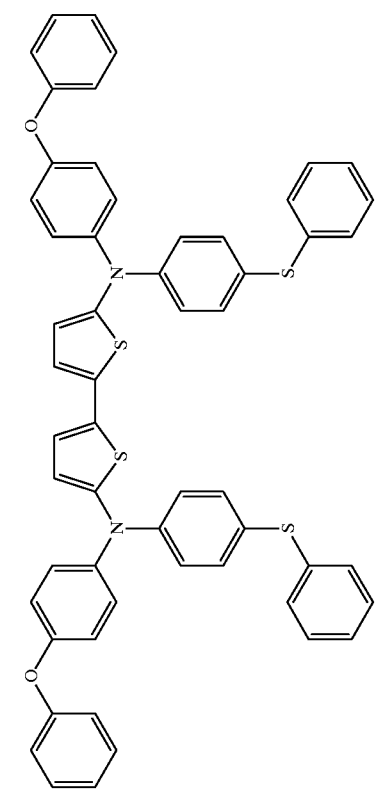 |

TABLE 3-continued
| compound | Chemical structure |
|---|---|
| (79) | 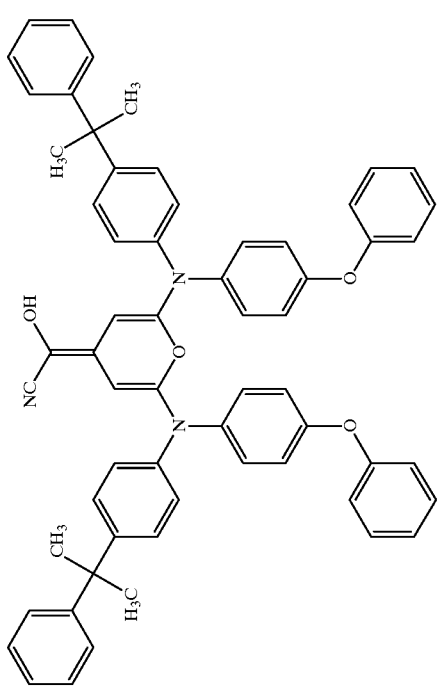 |
| (80) | 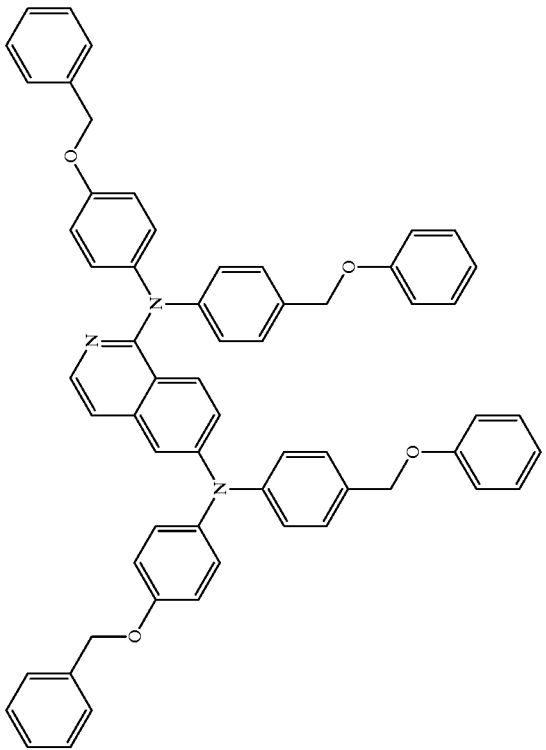 |

TABLE 3-continued
| compound | Chemical structure |
|---|---|
| (81) | 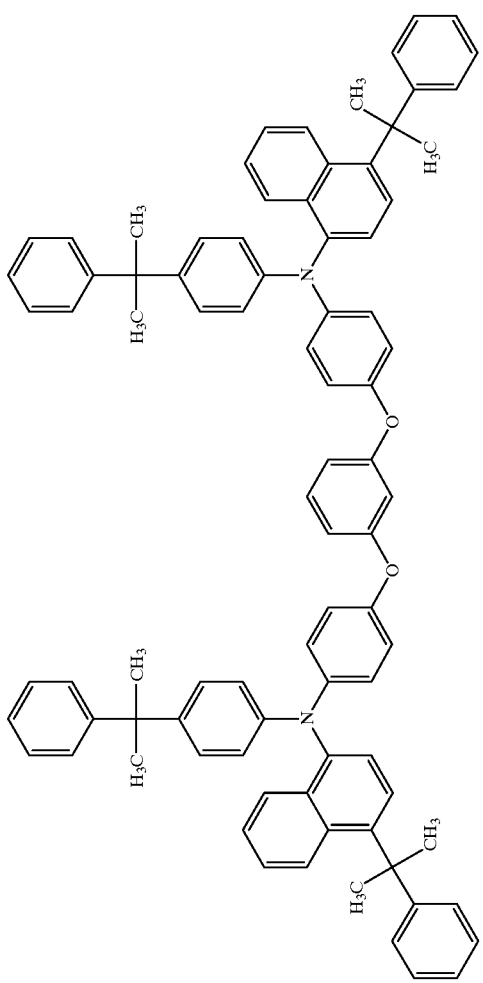 |

TABLE 3-continued
| compound | Chemical structure |
|---|---|
| (82) | 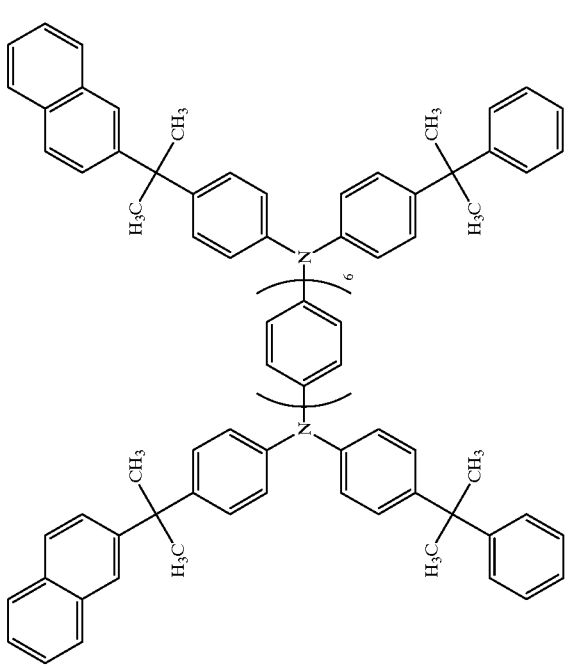 |

TABLE 3-continued
| compound | Chemical structure |
|---|---|
| (83) | 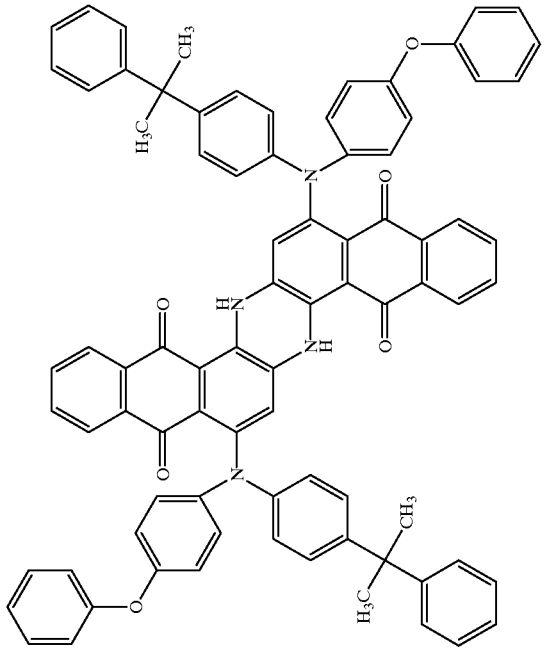 |

TABLE 3-continued
| compound | Chemical structure |
|---|---|
| (84) | 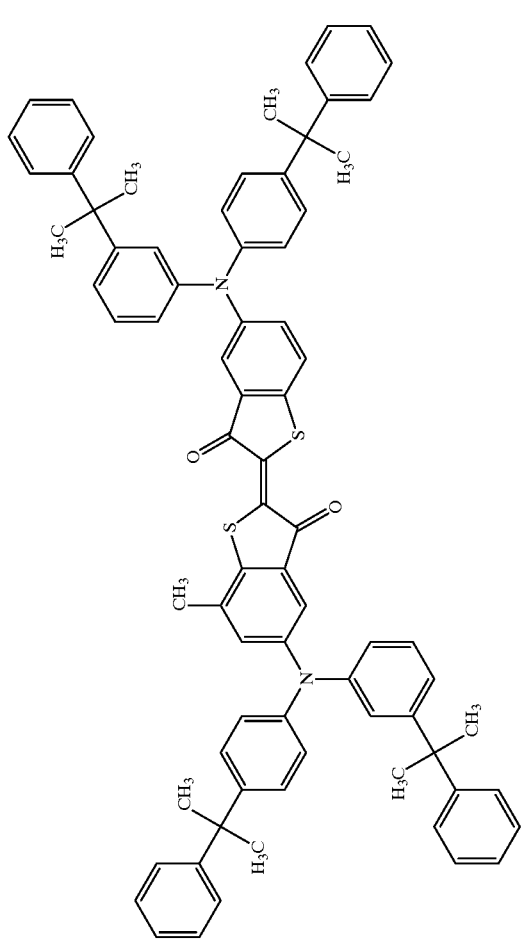 |

The light-emitting material of the present invention (compounds of the present invention) is a compound having intense fluorescence in a solid state, and is excellent in electric-field-applied light emission characteristic. Further, the light-emitting material of the present invention is excellent in the characteristic of injection of holes from a metal electrode and the property of transportation of holes, and it is also excellent in the characteristics of injection of electrons from a metal electrode and the property of transportation of electrons. It can be therefore effectively used as a light-emitting material, and further, it can be used in combination with other hole-transporting material, an electron-transporting material or a dopant without any problem.

An organic EL device is a device having a structure in which a mono- or multi-layered organic thin layer is formed between an anode and a cathode. In a mono-layered device, a light-emitting layer is formed between the anode and the cathode. The light-emitting layer contains a light-emitting material, and in addition thereto, it may contain a hole-injecting material for transporting holes injected from the anode to the light-emitting material, or an electron-injecting material for transporting electrons injected from the cathode to the light-emitting material. The light-emitting material of the present invention has a remarkably high light emission quantum efficiency, high capability of transporting holes and high capability of transporting electrons and can form a uniform thin film. The light-emitting layer can be therefore formed of the light-emitting material of the present invention alone. A multi-layered organic EL device has one of laminated-layer structures, for example, of (anode/hole-injecting zone/light-emitting layer/cathode), (anode/light-emitting layer/electron-injecting layer/zone) and (anode/hole-injecting zone/light-emitting layer/electron-injecting zone/cathode). The light-emitting material of the present invention (compounds of the present invention) can be used in a light-emitting layer due to its characteristic of high light emission, property of injecting holes, capability of transporting holes and property of injecting electrons and capability of transporting electrons.

In addition to the material of the present invention, the light-emitting layer may contain a known light-emitting material, a known dopant, a known hole-injecting material or a known electron-injecting material as required. In the organic EL device, a decrease in the brightness and life caused by quenching can be prevented by forming it as a multi-layered structure. The light-emitting material, a dopant, a hole-injecting material and an electron-injecting material may be used in combination as required. Further, a dopant can improve the light emission brightness and the light emission efficiency, and can attain the red or blue light emission. Further, each of the hole-injecting zone, the light-emitting layer and the electron-injecting zone may have the layer structure of at least two layers. In the hole-injecting zone in this case, a layer to which holes are injected from an electrode is called "hole-injecting layer", and a layer which receives holes from the hole-injecting layer and transport the holes to a light-emitting layer is called "hole-transporting layer". In the electron-injecting zone, a layer to which electrons are injected from an electrode is called "electron-injecting layer", and a layer which receives electrons from the electron-injecting layer and transports the electrons to a light-emitting layer is called "electron-transporting layer". These layers are selected and used depending upon factors such as the energy level and heat resistance of materials and adhesion to an organic layer or metal electrode.

The light-emitting material or the dopant which may be used in the light-emitting layer together with the light-emitting material of the present invention includes anthracene, naphthalene, phenanthrene, pyrene, tetracene, coronene, chrysene, fluorescein, perylene, phthaloperylene, naphthaloperylene, perinone, phthaoperinone, naphthaloperinone, diphenylbutadiene, tetraphenylbutadiene, coumarine, oxadiazole, aldazine, bisbenzoxazoline, bisstyryl, pyrazine, cyclopentadiene, quinoline metal complex, aminoquinoline metal complex, benzoquinoline metal complex, imine, diphenylethylene, vinyl anthracene, diaminocarbazole, pyran, thiopyran, polymethine, merocyanine, an imidazole-chelated oxynoid compound, quinacridone, rubrene, and fluorescent dyestuffs for a dyestuff laser or for brightening, although the above material shall not be limited to these.

The light-emitting material of the present invention and the above compound that can be used in a light-emitting layer may be used in any mixing ratio for forming a light-emitting layer. That is, the light-emitting material of the present invention may be a main component for forming a light-emitting layer, and it may be a doping material in other main material, depending upon a combination of the above compound with the light-emitting material of the present invention.

The hole-injecting material is selected from compounds which are capable of transporting holes, are capable of receiving holes from the anode, have an excellent effect of injecting holes to a light-emitting layer or a light-emitting material, prevent the movement of excitons generated in a light-emitting layer to an electron-injecting zone or an electron-injecting material and have the excellent capability of forming a thin film. Specific examples of the above hole-injecting material include a phthalocyanine derivative, a naphthalocyanine derivative, a porphyrin derivative, oxazole, oxadiazole, triazole, imidazole, imidazolone, imidazolthione, pyrazoline, pyrazolone, tetrahydroimidazole, oxazole, oxadiazole, hydrazone, acylhydrazone, polyarylalkane, stilbene, butadiene, benzidine type triphenylamine, styrylamine type triphenylamine, diamine type triphenylamine, derivatives of these, and polymer materials such as polyvinylcarbazole, polysilane and an electroconducting polymer. However, the hole-transporting material shall not be limited to the above materials.

In the organic EL device of the present invention, the hole-injecting material which is more effective is an aromatic tertiary amine derivative or a phthalocyanine derivative. Although not specially limited, specific examples of the tertiary amine derivative include triphenylamine, tritolylamine, tolyldiphenylamine, N,N'-diphenyl-N,N'-(3-methylphenyl)-1,1-biphenyl-4,4'-diamine, N,N,N',N'-tetra(4-methylphenyl)-1,1'-phenyl-4,4'-diamine, N,N,N',N'-tetra(4-methylphenyl)-1,1'-biphenyl-4,4'-diamine, N,N'-diphenyl-N,N'-di(1-naphthyl)-1,1'-biphenyl-4,4'-diamine, N,N'-di(methylphenyl)-N,N'-di(4-n-butylphenyl)-phenanthrene-9,10- diamine, 4,4', 4"-tris(3-methylphenyl)-N-phenylamino)triphenylamine, 1,1-bis(4-di-p-tolylaminophenyl)cyclohexane, and oligomers or polymers having aromatic tertiary amine structures of these.

Although no specially limited, specific examples of the phthalocyanine (Pc) derivative include phthalocyanine derivatives or naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O-GaPc.

The electron-injecting material is a material which is capable of transporting electrons, receiving electrons from a cathode, injecting electrons into a light-emitting layer or light-emitting material, preventing excitons generated in the light-emitting layer from moving into a hole-injecting zone and forming a thin film. Although not specially limited, examples of the electron-injecting material include fluorenone, anthraquinodimethane, diphenoquinone, thiopyran dioxide, oxazole, oxadiazole, triazole, imidazole, perylenetetracarboxylic acid, fluorenylidenemethane, anthrone and derivatives of these. The hole-injecting material may be sensitivity-increased by incorporating an electron-accepting material, and the electron-injecting material may be sensitivity-increased by incorporating an electron-donating material.

In the organic EL device of the present invention, the electron-injecting material which is more effective is a metal complex compound or a nitrogen-containing five-membered derivative. Although not specially limited, specific examples of the metal complex compound include lithium 8-hydroxyquinolinate, zinc bis(8-hydroxyquinolinate), copper bis(8-hydroxyquinolinate), manganese bis(8-hydroxyquinolinate), aluminum tris(8-hydroxyquinolinate), aluminum tris(2-methyl-8-hydroxyquinolinate), gallium tris(8-hydroxyquinolinate), beryllium bis(10-hydroxybenzo[h]quinolinate), zinc bis(10-hydroxybenzo[h]quinolinate), chlorogallium bis(2-methyl-8-quinolinate), gallium bis(2-methyl-8-quinolinate)(o-cresolate), aluminum bis(2-methyl-8-quinolinate)(1-naphtholate), gallium bis(2-methyl-8-quinolinate)(2-naphtholate), gallium bis(2-methyl-8-quinolinate)phenolate, zinc bis(o-(2-benzooxazolyl)phenolate), zinc bis(o-(2-benzothiazolyl)phenolate) and zinc bis(o-(2-benzotrizolyl)phenolate). The nitrogen-containing five-membered derivative is preferably an oxazole, thiazole, thiadiazole, or triazole derivative. Although not specially limited, specific examples of the above nitrogen-containing five-membered derivative include 2,5-bis(1-phenyl)-1,3,4-oxazole, 1,4-bis(2-(4-methyl-5-phenyloxazolyl)benzene, 2,5-bis(1-phenyl)-1,3,4-thiazole, 2,5-bis(1-phenyl)-1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene.

In the organic EL device of the present invention, the light-emitting layer may contain, in addition to the light-emitting material of the present invention, at least one of other light-emitting material, other dopant, other hole-injecting material and other electron-injecting material. For improving the organic EL device of the present invention in the stability against temperature, humidity and ambient atmosphere, a protective layer may be formed on the surface of the device, or the device as a whole may be sealed with a silicone oil, or the like.

The electrically conductive material used for the anode of the organic EL device is suitably selected from those materials having a work function of greater than 4 eV. The electrically conductive material includes carbon, aluminum, vanadium, iron, cobalt, nickel, tungsten, silver, gold, platinum, palladium, alloys of these, metal oxides such as tin oxide and indium oxide used for ITO substrates or NESA substrates, and organic electroconducting polymers such as polythiophene and polypyrrole.

The electrically conductive material used for the cathode is suitably selected from those having a work function of smaller than 4 eV. The electrically conductive material includes magnesium, calcium, tin, lead, titanium, yttrium, lithium, ruthenium, manganese, aluminum and alloys of these, while the electrically condutive material shall not be limited to these. Examples of the alloys include magnesium/silver, magnesium/indium and lithium/aluminum, while the alloys shall not be limited to these. Each of the anode and the cathode may have a layer structure formed of two layers or more as required.

For the effective light emission of the organic EL device, at least one of the electrodes is desirably sufficiently transparent in the light emission wavelength region of the device. Further, the substrate is desirably transparent as well. The transparent electrode is produced from the above electrically conductive material by a deposition method or a sputtering method such that a predetermined light transmittance is secured. The electrode on the light emission surface side preferably has a light transmittance of at least 10%. The substrate is not specially limited so long as it has adequate mechanical and thermal strength and has transparency. For example, it is selected from glass substrates and substrates of transparent resins such as a polyethylene substrate, a polyethylene terephthalate substrate, a polyether sulfone substrate and a polypropylene substrate.

In the organic EL device of the present invention, each layer can be formed by any one of dry film forming methods such as a vacuum deposition method, a sputtering method, a plasma method and an ion plating method and wet film forming methods such as a spin coating method, a dipping method and a flow coating method. The thickness of each layer is not specially limited, while each layer is required to have a proper thickness. When the layer thickness is too large, inefficiently, a high voltage is required to achieve predetermined emission of light. When the layer thickness is too small, the layer is liable to have a pinhole, etc., so that sufficient light emission brightness is hard to obtain when an electric field is applied. Generally, the thickness of each layer is preferably in the range of from 5 nm to 10 $\mu$m, more preferably 10 nm to 0.2 $\mu$m.

In the wet film forming method, a material for forming an intended layer is dissolved or dispersed in a proper solvent such as ethanol, chloroform, tetrahydrofuran and dioxane, and a thin film is formed from the solution or dispersion. The solvent shall not be limited to the above solvents. For improving the film formability and preventing the occurrence of pinholes in any layer, the above solution or dispersion for forming the layer may contain a proper resin and a proper additive. The resin that can be used includes insulating resins such as polystyrene, polycarbonate, polyarylate, polyester, polyamide, polyurethane, polysulfone, polymethyl methacrylate, polymethyl acrylate and cellulose, copolymers of these, photoconductive resins such as poly-N-vinylcarbozole and polysilane, and electroconducting polymers such as polythiophene and polypyrrole. The above additive includes an antioxidant, an ultraviolet absorbent and a plasticizer.

When the light-emitting material of the present invention is used in a light-emitting layer of an organic EL device, an organic EL device can be improved in organic EL device characteristics such as light emission efficiency and maximum light emission brightness. Further, the organic EL device of the present invention is remarkably stable against heat and electric current and gives a practically usable light emission brightness at a low actuation voltage. The deterioration which is a big problem of conventional devices can be remarkably decreased.

The organic EL device of the present invention has significant industrial values since it can be adapted for a flat panel display of an on-wall television set, a flat light-emitting device, a light source for a copying machine or a printer, a light source for a liquid crystal display or counter, a display signboard and a signal light.

The material of the present invention can be used in the fields of an organic EL device, an electrophotographic photoreceptor, a photoelectric converter, a solar cell, an image sensor, and the like.

EXAMPLES

The present invention will be explained more in detail with reference to Examples hereinafter.

Example 1

Compound (1) in Table 3 as a light-emitting material, 2,5-bis(1-naphthyl)-1,3,4-oxadiazole and a polycarbonate resin (Panlite K-1300, supplied by Teijin Kasei) in a weight ratio of 5:3:2 were dissolved in tetrahydrofuran, and the solution was spin-coated on a cleaned glass substrate with an ITO electrode to form a light-emitting layer having a thickness of 100 nm. An electrode having a thickness of 150 nm was formed thereon from a magnesium/indium alloy having a magnesium/indium mixing ratio of 10/1, to obtain an organic EL device. The device had the following light emission characteristics. The device showed blue light emission having a brightness of 90 ($cd/m^2$) at a direct current voltage of 5 V, a maximum brightness of 1,500 ($cd/m^2$) and a light emission efficiency of 0.50 lm/W.

Example 2

Compound (2) in Table 3 was vacuum-deposited on a cleaned glass substrate with an ITO electrode to form a light-emitting layer having a thickness of 100 nm. An electrode having a thickness of 100 nm was formed thereon from a magnesium/silver alloy having a magnesium/silver mixing ratio of 10/1, to obtain an organic EL device. The light-emitting layer was formed by deposition under a vacuum of $10^{-6}$ Torr at a substrate temperature of room temperature. The device showed green light emission having a brightness of 260 ($cd/m^2$) at a direct current voltage of 5 V, a maximum brightness of 800 ($cd/m^2$) and a light emission efficiency of 0.60 lm/W.

Example 3

Compound (3) in Table 3 was dissolved in methylene chloride tetrahydrofuran, and the solution was spin-coated on a cleaned glass substrate with an ITO electrode to form a light-emitting layer having a thickness of 50 nm. Then, aluminum bis(2-methyl-8-quinolinate)(2-naphtolate) was vacuum-deposited to form an electron-injecting layer having a thickness of 10 nm, and an electrode having a thickness of 100 nm was formed thereon from a magnesium/aluminum alloy having a magnesium/aluminum mixing ratio of 10/1, to obtain an organic EL device. The light-emitting layer and the electron-injecting layer were formed by deposition under a vacuum of $10^{-6}$ Torr at a substrate temperature of room temperature. The device showed bluish green light emission having a brightness of 200 ($cd/m^2$) at a direct current voltage of 5 V, a maximum brightness of 12,000 ($cd/m^2$) and a light emission efficiency of 1.2 lm/W.

Example 4

Compound (2) in Table 3 was vacuum-deposited on a cleaned glass substrate with an ITO electrode to form a light-emitting layer having a thickness of 50 nm. Then, aluminum tris(8-hydroxyquinolinate) was vacuum-deposited to form an electron-injecting layer having a thickness of 10 nm and an electrode having a thickness of 100 nm was formed thereon from an aluminum/lithium alloy having an aluminum/lithium mixing ratio of 50/1, to obtain an organic EL device. A hole-injecting layer and the light-emitting layer were formed by deposition under a vacuum of $10^{-6}$ Torr at a substrate temperature of room temperature. The device showed green light emission having a brightness of about 150 ($cd/m^2$) at a direct current voltage of 5 V, a maximum brightness of 9,000 ($cd/m^2$) and a light emission efficiency of 1.1 lm/W.

Examples 5 to 83

One of hole-injecting materials (H-1) to (H-6) in Table 4 was vacuum-deposited on a cleaned glass substrate with an ITO electrode, to form a hole-injecting layer having a thickness of 30 nm. Then, one of light-emitting materials in Table 3 was vacuum-deposited to form a light-emitting layer having a thickness of 30 nm. Further, one of electron-injecting materials (E-1) to (E-6) in Table 4 was vacuum-deposited to form an electron-injecting layer having a thickness of 30 nm. An electrode having a thickness of 150 nm was formed thereon from a magnesium/silver alloy having a magnesium/silver mixing ratio of 10/1, to obtain an organic EL device. Each layer was formed under a vacuum of $10^{-6}$ Torr at a substrate temperature of room temperature. Table 5 shows the materials used for producing the organic EL device and the light emission characteristics. All the organic EL devices obtained in these Examples showed high brightness characteristics, or a maximum brightness of at least 5,000 ($cd/m^2$).

TABLE 4
| compound | Chemical structure |
|---|---|
| (H-1) | 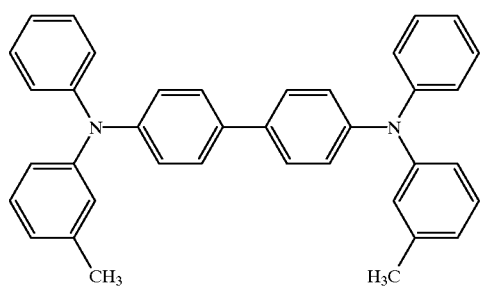 |
| (H-2) | 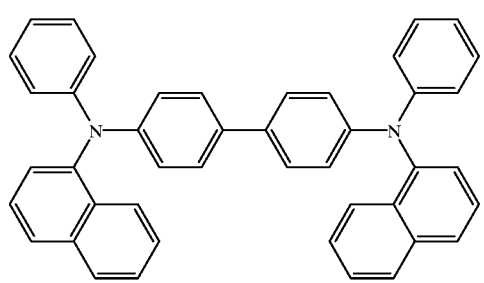 |
| (H-3) | 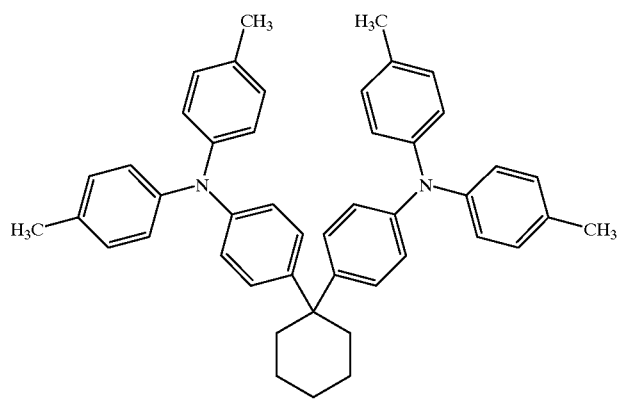 |
| (H-4) | 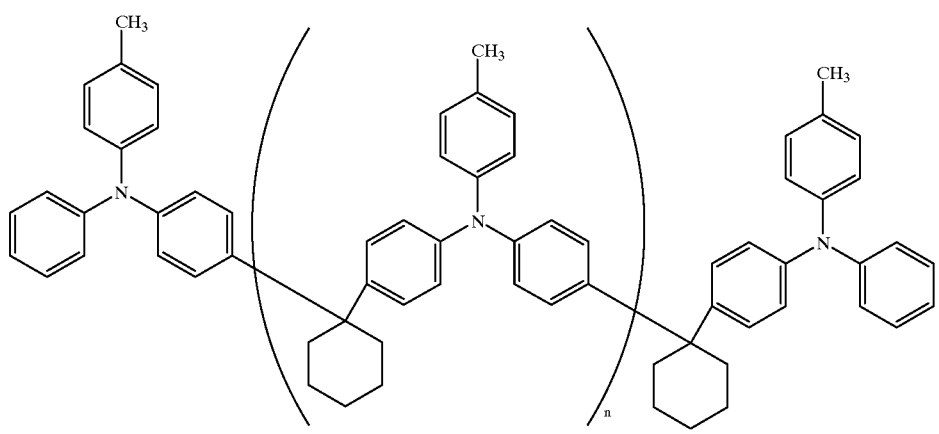<br>n = 2 ~ 6 |

TABLE 4-continued
| compound | Chemical structure |
|---|---|
| (H-5) | 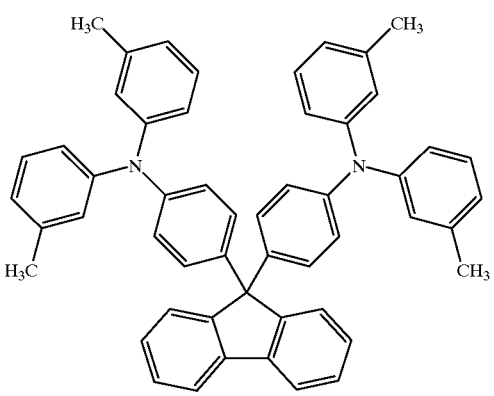 |
| (H-6) | 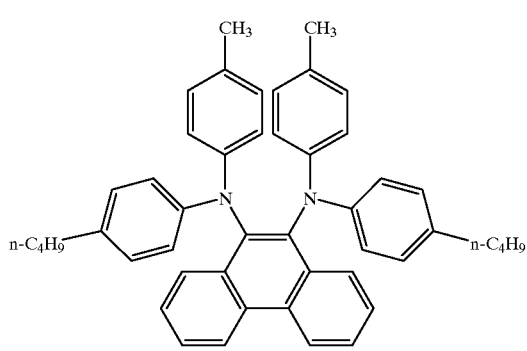 |
| (E-1) | 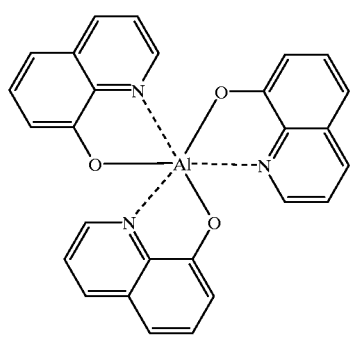 |
| (E-2) | 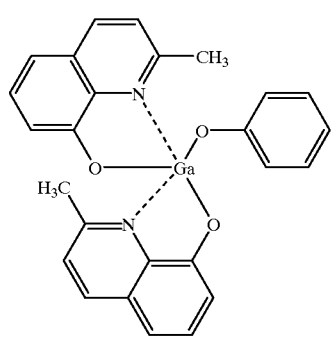 |

TABLE 4-continued
| compound | Chemical structure |
|---|---|
| (E-3) | 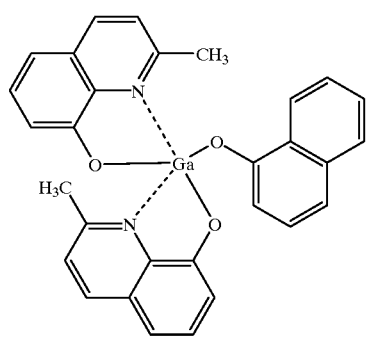 |
| (E-4) | 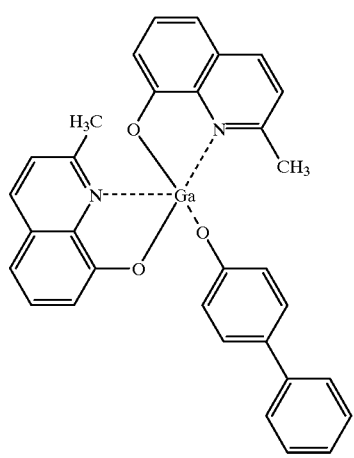 |
| (E-5) | 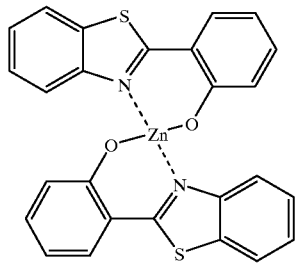 |
| (E-6) | 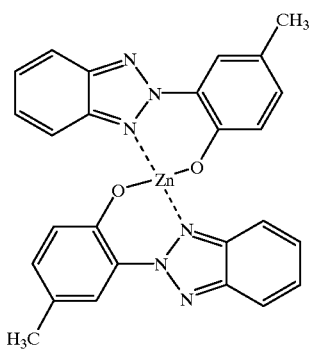 |

TABLE 5

| Ex. | Hole-injecting material (Table 4) | Light-emitting material (Table 3) | Electron-injecting material (Table 4) | Light emission brightness (cd/m²) | Maximum light emission brightness (cd/m²) | Maximum light emission efficiency (lm/W) |
|---|---|---|---|---|---|---|
| 5 | (H-1) | (6) | (E-2) | 280 | 29,800 | 2.2 |
| 6 | (H-2) | (7) | (E-3) | 550 | 24,300 | 3.9 |
| 7 | (H-3) | (8) | (E-1) | 230 | 27,500 | 2.7 |
| 8 | (H-4) | (9) | (E-5) | 540 | 21,200 | 3.3 |
| 9 | (H-5) | (10) | (E-6) | 370 | 12,600 | 1.4 |
| 10 | (H-6) | (11) | (E-4) | 420 | 49,000 | 2.5 |
| 11 | (H-3) | (12) | (E-2) | 360 | 45,700 | 4.6 |
| 12 | (H-4) | (13) | (E-3) | 330 | 38,500 | 4.8 |
| 13 | (H-1) | (14) | (E-5) | 460 | 31,900 | 2.7 |
| 14 | (H-5) | (15) | (E-4) | 390 | 30,300 | 3.2 |
| 15 | (H-4) | (16) | (E-5) | 310 | 15,600 | 2.8 |
| 16 | (H-6) | (17) | (E-5) | 760 | 7,000 | 1.8 |
| 17 | (H-3) | (18) | (E-6) | 710 | 26,800 | 2.2 |
| 18 | (H-2) | (19) | (E-5) | 350 | 9,200 | 2.3 |
| 19 | (H-6) | (20) | (E-2) | 600 | 40,400 | 4.4 |
| 20 | (H-3) | (21) | (E-2) | 560 | 17,400 | 3.5 |
| 21 | (H-6) | (22) | (E-4) | 400 | 9,200 | 1.9 |
| 22 | (H-1) | (23) | (E-1) | 310 | 34,900 | 3.1 |
| 23 | (H-6) | (24) | (E-2) | 720 | 50,300 | 5.7 |
| 24 | (H-5) | (25) | (E-1) | 400 | 40,300 | 5.4 |
| 25 | (H-5) | (26) | (E-5) | 550 | 54,200 | 4.6 |
| 26 | (H-2) | (27) | (E-6) | 780 | 28,300 | 2.9 |
| 27 | (H-3) | (28) | (E-6) | 300 | 25,000 | 2.4 |
| 28 | (H-4) | (29) | (E-6) | 230 | 50,600 | 4.7 |
| 29 | (H-4) | (30) | (E-5) | 380 | 41,500 | 4.1 |
| 30 | (H-4) | (31) | (E-4) | 330 | 47,500 | 3.3 |
| 31 | (H-1) | (32) | (E-5) | 790 | 17,800 | 2.3 |
| 32 | (H-4) | (33) | (E-4) | 350 | 6,600 | 1.6 |
| 33 | (H-6) | (34) | (E-5) | 330 | 33,300 | 3.5 |
| 34 | (H-4) | (35) | (E-3) | 600 | 39,900 | 3.5 |
| 35 | (H-6) | (36) | (E-2) | 540 | 31,100 | 3.6 |
| 36 | (H-5) | (37) | (E-6) | 560 | 25,900 | 2.4 |
| 37 | (H-6) | (38) | (E-5) | 680 | 28,500 | 2.7 |
| 38 | (H-1) | (39) | (E-6) | 500 | 43,400 | 2.7 |
| 39 | (H-5) | (40) | (E-3) | 730 | 24,900 | 2.3 |
| 40 | (H-1) | (41) | (E-2) | 320 | 19,600 | 2.6 |
| 41 | (H-6) | (42) | (E-4) | 770 | 45,200 | 4.7 |
| 42 | (H-5) | (43) | (E-5) | 400 | 35,100 | 2.9 |
| 43 | (H-2) | (44) | (E-1) | 730 | 26,100 | 2.2 |
| 44 | (H-1) | (45) | (E-4) | 550 | 41,800 | 4.8 |
| 45 | (H-2) | (46) | (E-4) | 440 | 29,900 | 2.9 |
| 46 | (H-3) | (47) | (E-4) | 290 | 9,700 | 1.6 |
| 47 | (H-6) | (48) | (E-4) | 270 | 8,100 | 2.4 |
| 48 | (H-5) | (49) | (E-6) | 690 | 15,000 | 1.0 |
| 49 | (H-2) | (50) | (E-5) | 330 | 48,600 | 5.1 |
| 50 | (H-3) | (51) | (E-6) | 490 | 57,300 | 6.1 |
| 51 | (H-6) | (52) | (E-5) | 280 | 52,800 | 5.6 |
| 52 | (H-2) | (53) | (E-2) | 290 | 41,000 | 5.4 |
| 53 | (H-5) | (54) | (E-3) | 790 | 30,900 | 2.5 |
| 54 | (H-3) | (55) | (E-4) | 440 | 47,800 | 3.9 |
| 55 | (H-3) | (56) | (E-6) | 280 | 47,600 | 4.6 |
| 56 | (H-4) | (57) | (E-2) | 760 | 15,600 | 1.4 |
| 57 | (H-1) | (58) | (E-2) | 700 | 19,000 | 1.7 |
| 58 | (H-4) | (59) | (E-6) | 660 | 14,600 | 1.8 |
| 59 | (H-3) | (60) | (E-4) | 420 | 31,700 | 3.7 |
| 60 | (H-3) | (61) | (E-5) | 560 | 48,900 | 4.3 |
| 61 | (H-2) | (62) | (E-6) | 600 | 44,800 | 5.2 |
| 62 | (H-4) | (63) | (E-4) | 270 | 39,200 | 3.7 |
| 63 | (H-5) | (64) | (E-2) | 330 | 20,700 | 1.6 |
| 64 | (H-6) | (65) | (E-1) | 690 | 7,600 | 1.9 |
| 65 | (H-6) | (66) | (E-3) | 390 | 9,800 | 1.6 |
| 66 | (H-5) | (67) | (E-1) | 770 | 9,200 | 1.7 |
| 67 | (H-4) | (68) | (E-5) | 660 | 9,200 | 1.3 |
| 68 | (H-2) | (69) | (E-6) | 700 | 21,000 | 2.7 |
| 69 | (H-4) | (70) | (E-4) | 210 | 34,100 | 4.6 |
| 70 | (H-5) | (71) | (E-3) | 630 | 47,300 | 4.4 |
| 71 | (H-6) | (72) | (E-3) | 660 | 29,300 | 3.5 |
| 72 | (H-5) | (73) | (E-4) | 510 | 41,400 | 5.1 |
| 73 | (H-1) | (74) | (E-2) | 690 | 18,400 | 1.4 |
| 74 | (H-5) | (75) | (E-3) | 370 | 8,200 | 1.9 |
| 75 | (H-6) | (76) | (E-2) | 570 | 22,500 | 1.6 |
| 76 | (H-1) | (77) | (E-4) | 720 | 39,500 | 4.2 |
| 77 | (H-5) | (78) | (E-5) | 710 | 10,300 | 1.6 |
| 78 | (H-2) | (79) | (E-6) | 780 | 8,900 | 1.2 |
| 79 | (H-5) | (80) | (E-3) | 250 | 21,000 | 2.5 |
| 80 | (H-4) | (81) | (E-6) | 320 | 20,500 | 1.8 |
| 81 | (H-2) | (82) | (E-2) | 310 | 30,200 | 3.7 |
| 82 | (H-4) | (83) | (E-1) | 230 | 36,600 | 3.9 |
| 83 | (H-1) | (84) | (E-1) | 580 | 35,900 | 3.4 |

Ex. = Example, Light emission brightness = value at a direct current of 5 V

Example 84

On a cleaned glass substrate with an ITO electrode, 4,4',4"-tris(N-(3-methylphenyl)-N-phenylamino)triphenylamine was vacuum-deposited to form a first hole-injecting layer having a thickness of 25 nm. Further, a hole-injecting material (H-1) was vacuum-deposited to form a second hole-injecting layer having a thickness of 5 nm. Then, Compound (2) as a light-emitting material was vacuum-deposited to form a light-emitting layer having a thickness of 20 nm. Further, an electron-injecting material (E-1) was vacuum-deposited to form an electron-injecting layer having a thickness of 30 nm. Then, an electrode having a thickness of 150 nm was formed thereon from a magnesium/silver alloy having an magnesium/silver mixing ratio of 10/1, to obtain an organic EL device. The device showed green light emission having a brightness of 650 (cd/m²) at a direct current voltage of 5 V, a maximum brightness of 35,000 (cd/m²) and a light emission efficiency of 3.6 lm/W.

Example 85

On a cleaned glass substrate with an ITO electrode, 4,4',4"-tris(N-(1-naphthyl)-N-phenylamino)triphenylamine was vacuum-deposited to form a first hole-injecting layer having a thickness of 25 nm. Further, a hole-injecting material (H-2) was vacuum-deposited to form a second hole-injecting layer having a thickness of 5 nm. Then, Compound (3) as a light-emitting material was vacuum-deposited to form a light-emitting layer having a thickness of 20 nm. Further, an electron-injecting material (E-5) was vacuum-deposited to form an electron-injecting layer having a thickness of 30 nm. Then, an electrode having a thickness of 150 nm was formed thereon from a magnesium/silver alloy having an magnesium/silver mixing ratio of 10/1, to obtain an organic EL device. The device showed bluish green light emission having a brightness of 710 (cd/m²) at a direct current voltage of 5 V, a maximum brightness of 29,000 (cd/m²) and a light emission efficiency of 2.7 lm/W.

Example 86

A hole-injecting material (H-5) was vacuum-deposited on a cleaned glass substrate with an ITO electrode to form a hole-injecting layer having a thickness of 20 nm. Then, Compound (4) as a light-emitting material was vacuum-deposited to form a light-emitting layer having a thickness of 20 nm. Further, an electron-injecting material (E-2) was vacuum-deposited to form a first electron-injecting layer having a thickness of 20 nm. Then, an electron-injecting material (E-5) was vacuum-deposited to form a second electron-injecting layer having a thickness of 10 nm, and an electrode having a thickness of 150 nm was formed thereon from a magnesium/silver alloy having an magnesium/silver so-obtained devices. All the organic EL devices obtained in these Examples showed high brightness characteristics, or a maximum brightness of at least 20,000 (cd/m$^2$), and gave intended light emission colors.

TABLE 6

| Compound | Chemical structure | Compound | Chemical structure |
|---|---|---|---|
| (D-1) | 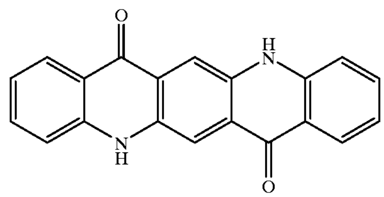 | (D-4) | 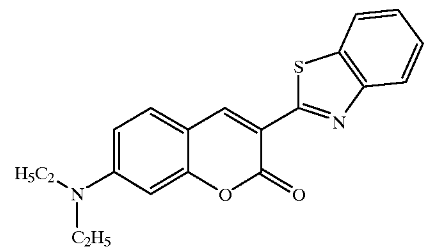 |
| (D-2) | 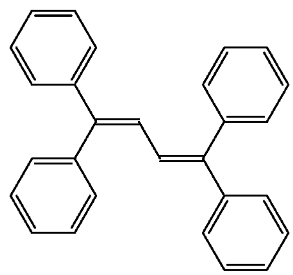 | (D-5) | 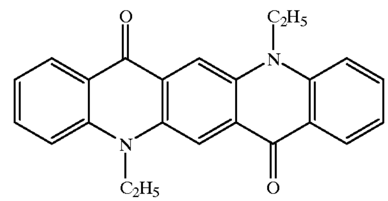 |
| (D-3) | 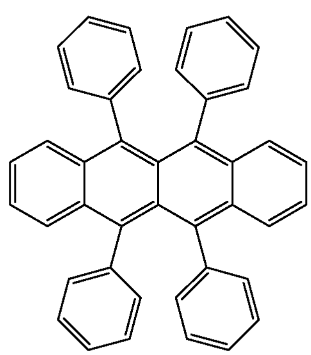 | (D-6) | 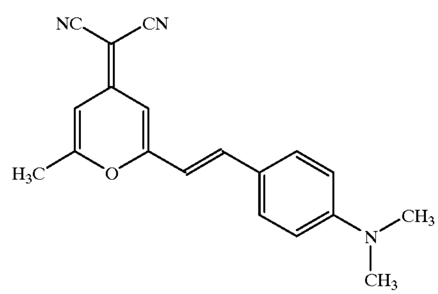 |
| (D-7) | | | | mixing ratio of 10/1, to obtain an organic EL device. The device showed orange light emission having a brightness of 120 (cd/m$^2$) at a direct current voltage of 5 V, a maximum brightness of 15,000 (cd/m$^2$) and a light emission efficiency of 3.2 lm/W.

Examples 87–90

An organic EL device was prepared in the same manner as in Example 5 except that the light-emitting layer was replaced with a 30 nm thick light-emitting layer formed by vacuum-depositing Compound (5) in Table 3 and one of Compounds (D-1) to (D-7) in Table 6 in a weight ratio of 100:1. Table 7 shows light emission characteristics of the so-obtained devices. All the organic EL devices obtained in these Examples showed high brightness characteristics, or a maximum brightness of at least 20,000 (cd/m$^2$), and gave intended light emission colors.

Examples 90–94

An organic EL device was prepared in the same manner as in Example 5 except that the light-emitting layer was replaced with a 30 nm thick light-emitting layer formed by vacuum-depositing Compound (27) in Table 3 and one of Compounds (D-1) to (D-7) in Table 6 in a weight ratio of 100:1. Table 7 shows light emission characteristics of the so-obtained devices. All the organic EL devices obtained in these Examples showed high brightness characteristics, or a maximum brightness of at least 20,000 (cd/m$^2$), and gave intended light emission colors.

Example 95

A hole-injecting material (H-2) was vacuum-deposited on a cleaned glass substrate with an ITO electrode to form a hole-injecting layer having a thickness of 30 nm. Then, 4,4'-bis(β,β-diphenylvinyl)biphenyl and a light-emitting material (1) in Table 3 for a light-emitting layer were vacuum-deposited in a weight ratio of 100:5 to form a light-emitting layer having a thickness of 30 nm. Further, an electron-injecting material (E-3) was vacuum-deposited to form an electron-injecting layer having a thickness of 30 nm. Then, an electrode having a thickness of 150 nm was formed thereon from a magnesium/silver alloy having an magnesium/silver mixing ratio of 10/1, to obtain an organic EL device. The device showed blue light emission having a brightness of 480 (cd/m$^2$) at a direct current voltage of 5 V, a maximum brightness of 28,000 (cd/m$^2$) and a light emission efficiency of 3.1 lm/W.

Examples 96–108

An organic EL device was prepared in the same manner as in Example 95 except that the light-emitting layer was replaced with a 30 nm thick light-emitting layer formed by vacuum-depositing aluminum tris(8-hydroxyquinolinate) and one of the light-emitting materials Table 3 in a weight ratio of 100:3. Table 7 shows light emission characteristics of the so-obtained devices. All the organic EL devices obtained in these Examples showed high brightness characteristics, or a maximum brightness of at least 20,000 (cd/m$^2$).

TABLE 7

| Ex. | Compound (Table 3 or 6) | Light emission brightness (cd/m$^2$) | Maximum light emission brightness (cd/m$^2$) | Maximum light emission efficiency (lm/W) |
| --- | --- | --- | --- | --- |
| 87 | (D-1) | 720 | 78,400 | 8.1 |
| 88 | (D-2) | 310 | 53,700 | 4.5 |
| 89 | (D-3) | 250 | 39,600 | 4.8 |
| 90 | (D-4) | 830 | 37,100 | 3.9 |
| 91 | (D-5) | 260 | 55,200 | 5.2 |
| 92 | (D-6) | 480 | 29,200 | 2.3 |
| 93 | (D-7) | 800 | 37,800 | 3.8 |
| 94 | (D-3) | 810 | 27,700 | 2.4 |
| 96 | (2) | 390 | 58,000 | 6.2 |
| 97 | (4) | 250 | 29,600 | 3.4 |
| 98 | (14) | 220 | 61,800 | 5.1 |
| 99 | (15) | 160 | 54,400 | 3.7 |
| 100 | (23) | 240 | 46,700 | 3.8 |
| 101 | (36) | 870 | 55,200 | 5.9 |
| 102 | (41) | 560 | 26,500 | 4.1 |
| 103 | (54) | 830 | 35,300 | 3.9 |
| 104 | (55) | 870 | 59,200 | 6.7 |
| 105 | (58) | 210 | 24,500 | 2.1 |
| 106 | (64) | 640 | 23,800 | 3.1 |
| 107 | (67) | 660 | 20,700 | 1.9 |
| 108 | (79) | 550 | 25,700 | 2.7 |

Light emission brightness=value at a direct current of 5 V

The organic EL devices obtained in Examples of the present invention showed a light emission brightness of at least 5,000 (cd/m$^2$) and achieved a high light emission efficiency. When the organic EL devices obtained in the above Examples were allowed to continuously emit light at 3 (mA/cm$^2$), all the organic EL devices stably emitted light for more than 1,000 hours, and almost no dark spots were observed. Since the light-emitting materials of the present invention had a very high fluorescence quantum efficiency, the organic EL devices using the light-emitting materials achieved light emission with a high brightness in a low electric current applied region, and when the light-emitting layer used a doping material in addition to the compound of the formula [1], [4] or [5], the organic EL devices were improved in maximum light emission brightness and maximum light emission efficiency. Further, by adding a doping material having a different fluorescent color to the light-emitting material of the present invention, there were obtained light-emitting devices having a different light emission color.

The organic EL device of the present invention accomplishes improvements in light emission efficiency and light emission brightness and a longer device life, and does not impose any limitations on a light-emitting material, a dopant, a hole-injecting material, an electron-injecting material, a sensitizer, a resin and an electrode material used in combination and the method of producing the device.

The organic EL device using the material of the present invention as a light-emitting material achieves light emission having a high brightness with a high light emission efficiency and a longer life as compared with conventional devices. According to the light-emitting material of the present invention and the organic EL device of the present invention, there can be achieved an organic EL device having a high brightness, a high light emission efficiency and a long life.

What is claimed is:

1. A light-emitting material of the formula [1]

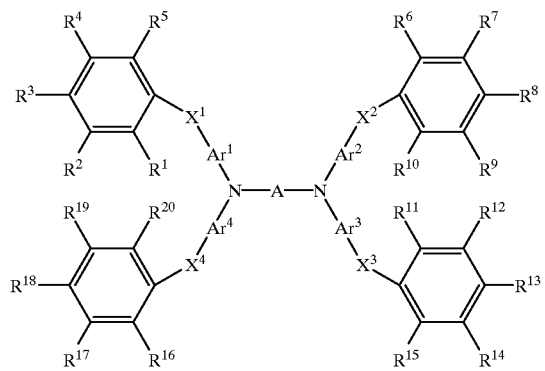

[1]

wherein A is a substituted or non-substituted divalent aromatic group, a substituted or non-substituted heteroaromatic divalent group, or a divalent group in which 2 to 10 identical or different groups out of the above groups are bonded to each other directly or through at least one of an oxygen atom, a nitrogen atom, a sulfur atom, a linear structural unit having 1 to 20 carbon atoms and optionally containing a hetero-atom, or a non-aromatic ring structural unit, with the proviso that A does not encompass a fused aromatic group or an amino group, each of Ar$^1$ to Ar$^4$ is independently a substituted or non-substituted aromatic group or a substituted or non-substituted fused aromatic group, each of X$^1$ to X$^4$ is independently >C=O, >SO$_2$, —(C$_x$H$_{2x}$)—O—(C$_y$H$_{2y}$)— (in which each of x and y is an integer of 0 to 20, while x+y=0 in no case), a substituted or non-substituted alkylidene group having 2 to 20 carbons, a substituted or non-substituted alkylene group having 2 to 20 carbon atoms or a substituted or non-substituted divalent alicyclic residue, and each of R$^1$ to R$^{20}$ is independently a hydrogen atom, a halogen atom, a substituted or non-substituted alkyl group, a substituted or non-substituted alkoxy group, a substituted or non-substituted aromatic group, a substituted or non-substituted hetero-aromatic group or a substituted or non-substituted amino group (provided that adjacent groups of $R^1$ to $R^5$, $R^6$ to $R^{10}$, $R^{11}$ to $R^{15}$, or $R^{16}$ to $R^{20}$ may bond to each other to form a fresh ring).

2. An organic EL device comprising a light-emitting layer or a plurality of organic compound layers including the light-emitting layer and a pair of electrodes, the light-emitting layer or a plurality of the organic compound layers being sandwiched between a pair of the electrodes, wherein the light-emitting layer contains the light-emitting material recited in claim 1.

3. A light-emitting material of the formula [4]

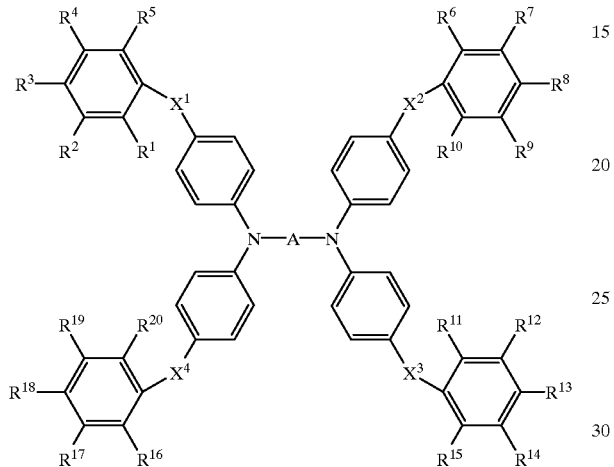

[4]

wherein A is a substituted or non-substituted divalent aromatic group, a substituted or non-substituted hetero-aromatic divalent group, or a divalent group in which 2 to 10 identical or different groups out of the above groups are bonded to each other directly or through at least one of an oxygen atom, a nitrogen atom, a sulfur atom, a linear structural unit having 1 to 20 carbon atoms and optionally containing a hetero-atom, or a non-aromatic ring structural unit, with the proviso that A does not encompass a fused aromatic group or an amino group, each of $X^1$ to $X^4$ is independently >C=O, >SO$_2$, —(C$_x$H$_{2x}$)—O—(C$_y$H$_{2y}$)— (in which each of x and y is an integer of 0 to 20, while x+y=0 in no case), a substituted or non-substituted alkylidene group having 2 to 20 carbons, a substituted or non-substituted alkylene group having 2 to 20 carbon atoms or a substituted or non-substituted divalent alicyclic residue, and each of $R^1$ to $R^{20}$ is independently a hydrogen atom, a halogen atom, a substituted or non-substituted alkyl group, a substituted or non-substituted alkoxy group, a substituted or non-substituted aromatic group, a substituted or non-substituted hetero-aromatic group or substituted or non-substituted amino group (provide that adjacent groups of $R^1$ to $R^5$, $R^6$ to $R^{10}$, $R^{11}$ to $R^{15}$, or $R^{16}$ to $R^{20}$ may bond to each other to form a fresh ring).

4. An organic EL device comprising a light-emitting layer or a plurality of organic compound layers including the light-emitting layer and a pair of electrodes, the light-emitting layer or a plurality of the organic compound layers being sandwiched between a pair of the electrodes, wherein the light-emitting layer contains the light-emitting material recited in claim 3.

5. A light-emitting material of the formula [5]

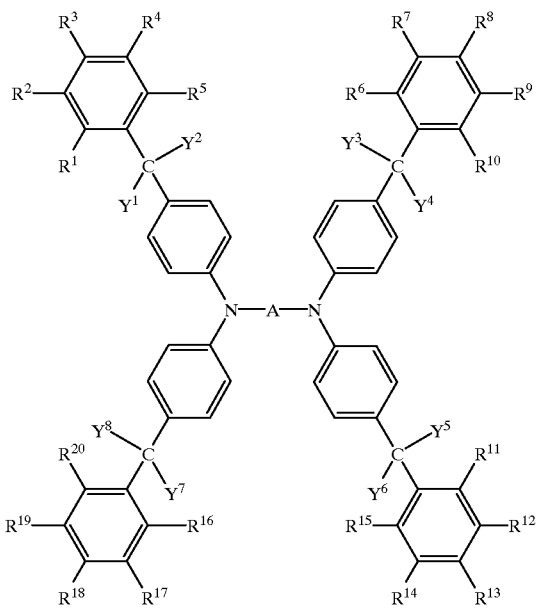

[5]

wherein A is a substituted or non-substituted divalent aromatic group, a substituted or non-substituted hetero-aromatic divalent group, or a divalent group in which 2 to 10 identical or different groups out of the above groups are bonded to each other directly or through at least one of an oxygen atom, a nitrogen atom, a sulfur atom, a linear structural unit having 1 to 20 carbon atoms and optionally containing a hetero-atom, or a non-aromatic ring structural unit, with the proviso that A does not encompass a fused aromatic group or an amino group, each of $R^1$ to $R^{20}$ is independently a hydrogen atom, a halogen atom, a substituted or non-substituted alkyl group, a substituted or non-substituted alkoxy group, a substituted or non-substituted aromatic group, a substituted or non-substituted hetero-aromatic group or a substituted or non-substituted amino group (provided that adjacent groups of $R^1$ to $R^5$, $R^6$ to $R^{10}$, $R^{11}$ to $R^{15}$, or $R^{16}$ to $R^{20}$ may bond to each other to form a fresh ring), and each of $Y^1$ to $Y^8$ is a substituted or non-substituted alkyl group having 1 to 20 carbon atoms or a substituted or non-substituted aromatic group having 6 to 16 carbon atoms (provided that groups of $Y^1$ and $Y^2$, $Y^3$ and $Y^4$, $Y^5$ and $Y^6$, or $Y^7$ and $Y^8$ may form a substituted or non-substituted alicyclic group having 5 to 7 carbon atoms).

6. An organic EL device comprising a light-emitting layer or a plurality of organic compound layers including the light-emitting layer and a pair of electrodes, the light-emitting layer or a plurality of the organic compound layers being sandwiched between a pair of the electrodes, wherein the light-emitting layer contains the light-emitting material recited in claim 5.

\* \* \* \* \*